(12) United States Patent
Cotteret et al.

(10) Patent No.: US 7,101,406 B2
(45) Date of Patent: Sep. 5, 2006

(54) DYEING COMPOSITION COMPRISING A CATIONIC TERTIARY PARA-PHENYLENEDIAMINE AND A HETEROCYCLIC CATIONIC DIRECT DYE, METHODS AND USES

(75) Inventors: Jean Cotteret, Verneuil sur Seine (FR); Alain Lagrange, Coupvray (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/735,259

(22) Filed: Dec. 12, 2003

(65) Prior Publication Data

US 2004/0221399 A1    Nov. 11, 2004

Related U.S. Application Data

(60) Provisional application No. 60/444,641, filed on Feb. 4, 2003.

(30) Foreign Application Priority Data

Dec. 13, 2002    (FR) .................................. 02 15772

(51) Int. Cl.
*A61K 7/13* (2006.01)
(52) U.S. Cl. ...................... 8/405; 8/407; 8/437; 8/451; 8/463; 8/570; 8/572; 8/573; 8/574; 548/318.1; 548/321; 548/400; 546/184; 546/249
(58) Field of Classification Search .................... 8/405, 8/406, 407, 410, 411, 412, 415, 421, 437, 8/455, 565, 566, 573, 451, 463, 588, 570, 8/572, 574; 548/318.1, 321, 400; 546/184, 546/249
See application file for complete search history.

(56) References Cited

U.S. PATENT DOCUMENTS

| | | | | |
|---|---|---|---|---|
| 5,674,299 A | * | 10/1997 | Kaser ............................. | 8/655 |
| 5,708,151 A | * | 1/1998 | Mockli ....................... | 534/608 |
| 6,461,391 B1 | * | 10/2002 | Lim et al. ....................... | 8/405 |
| 2002/0106341 A1 | | 8/2002 | Lim et al. ................... | 424/70.1 |
| 2002/0144356 A1 | * | 10/2002 | Kawai et al. ................... | 8/405 |
| 2003/0106169 A1 | * | 6/2003 | Vidal et al. ..................... | 8/405 |
| 2004/0093675 A1 | * | 5/2004 | Vidal et al. .................... | 8/405 |
| 2004/0093676 A1 | * | 5/2004 | Vidal et al. .................... | 8/405 |
| 2004/0123400 A1 | * | 7/2004 | Vidal et al. .................... | 8/405 |
| 2004/0168263 A1 | * | 9/2004 | Vidal ............................ | 8/405 |
| 2004/0187225 A1 | * | 9/2004 | Vidal et al. .................... | 8/405 |

FOREIGN PATENT DOCUMENTS

| | | |
|---|---|---|
| EP | 0 953 334 | 11/1999 |
| EP | 0 960 617 | 12/1999 |
| EP | 1 149 575 | 10/2001 |
| FR | 2 805 741 | 9/2001 |
| FR | 2 822 696 | 10/2002 |
| FR | 2 822 698 | 10/2002 |
| FR | 2822696 | * 10/2002 |
| FR | 2822698 | * 10/2002 |
| WO | WO 02/078657 | * 10/2002 |
| WO | WO 02/078658 | * 10/2002 |
| WO | WO 02/078659 | * 10/2002 |

OTHER PUBLICATIONS

R.D. Lillie, Aldrich chemical catalogue, 1992.*

* cited by examiner

*Primary Examiner*—Eisa Elhilo
(74) *Attorney, Agent, or Firm*—Fulbright & Jaworski L.L.P.

(57) ABSTRACT

The subject of the present application is a dyeing composition for dyeing keratinous fibers, in particular human keratinous fibres such as hair, comprising, in an appropriate dyeing medium, at least one cationic tertiary para-phenylenediamine containing a pyrrolidine ring, and at least one cationic direct dye comprising at least one heterocyclic group.

The subject of the invention is also the dyeing method using this composition and the corresponding devices.

100 Claims, No Drawings

DYEING COMPOSITION COMPRISING A CATIONIC TERTIARY PARA-PHENYLENEDIAMINE AND A HETEROCYCLIC CATIONIC DIRECT DYE, METHODS AND USES

CROSS REFERENCE TO RELATED APPLICATIONS

This application claims priority to French Application No. 02/15772 filed 13 Dec. 2002, and further claims the benefit of U.S. Provisional Application No. 60/444,641 filed 04 Feb. 2003, the entire disclosures of which are incorporated herein by reference in their entirety.

BACKGROUND OF THE INVENTION

The subject of the present application is a dyeing composition for dyeing keratinous fibres, in particular human keratinous fibres such as hair, comprising, in an appropriate dyeing medium, at least one cationic tertiary para-phenylenediamine containing a pyrrolidine ring, and at least one cationic direct dye comprising at least one heterocycle group.

The subject of the invention is also the use of this composition for dyeing keratinous fibres and the dyeing method using this composition.

It is known to dye keratinous fibres, and in particular human hair, with dyeing compositions containing oxidation dye precursors, generally called oxidation bases, such as ortho- or para-phenylenediamines, or ortho- or para-aminophenols and heterocyclic compounds. These oxidation bases are colourless or weakly coloured compounds which, when combined with oxidizing products, can give rise, through a process of oxidative condensation, to coloured compounds.

It is also known that it is possible to vary the shades obtained with these oxidation bases by combining them with couplers or colour modifiers, the latter being chosen in particular from aromatic meta-diamines, meta-aminophenols, meta-diphenols and certain heterocyclic compounds such as indole compounds.

The variety of molecules used in the oxidation bases and couplers allows a rich palette of colours to be obtained.

The so-called "permanent" coloration obtained using these oxidation dyes should moreover satisfy a number of requirements. Thus, it should be without disadvantage from the toxicological point of view, it should make it possible to obtain shades in the desired intensity and should exhibit good fastness to external agents such as light, adverse weather conditions, washing, permanent waving, perspiration and rubbing.

The dyes should also make it possible to cover grey hair, and should finally be as less selective as possible, that is to say it is possible to obtain the least possible colour variations along the length of the same keratinous fibre, which is in general differentially sensitized (that is to say damaged) between its tip and its root.

It has already been proposed, in patent application WO 02/45675, to use compositions for the oxidation dyeing of keratinous fibres comprising a cationic tertiary para-phenylenediamine containing a pyrrolidine ring.

These cationic tertiary para-phenylenediamines containing a pyrrolidine ring lead to compositions which exhibit a harmlessness which is generally considered better than the compositions containing conventional para-phenylenediamines. However, the shades obtained when these compositions are used are markedly less intense and markedly more selective, that is to say that the dyes obtained exhibit substantial variations in colorations as a function of the degree of sensitization of the various types of hair or of the various areas of the same hair. The fastness of these shades can also vary greatly according to the degree of sensitization. In addition, the colorations obtained are also often more grey, that is to say less chromatic.

SUMMARY OF THE INVENTION

Surprisingly and advantageously, the applicant has just discovered that it is possible to obtain novel compositions for dyeing keratinous fibres, in particular human keratinous fibres such as hair, capable of overcoming the disadvantages cited above and of leading to colorations with shades which are varied, chromatic, intense, aesthetic, not very selective and which withstand well the various attacks to which the fibres may be subjected, by combining, in the same composition, at least one cationic tertiary para-phenylenediamine containing a pyrrolidine ring and at least one cationic direct dye comprising a heterocycle group. In addition, these compositions exhibit a good toxicological profile.

The subject of the invention is thus a dyeing composition for dyeing keratinous fibres comprising, in an appropriate dyeing medium, at least one cationic tertiary para-phenylenediamine containing a pyrrolidine ring and at least one cationic direct dye comprising a heterocyclic group.

The subject of the invention is also a dyeing method using this composition, and a multicompartment dyeing device or dyeing kit.

Another subject of the invention is the use of the composition of the present invention for dyeing keratinous fibres, in particular human keratinous fibres such as hair.

The composition of the present invention makes it possible in particular to obtain a chromatic coloration of keratinous fibres which is very intense, little selective and fast while avoiding degradation of these fibres.

Further purposes of the present invention, cationic tertiary para-phenylenediamine containing a pyrrolidine ring is understood to mean a para-phenylenediamine possessing an $NH_2$ group and in the para position thereof a di-substituted amine functional group whose substitutions form with the nitrogen a pyrrolidine ring, the molecule possessing at least one quaternarized nitrogen atom borne by the para-phenylenediamine ortho or meta to the $NH_2$ group or by the pyrrolidine ring.

In the context of the present invention, the expression alkyl is understood to mean linear or branched radicals, for example methyl, ethyl, n-propyl, isopropyl, butyl and the like. An alkoxy radical is an alk—O radical, the alkyl radical having the definition above. Halogen preferably denotes Cl, Br, I, F.

Among the cationic tertiary para-phenylenediamines containing a pyrrolidine ring which can be used in the composition according to the present invention, there may be mentioned in particular the compounds of the following formula (I) and their addition salts.

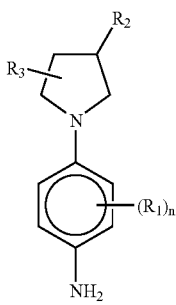

(I)

in which n varies from 0 to 4, it being understood that when n is greater than or equal to 2, then the radicals $R_1$ may be identical or different, $R_1$ represents a halogen atom; a saturated or unsaturated, aliphatic or alicylic, $C_1$–$C_6$ hydrocarbon chain, it being possible for the chain to contain one or more oxygen, nitrogen, silicon or sulphur atoms or an $SO_2$ group, and it being possible for the chain to be substituted with one or more hydroxyl or amino radicals; an onium radical Z, the radical $R_1$ not containing a peroxide bond, or diazo, nitro or nitroso radicals, $R_2$ represents an onium radical Z or a radical —X—C=NR$_8$—NR$_9$R$_{10}$ in which X represents an oxygen atom or a radical —NR$_{11}$ and $R_8$, $R_9$, $R_{10}$ and $R_{11}$ represent a hydrogen atom, a $C_1$–$C_4$ alkyl radical or a $C_1$–$C_4$ hydroxyalkyl radical, $R_3$ represents a hydrogen atom or a hydroxyl radical.

Onium denotes the quaternary radical of a nitrogenous base.

By way of example, $R_1$ may be a chlorine atom, a methyl, ethyl, isopropyl, vinyl, allyl, methoxymethyl, hydroxyethyl, 1-carboxymethyl, 1-aminomethyl, 2-carboxymethyl, 2-hydroxyethyl, 3-hydroxypropyl, 1,2-dihydroxyethyl, 1-hydroxy-2-aminoethyl, 1-amino-2-hydroxyethyl, 1,2-diaminoethyl, methoxy, ethoxy, allyloxy, or 2-hydroxyethyloxy radical.

In particular, n is equal to 0.

In formula (I), when n is equal to 1, $R_1$ is preferably a halogen atom; a saturated or unsaturated, aliphatic or alicylic, $C_1$–$C_6$ hydrocarbon chain, it being possible for one or more carbon atoms to be replaced with an oxygen, nitrogen, silicon or sulphur atom, or with an $SO_2$ group, the radical $R_1$ not containing a peroxide bond, or diazo, nitro or nitroso radicals. Preferably, $R_1$ is chosen from chlorine, bromine, $C_1$–$C_4$ alkyl, $C_1$–$C_4$ hydroxyalkyl, $C_1$–$C_4$ aminoalkyl, $C_1$–$C_4$ alkoxy and $C_1$–$C_4$ hydroxyalkoxy radicals. By way of example, $R_1$ is chosen from a methyl, hydroxymethyl, 2-hydroxyethyl, 1,2-dihydroxyethyl, methoxy, isopropyloxy or 2-hydroxyethoxy radical.

The radical $R_2$ of formula (I) is, according to a particular embodiment, the onium radical Z corresponding to formula (II)

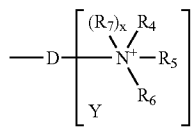

(II)

in which

D is a single bond of a linear or branched $C_1$–$C_{14}$ alkylene chain which may contain one or more heteroatoms chosen from oxygen, sulphur or nitrogen, and which may be substituted with one or more hydroxyl, $C_1$–$C_6$ alkoxy or amino radicals and which may carry one or more ketone functional groups;

$R_4$, $R_5$ and $R_6$, taken separately, represent a $C_1$–$C_{15}$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$) alkyl radical; an aryl radical; a benzyl radical; a $C_1$–$C_6$ amidoalkyl radical; a tri($C_1$–$C_6$)alkylsilane($C_1$–$C_6$) alkyl radical; a $C_1$–$C_6$ aminoalkyl radical; a $C_1$–$C_6$ aminoalkyl radical in which the amine is mono- or di-substituted with a $C_1$–$C_4$ alkyl, ($C_1$–$C_6$)alkylcarbonyl, amido or ($C_1$–$C_6$)alkylsulphonyl radical; or $R_4$, $R_5$ and $R_6$ together, in pairs, form, with the nitrogen atom to which they are attached, a 4-, 5-, 6- or 7-membered saturated carbon ring which may contain one or more heteroatoms such as, for example, azetidine ring, a pyrrolidine ring, a piperidine ring, a piperazine ring, or a morpholine ring, it being possible for the cationic ring to be substituted with a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical, a tri($C_1$–$C_6$)alkylsilane ($C_1$–$C_6$)alkyl radical, an amido radical, a carboxyl radical, a ($C_1$–$C_6$)alkylcarbonyl radical, a thio (—SH) radical, a $C_1$–$C_6$ thioalkyl (—R—SH) radical, a ($C_1$–$C_6$)alkylthio radical, an amino radical, an amino radical which is mono- or di-substituted with a ($C_1$–$C_6$) alkyl, ($C_1$–$C_6$)alkylcarbonyl, amido or ($C_1$–$C_6$)alkylsulphonyl radical;

$R_7$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical; a $C_1$–$C_6$ aminoalkyl radical whose amine is mono- or di-substituted with a ($C_1$–$C_6$)alkyl, ($C_1$–$C_6$) alkylcarbonyl, amido or ($C_1$–$C_6$)alkylsulphonyl radical; a $C_1$–$C_6$ carboxyalkyl radical; a $C_1$–$C_6$ carbamylalkyl radical; a $C_1$–$C_6$ trifluoroalkyl radical; a tri ($C_1$–$C_6$)alkylsilane($C_1$–$C_6$)alkyl radical; a $C_1$–$C_6$ sulphonamidoalkyl radical; a ($C_1$–$C_6$)alkylcarboxy ($C_1$–$C_6$)alkyl radical; a ($C_1$–$C_6$)alkylsulphinyl($C_1$–$C_6$) alkyl radical; a ($C_1$–$C_6$)alkyl-sulphonyl ($C_1$–$C_6$)alkyl radical; a ($C_1$–$C_6$)alkylcarbonyl($C_1$–$C_6$)alkyl radical; an N—($C_1$–$C_6$)alkylcarbamyl($C_1$–$C_6$)alkyl radical; an N—($C_1$–$C_6$)alkylsulphonamido($C_1$–$C_6$)alkyl radical;

x is 0 or 1, when x=0, then the linking arm is attached to the nitrogen atom carrying the radicals $R_4$ to $R_6$;

when x=1, then two of the radicals $R_4$ to $R_6$ form, together with the nitrogen atom to which they are attached, a 4-, 5-, 6- or 7-membered saturated ring and D is linked to the carbon atom of the saturated ring;

Y is a counter-ion.

In formula (II), when x is equal to 0, then $R_4$, $R_5$ and $R_6$ separately are preferably chosen from a $C_1$–$C_6$ alkyl radical, a $C_1$–$C_4$ monohydroxyalkyl radical, a $C_2$–$C_4$ polyhydroxyalkyl radical, a ($C_1$–$C_6$)alkoxy($C_1$–$C_4$)alkyl radical, a $C_1$–$C_6$ amidoalkyl radical, a tri($C_1$–$C_6$)alkylsilane($C_1$–$C_6$)alkyl radical, or $R_4$ with $R_5$ form together an azetidine ring, a pyrrolidine, piperidine, piperazine or morpholine ring, $R_6$ being chosen in this case from a $C_1$–$C_6$ alkyl radical; a $C_1$–$C_6$ monohydroxyalkyl radical, a $C_2$–$C_6$ polyhydroxyalkyl radical; a $C_1$–$C_6$ aminoalkyl radical, an aminoalkyl radical which is mono- or di-substituted with a ($C_1$–$C_6$)alkyl radical, a ($C_1$–$C_6$)alkylcarbonyl, amido or ($C_1$–$C_6$)alkylsulphonyl radical; a $C_1$–$C_6$ carbamylalkyl radical; a tri($C_1$–$C_6$)alkylsilane($C_1$–$C_6$)alkyl radical; a ($C_1$–$C_6$)alkyl carboxy ($C_1$–$C_6$)alkyl radical; a ($C_1$–$C_6$)alkylcarbonyl($C_1$–$C_6$)alkyl radical; an N—($C_1$–$C_6$)alkylcarbamyl($C_1$–$C_6$)alkyl radical.

When x is equal to 1, then $R_7$ is preferably chosen from a $C_1$–$C_6$ alkyl radical; a $C_1$–$C_6$ monohydroxyalkyl radical; a $C_2$–$C_6$ polyhydroxy alkyl radical, a $C_1$–$C_6$ aminoalkyl radical, a $C_1$–$C_6$ aminoalkyl radical whose amine is mono- or di-substituted with a ($C_1$–$C_6$)alkyl, ($C_1$–$C_6$)alkylcarbonyl, amido or a ($C_1$–$C_6$)alkylsulphonyl radical; a $C_1$–$C_6$ carbamylalkyl radical, a tri($C_1$–$C_6$)alkylsilane($C_1$–$C_6$)alkyl radical; a ($C_1$–$C_6$)alkylcarboxy($C_1$–$C_6$)alkyl radical; a ($C_1$–$C_6$)alkylcarbonyl($C_1$–$C_6$)alkyl radical; an N—($C_1$–$C_6$) alkylcarbamyl($C_1$–$C_6$)alkyl radical; $R_4$ with $R_5$ together form an azetidine, pyrrolidine, piperidine, piperazine or morpholine ring, $R_6$ being chosen in this case from a $C_1$–$C_6$ alkyl radical; a $C_1$–$C_6$ monohydroxyalkyl radical; a $C_2$–$C_6$ polyhydroxyalkyl radical; a $C_1$–$C_6$ aminoalkyl radical, a $C_1$–$C_6$ aminoalkyl radical whose amine is mono- or di-substituted with a ($C_1$–$C_6$)alkyl, ($C_1$–$C_6$)alkylcarbonyl, amido or ($C_1$–$C_6$)alkylsulphonyl radical; a $C_1$–$C_6$ carbamylalkyl radical; a tri($C_1$–$C_6$)alkylsilane($C_1$–$C_6$)alkyl radical; a ($C_1$–$C_6$)alkylcarboxy($C_1$–$C_6$)alkyl radical; a ($C_1$–$C_6$)alkylcarbonyl($C_1$–$C_6$)alkyl radical; an N—($C_1$–$C_6$)alkylcarbamyl($C_1$–$C_6$)alkyl radical.

In the formula (II), D is preferably a single bond or an alkylene chain which may be substituted.

When the radical $R_2$ corresponds to formula (II), it is preferably a trialkylammonium radical whose alkyl radicals may be substituted.

According to a second embodiment, the radical $R_2$ represents the onium radical Z corresponding to formula (III)

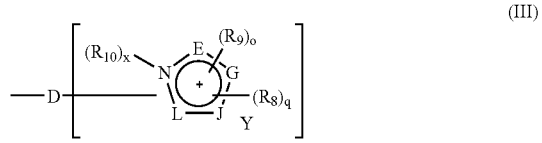

(III)

in which

D is a single bond or a linear or branched $C_1$–$C_{14}$ alkylene chain which may be interrupted by one or more heteroatoms chosen from oxygen, sulphur or nitrogen, and which may be substituted with one or more hydroxyl, $C_1$–$C_6$ alkoxy or amino radicals, and which may carry one or more ketone functional groups;

the vertices E, G, J, L, which are identical or different, represent a carbon, oxygen, sulphur or nitrogen atom to form a pyrrole, pyrazole, imidazole, triazole, oxazole, isooxazole, thiazole, isothiazole ring, q is an integer between 0 and 4 inclusive;
o is an integer between 0 and 3 inclusive;
q+o is an integer between 0 and 4;

the radicals $R_8$, which are identical or different, represent a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical, a tri($C_1$–$C_6$)alkylsilane($C_1$–$C_6$)alkyl radical, an amido radical, a carboxyl radical, a $C_1$–$C_6$ alkylcarbonyl radical, a thio radical, a $C_1$–$C_6$ thioalkyl radical, a ($C_1$–$C_6$) alkylthio radical, an amino radical, an amino radical which is mono- or di-substituted with a ($C_1$–$C_6$)alkyl, ($C_1$–$C_6$)alkylcarbonyl, amido or ($C_1$–$C_6$)alkylsulphonyl radical; a $C_1$–$C_6$ monohydroxyalkyl radical or a $C_2$–$C_6$ polyhydroxyalkyl radical; it being understood that the radicals $R_8$ are carried by a carbon atom, the radicals $R_9$, which are identical or different, represent a $C_1$–$C_6$ alkyl radical, a $C_1$–$C_6$ monohydroxyalkyl radical, a $C_2$–$C_6$ polyhydroxyalkyl radical, a tri($C_1$–$C_6$) alkylsilane($C_1$–$C_6$)alkyl radical, a ($C_1$–$C_6$)alkoxy ($C_1$–$C_6$)alkyl radical, a $C_1$–$C_6$ carbamylalkyl radical, a ($C_1$–$C_6$)alkylcarboxy($C_1$–$C_6$)alkyl radical, a benzyl radical; it being understood that the radicals $R_9$ are carried by a nitrogen, $R_{10}$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical whose amine is substituted with a ($C_1$–$C_6$)alkyl, ($C_1$–$C_6$)alkylcarbonyl, amido or ($C_1$–$C_6$)alkylsulphonyl radical; a $C_1$–$C_6$ carboxyalkyl radical; a $C_1$–$C_6$ carbamylalkyl radical; a $C_1$–$C_6$ trifluoroalkyl radical; a tri($C_1$–$C_6$)alkylsilane ($C_1$–$C_6$)alkyl radical; a $C_1$–$C_6$ sulphonamidoalkyl radical; a ($C_1$–$C_6$)alkylcarboxy($C_1$–$C_6$)alkyl radical; a ($C_1$–$C_6$)alkylsulphinyl($C_1$–$C_6$)alkyl radical; a ($C_1$–$C_6$) alkylsulphonyl($C_1$–$C_6$)alkyl radical; a ($C_1$–$C_6$)alkylcarbonyl($C_1$–$C_6$)alkyl radical; an N—($C_1$–$C_6$)alkylcarbamyl($C_1$–$C_6$)alkyl radical; an N—($C_1$–$C_6$) alkylsulphonamido($C_1$–$C_6$)alkyl radical;

x is 0 or 1
 when x=0, the linking arm D is attached to the nitrogen atom,
 when x=1, the linking arm D is attached to one of the vertices E, G, J or L, Y is a counter-ion.

The vertices E, G, J and L preferably form a imidazole ring.

Among the radicals $R_2$ of formulae (III), the preferred radicals are those in which x is equal to 0, D is a single bond or an alkylene chain which may be substituted.

According to a third embodiment, $R_2$ represents the onium radical Z corresponding to formula (IV)

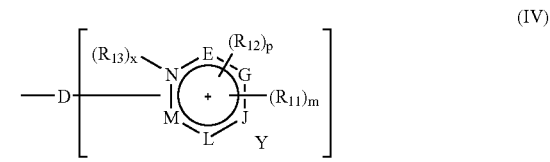

(IV)

in which:

D is a single bond or a linear or branched $C_1$–$C_{14}$ alkylene chain which may contain one or more heteroatoms chosen from an oxygen, sulphur or nitrogen atom, and which may be substituted with one or more hydroxyl, $C_1$–$C_6$ alkoxy or amino radicals, and which may carry one or more ketone functional groups;

the vertices E, G, J, L and M, which are identical or different, represent a carbon, oxygen, sulphur or nitrogen atom to form a ring chosen from the pyridine, pyrimidine, pyrazine, triazine and pyridazine rings;

p is an integer between 0 and 3 inclusive;
m is an integer between 0 and 5 inclusive;
p+m is an integer between 0 and 5;

the radicals $R_{11}$, which are identical or different, represent a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical, a tri($C_1$–$C_6$)alkylsilane($C_1$–$C_6$)alkyl radical, an amido radical, a carboxyl radical, a $C_1$–$C_6$ alkylcarbonyl radical, a thio radical, a $C_1$–$C_6$ thioalkyl radical, a ($C_1$–$C_6$) alkylthio radical, an amino radical, an amino radical which is substituted with a ($C_1$–$C_6$)alkyl, ($C_1$–$C_6$) alkylcarbonyl, amido or ($C_1$–$C_6$)alkylsulphonyl radical; a $C_1$–$C_6$ monohydroxyalkyl radical or a $C_2$–$C_6$ polyhydroxyalkyl radical; it being understood that the radicals $R_1$, are carried by a carbon atom, the radicals $R_{12}$, which are identical or different, represent a $C_1$–$C_6$ alkyl radical, a $C_1$–$C_6$ monohydroxyalkyl radical, a $C_2$–$C_6$ polyhydroxyalkyl radical, a tri($C_1$–$C_6$) alkylsilane($C_1$–$C_6$)alkyl radical, a ($C_1$–$C_6$)alkoxy ($C_1$–$C_6$)alkyl radical, a $C_1$–$C_6$ carbamylalkyl radical, a ($C_1$–$C_6$)alkylcarboxy($C_1$–$C_6$)alkyl radical, a benzyl radical; it being understood that the radicals $R_{12}$ are carried by a nitrogen, $R_{13}$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical whose amine is mono- or di-substituted with a ($C_1$–$C_6$)alkyl, ($C_1$–$C_6$) alkylcarbonyl, amido or ($C_1$–$C_6$)alkylsulphonyl radical; a $C_1$–$C_6$ carboxyalkyl radical; a $C_1$–$C_6$ carbamylalkyl radical; a $C_1$–$C_6$ trifluoroalkyl radical; a tri ($C_1$–$C_6$)alkylsilane($C_1$–$C_6$)alkyl radical; a $C_1$–$C_6$ sulphonamidoalkyl radical; a ($C_1$–$C_6$)alkylcarboxy ($C_1$–$C_6$)alkyl radical; a ($C_1$–$C_6$)alkylsulphinyl($C_1$–$C_6$) alkyl radical; a ($C_1$–$C_6$)alkylsulphonyl($C_1$–$C_6$)alkyl radical; a ($C_1$–$C_6$)alkylcarbonyl($C_1$–$C_6$)alkyl radical; an N—($C_1$–$C_6$)alkylcarbamyl($C_1$–$C_6$)alkyl radical; an N—($C_1$–$C_6$)alkylsulphonamido($C_1$–$C_6$)alkyl radical;

x is 0 or 1
when x=0, the linking arm D is attached to the nitrogen atom,
when x=1, the linking arm D is attached to one of the vertices E, G, J, L or M, Y is a counter-ion.

Preferably, the vertices E, G, J, L and M form, with the nitrogen of the ring, a pyridine and pyrimidine ring When x is equal to 0, then $R_{11}$, is preferably chosen from a hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical, a tri($C_1$–$C_6$)alkylsilane($C_1$–$C_6$)alkyl radical, an amido radical, a $C_1$–$C_6$ alkylcarbonyl radical, an amino radical, an amino radical which is mono- or di-substituted with a ($C_1$–$C_6$)alkyl, a ($C_1$–$C_6$)alkylcarbonyl, amido or ($C_1$–$C_6$)alkylsulphonyl radical; a $C_1$–$C_6$ monohydroxyalkyl radical or a $C_2$–$C_6$ polyhydroxyalkyl radical and $R_{12}$ is chosen from a $C_1$–$C_6$ alkyl radical, a $C_1$–$C_6$ monohydroxyalkyl radical, a $C_2$–$C_6$ polyhydroxyalkyl radical, a tri($C_1$–$C_6$)alkylsilane($C_1$–$C_6$)alkyl radical, a ($C_1$–$C_6$)alkoxy ($C_1$–$C_6$)alkyl radical, a $C_1$–$C_6$ carbamylalkyl radical.

When x is equal to 1, $R_{13}$ is preferably chosen from a $C_1$–$C_6$ alkyl radical; a $C_1$–$C_6$ monohydroxyalkyl radical; a $C_2$–$C_6$ polyhydroxyalkyl radical; a $C_1$–$C_6$ aminoalkyl radical, a $C_1$–$C_6$ aminoalkyl radical whose amine is mono- or di-substituted with a ($C_1$–$C_6$)alkyl radical, a ($C_1$–$C_6$)alkylcarbonyl radical, an amido radical, a ($C_1$–$C_6$)alkylsulphonyl radical; a $C_1$–$C_6$ carbamylalkyl radical; a tri($C_1$–$C_6$)alkylsilane($C_1$–$C_6$)alkyl radical; a ($C_1$–$C_6$)alkylcarbonyl($C_1$–$C_6$) alkyl radical; an N—($C_1$–$C_6$)alkylcarbamyl($C_1$–$C_6$)alkyl radical; $R_{11}$ is chosen from a hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical, a tri($C_1$–$C_6$) alkylsilane($C_1$–$C_6$)alkyl radical, an amido radical, a $C_1$–$C_6$ alkylcarbonyl radical, an amino radical, an amino radical which is mono- or di-substituted with a ($C_1$–$C_6$)alkyl, ($C_1$–$C_6$)alkylcarbonyl, amido or ($C_1$–$C_6$)alkylsulphonyl radical; and $R_{12}$ is chosen from a $C_1$–$C_6$ alkyl radical, a $C_1$–$C_6$ monohydroxyalkyl radical, a $C_2$–$C_6$ polyhydroxyalkyl radical, a tri($C_1$–$C_6$)alkylsilane($C_1$–$C_6$)alkyl radical, a ($C_1$–$C_6$)alkoxy($C_1$–$C_6$)alkyl radical, a $C_1$–$C_6$ carbamylalkyl radical.

Preferably, $R_{11}$, $R_{12}$ and $R_{13}$ are alkyl radicals which may be substituted.

The radical $R_2$ may also represent an onium radical of formula

—XP(O)(O—)OCH$_2$CH$_2$N$^+$(CH$_3$)$_3$ where X represents an oxygen atom or a radical —NR$_{14}$, R$_{14}$ representing a hydrogen, a $C_1$–$C_4$ alkyl radical or a hydroxyalkyl radical.

In the context of the invention, $R_2$ may also represent a guanidine radical of formula —X—C=NR$_8$—NR$_9$R$_{10}$, X represents an oxygen atom or a radical —NR$_{11}$, R$_8$, R$_9$, R$_{10}$ and R$_{11}$ representing a hydrogen, a $C_1$–$C_4$ alkyl radical or a hydroxyalkyl radical. According to a particular embodiment, X is —NR$_{11}$, R$_8$ is a hydrogen, R$_9$ and R$_{10}$ are chosen from hydrogen or an alkyl, preferably methyl, radical.

The pKa of the guanidine radical $R_2$ is in general such that this substituent is present in cationic form (=NR$_8$H+) under conventional conditions for oxidation hair dyeing.

In the context of the invention, the counter-ion may be derived from a halogen atom such as bromine, chlorine, fluorine or iodine, a hydroxide, a citrate, a succinate, a tartrate, a lactate, a tosylate, a mesylate, a benzenesulphonate, an acetate, a hydrogen sulphate or a $C_1$–$C_6$ alkyl sulphate such as for example methyl sulphate or ethyl sulphate.

In the context of the present application, cationic tertiary para-phenylenediamines containing a pyrrolidine ring, which are described above and for which $R_2$ is of formula II or III, are preferably used. Still more preferably, the cationic tertiary para-phenylenediamines containing a pyrrolidine ring, which are described above and for which $R_2$ is of formula II or of formula III, with x=0 and for which n=0, are used.

By way of example of derivatives of formula (I), there may be mention:

| Formula | Nomenclature |
|---|---|
| 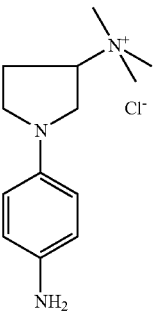 | [1-(4-Aminophenyl)pyrrolidin-3-yl-trimethyl-ammonium chloride (1) |

| Formula | Nomenclature |
|---|---|
| (structure) | [1-(4-Aminophenyl)pyrrolidin-3-yl]dimethyltetradecyl-ammonium bromide (2) |
| (structure) | N'-[1-(4-Aminophenyl)pyrrolidin-3-yl]-N,N-dimethyl guanidinium chloride (3) |
| (structure) | N-[1-(4-Aminophenyl)-pyrrolidin-3-yl]guanidinium chloride (4) |
| (structure) | 3-[1-(4-Aminophenyl)pyrrolidin-3-yl]-1-methyl-3H-imidazole-1-ium chloride (5) |
| (structure) | [1-(4-Aminophenyl)pyrrolidin-3-yl]-(2-hydroxy-ethyl)dimethyl-ammonium chloride (6) |
| (structure) | [1-(4-Aminophenyl)pyrrolidin-3-yl]dimethyl-(3-trimethylsilanyl-propyl)ammonium chloride (7) |
| (structure) | [1-(4-Aminophenyl)pyrrolidin-3-yl]-(trimethyl-ammoniumhexyl)dimethyl-ammonium dichloride (8) |
| (structure) | [1-(4-Aminophenyl)-pyrrolidin-3-yl]oxophosphoryl choline (9) |
| (structure) | {2-[1-(4-Aminophenyl)-pyrrolidin-3-yloxy]-ethyl}-trimethyl-ammonium chloride (10) |
| (structure) | 1-{2-[1-(4-Aminophenyl)pyrrolidin-3-yloxy]ethyl}-1-mehyl-pyrrolidinium; chloride (11) |

-continued

| Formula | Nomenclature |
|---|---|
| (structure) | 3-{3-[1-(4-Aminophenyl)pyrrolidin-3-yloxy]-propyl}-1-methyl-3H-imidazol-1-ium; chloride (12) |
| (structure) | 1-{2-[1-(4-Aminophenyl)pyrrolidin-3-yloxy]ethyl}-1-merhyl piperidinium; chloride (13) |
| (structure) | 3-{3-[1-(5-trimethylsilanyl-ethyl-4-Amino-3-trimethylsilanyl-ethylphenyl)-pyrrolidin-3-yloxy]propyl}-1-methyl-3H-imidazole-1-um; chloride (14) |
| (structure) | [1-(4-Amino-3-methylphenyl)pyrrolidin-3-yl]-trimethylammonium chloride (15) |
| (structure) | [1-(4-Amino-3-methylphenyl)-pyrrolidin-3-yl]dimethyl-tetradecyl-ammonium chloride (16) |

-continued

| Formula | Nomenclature |
|---|---|
| (structure) | N'[1-(4-Amino-3-methylphenyl)-pyrrolidin-3-yl]-N,N-dimethyl guanidinium chloride (17) |
| (structure) | N-[1-(4-Amino-3-methylphenyl)-pyrrolidin-3-yl]-guanidinium chloride (18) |
| (structure) | 3-[1-(4-Amino-3-methylphenyl)-pyrrolidin-3-yl]-1-methyl-3H-imidazole-1-ium chloride (19) |
| (structure) | [1-(4-Amino-3-methylphenyl)-pyrrolidin-3-yl]-(2-hydroxyethyl)-dimethyl-ammonium chloride (20) |
| (structure) | [1-(4-Amino-3-methylphenyl)pyrrolidin-3-yl]-dimethyl(3-trimethylsilanyl-propylammonium chloride (21) |

-continued

| Formula | Nomenclature |
|---|---|
| | [1-(4-Amino-3-methylphenyl)-pyrrolidin-3-yl]-(trimethyl-ammonium-hexyl)dimethyl-ammonium dichloride (22) |
| | [1-(4-Amino-3-methylphenyl)-pyrrolidin-3-yl]-oxophosphorylcholine (23) |
| | {2-[1-(4-Amino-3-methylphenyl)-pyrrolidin-3-yloxy]ethyl}-trimethyl-ammonium chloride (24) |
| | 1-{2-[1-(4-Amino-3-methylphenyl)pyrrolidin-3-yloxy]ethyl}-1-methyl-pyrrolidinium chloride (25) |
| | 3-{3-[1-(4-Amino-3-methylphenyl)-pyrrolidin-3-yloxy]propyl}-1-methyl-3H-imidazole-1-um chloride (26) |

-continued

| Formula | Nomenclature |
|---|---|
| | 1-{2-[1-(4-Amino-3-methylphenyl)pyrrolidin-3-yloxy]ethyl}-1-methylpiperidinium chloride (27) |
| | [1-(4-Amino-3-trimethylsilanyl-ethylphenyl)-pyrrolidin-3-yl]-trimethyl-ammonium chloride (28) |
| | 3-[1-(4-Amino-3-trimethylsilanyl-ethylphenyl)pyrrolidin-3-yl]-1-methyl-3H-imidazole-1-ium chloride (29) |
| | 3-{3-[1-(4-Amino-3-trimethylsilanyl-ethylphenyl)-pyrrolidin-3-yloxy]propyl}-1-methyl-3H-imidazole-1-um chloride (30) |

| Formula | Nomenclature |
|---|---|
| | [1-(5-trimethyl-silanylethyl-4-Amino-3-trimethylsilanyl-ethylphenyl)pyrrolidin-3-yl]-trimethylammonium chloride (31) |
| | 3-[1-(5-trimethylsilanyl-ethyl-4-Amino-3-trimethylethylsilanyl ethylphenyl)-pyrrolidin-3-yl]-1-methyl-3H-imidazole-1-ium chloride (32) |
| | 1'-(4-Aminophenyl)-1-methyl-[1,3']bipyrrolidinyl-1-ium chloride (33) |
| | 1'-(4-Amino-3-methylphenyl)-1-methyl-[1,3']bipyrrolidinyl-1-ium chloride (34) |

| Formula | Nomenclature |
|---|---|
| | 3-{[1-(4-Aminophenyl)pyrrolidin-3-ylcarbamoyl]-methyl}-1-methyl-3H-imidazole-1-ium chloride (35) |
| | 3-{[1-(4-Amino-3-methylphenyl)-pyrrolidin-3-ylcarbamoyl]-methyl}-1-methyl-3H-imidazole-1-ium chloride (36) |
| | 3-[1-(4-Aminophenyl)pyrrolidin-3-yl]-1-(3-trimethylsilanyl-propyl)-3H-imidazole-1-ium chloride (37) |
| | 3-[1-(4-Aminophenyl)pyrrolidin-3-yl]-1-(3-trimethylsilanyl-propyl)-3H-imidazole-1-ium chloride (38) |

-continued

| Formula | Nomenclature |
|---|---|
| 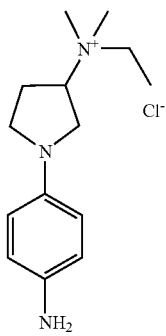 | [1-(4-Aminophenyl)pyrrolidin-3-yl]-ethyldimethyl ammonium chloride (39) |
| | [1-(4-Aminophenyl)pyrrolidin-3-yl]-ethyldimethyl-ammonium iodide (40) |
| | [1-(4-aminophenyl)pyrrolidin-3-yl]-propyldimethyl-ammonium iodide, (41) |
| | [1-(4-Aminophenyl)pyrrolidin-3-yl]-propyldimethyl-ammonium bromide (42) |

-continued

| Formula | Nomenclature |
|---|---|
| | [1-(4-Aminophenyl)pyrrolidin-3-yl]-propyldimethyl-ammonium methosulphate (43) |
| | [1-(4-Aminophenyl)pyrrolidin-3-yl]-butyldimethy;-ammonium iodide (44) |
| | [1-(4-Aminophenyl)pyrrolidin-3-yl]-pentyldimethyl-ammonium iodide (45) |
| | [1-(4-Aminophenyl)pyrrolidin-3-yl]-hexyldimethyl-ammonium iodide (46) |

| Formula | Nomenclature |
|---|---|
| | [1-(4-Aminophenyl)pyrrolidin-3-yl]-heptyldimethyl-ammonium iodide (47) |
| | [1-(4-Aminophenyl)pyrrolidin-3-yl]-octyldimethyl-ammonium iodide (48) |
| | [1-(4-Aminophenyl)pyrrolidin-3-yl]-decyldimethyl ammonium iodide (49) |
| | [1-(4-aminophenyl)pyrrolidin-3-yl]-hexadecyldimethyl-ammonium iodide (50) |
| | [1-(4-Aminophenyl)pyrrolidin-3-yl]-hydroxyethyl-dimethylammonium chloride (51) |
| | [1-(4-aminophenyl)-pyrrolidin-3-yl]-hydroxyethyl-dimethyl-ammonium iodide (52) |

The derivatives of formula I which are preferably used are:

[1-(4-Aminophenyl)pyrrolidin-3-yl]trimethylammonium chloride;

[1-(4-Aminophenyl)pyrrolidin-3-yl]dimethyltetradecyl-ammonium bromide;

N'-[1-(4-Aminophenyl)pyrrolidin-3-yl]-N,N-dimethyl-guanidinium chloride

N-[1-(4-Aminophenyl)pyrrolidin-3-yl]guanidinium chloride

3-[1-(4-Aminophenyl)pyrrolidin-3-yl]-1-methyl-3H-imidazol-1-ium chloride;

[1-(4-Aminophenyl)pyrrolidin-3-yl]-(2-hydroxyethyl)dimethyl-ammonium chloride

[1-(4-Aminophenyl)pyrrolidin-3-yl] dimethyl-(3-trimethylsilanylpropyl)ammonium chloride;

[1-(4-Amino-3-methylphenyl)pyrrolidin-3-yl]trimethyl-ammonium chloride

[1-(4-Amino-3-methylphenyl)pyrrolidin-3-yl]dimethyl-tetradecylammonium chloride

N'-[1-(4-Amino-3-methylphenyl)pyrrolidin-3-yl]-N,N-dimethylguanidinium chloride

N-[1-(4-Amino-3-methylphenyl)pyrrolidin-3-yl]guanidinium chloride

3-[1-(4-Amino-3-methylphenyl)pyrrolidin-3-yl]-1-methyl-3H-imidazol-1-ium chloride

[1-(4-Amino-3-methylphenyl)pyrrolidin-3-yl]-(2-hydroxyethyl)dimethylammonium chloride

[1-(4-Amino-3-methylphenyl)pyrrolidin-3-yl]dimethyl-(3-trimethylsilanylpropylammonium chloride 1'-(4-Aminophenyl)-1-methyl-[1,3']bipyrrolidinyl-1-ium chloride 1'-(4-Amino-3-methylphenyl)-1-methyl-[1,3']bipyrrolidinyl-1-ium chloride 3-{[1-(4-Aminophenyl)pyrrolidin-3-ylcarbamoyl]methyl}-1-methyl-3H-imidazol-1-ium chloride
3-{[1-(4-Amino-3-methylphenyl)pyrrolidin-3-ylcarbamoyl]-methyl}-1-methyl-3H-imidazol-1-ium chloride
3-[1-(4-Aminophenyl)pyrrolidin-3-yl]-1-(3-trimethylsilanylpropyl)-3H-imidazol-1-ium chloride
3-[1-(4-Amino-3-methylphenyl)pyrrolidin-3-yl]-1-(3-trimethylsilanylpropyl)-3H-imidazol-1-ium chloride
[1-(4-aminophenyl)pyrrolidin-3-yl]ethyldimethylammonium chloride
[1-(4-aminophenyl)pyrrolidin-3-yl]-ethyldimethylammonium iodide
[1-(4-aminophenyl)pyrrolidin-3-yl]propyldimethylammonium iodide,
[1-(4-aminophenyl)pyrrolidin-3-yl]propyldimethylammonium bromide
[1-(4-aminophenyl)pyrrolidin-3-yl]propyldimethylammonium methosulphate
[1-(4-aminophenyl)pyrrolidin-3-yl]butyldimethylammonium iodide
[1-(4-aminophenyl)pyrrolidin-3-yl]pentyldimethylammonium iodide
[1-(4-aminophenyl)pyrrolidin-3-yl]hexyldimethylammonium iodide
[1-(4-aminophenyl)pyrrolidin-3-yl]heptyldimethylammonium iodide
[1-(4-aminophenyl)pyrrolidin-3-yl]octyldimethylammonium iodide
[1-(4-aminophenyl)pyrrolidin-3-yl]decyldimethylammonium iodide
[1-(4-aminophenyl)pyrrolidin-3-yl]hexadecyldimethyl-ammonium iodide
[1-(4-aminophenyl)pyrrolidin-3-yl]hydroxyethyldimethylammonium chloride
[1-(4-aminophenyl)pyrrolidin-3-yl]hydroxyethyldimethylammonium iodide.

More preferably, the following compounds will be used:
[1-(4-Aminophenyl)pyrrolidin-3-yl]trimethylammonium chloride
[1-(4-Aminophenyl)pyrrolidin-3-yl]dimethyltetradecyl-ammonium bromide
N'-[1-(4-Aminophenyl)pyrrolidin-3-yl]-N,N-dimethylguanidinium chloride
N-[1-(4-Aminophenyl)pyrrolidin-3-yl]guanidinium chloride
3-[1-(4-Aminophenyl)pyrrolidin-3-yl]-1-methyl-3H-imidazol-1-ium chloride
[1-(4-Aminophenyl)pyrrolidin-3-yl]-(2-hydroxyethyl)dimethylammonium chloride
[1-(4-Aminophenyl)pyrrolidin-3-yl]dimethyl-(3-trimethylsilanylpropyl)ammonium chloride
[1-(4-Aminophenyl)pyrrolidin-3-yl]-(trimethylammoniumhexyl)dimethylammonium dichloride
1'-(4-Aminophenyl)-1-methyl[1,3']bipyrrolidinyl-1-ium chloride
3-[1-(4-Aminophenyl)pyrrolidin-3-yl]-1-(3-trimethylsilanyl-propyl)-3H-imidazol-1-ium chloride
3-[1-(4-Amino-3-methylphenyl)pyrrolidin-3-yl]-1-(3-trimethylsilanylpropyl)-3H-imidazol-1-ium chloride
[1-(4-aminophenyl)pyrrolidin-3-yl]ethyldimethylammonium chloride
[1-(4-aminophenyl)pyrrolidin-3-yl]ethyldimethylammonium iodide
[1-(4-aminophenyl)pyrrolidin-3-yl]propyldimethylammonium iodide,
[1-(4-aminophenyl)pyrrolidin-3-yl]propyldimethylammonium bromide
[1-(4-aminophenyl)pyrrolidin-3-yl]propyldimethylammonium methosulphate
[1-(4-aminophenyl)pyrrolidin-3-yl]butyldimethylammonium iodide
[1-(4-aminophenyl)pyrrolidin-3-yl]pentyldimethylammonium iodide
[1-(4-aminophenyl)pyrrolidin-3-yl]hexyldimethylammonium iodide
[1-(4-aminophenyl)pyrrolidin-3-yl]heptyldimethylammonium iodide
[1-(4-aminophenyl)pyrrolidin-3-yl]octyldimethylammonium iodide
[1-(4-aminophenyl)pyrrolidin-3-yl]decyldimethylammonium iodide
[1-(4-aminophenyl)pyrrolidin-3-yl]hexadecyldimethyl-ammonium iodide
[1-(4-aminophenyl)pyrrolidin-3-yl]hydroxyethyldimethylammonium chloride
[1-(4-aminophenyl)pyrrolidin-3-yl]hydroxyethyldimethylammonium iodide Still more preferably, the following compounds will be used:
[1-(4-Aminophenyl)pyrrolidin-3-yl]trimethylammonium chloride
3-[1-(4-Aminophenyl)pyrrolidin-3-yl]-1-methyl-3H-imidazol-1-ium chloride
[1-(4-Aminophenyl)pyrrolidin-3-yl]-(2-hydroxyethyl)-dimethylammonium chloride.
1'-(4-Aminophenyl)-1-methyl[1,3']bipyrrolidinyl-1-ium chloride, and in particular
[1-(4-Aminophenyl)pyrrolidin-3-yl]trimethylammonium chloride, and
[1-(4-Aminophenyl)pyrrolidin-3-yl]-(2-hydroxyethyl)-dimethylammonium chloride.

The counter-ion is not critical as for the result of the invention, any compounds similar to the preferred compounds described above but with a different counter-ion forms an integral part of the preferred compounds.

The cation tertiary para-phenylenediamine(s) containing a pyrrolidine ring represent from 0.001% to 10%, and preferably from 0.005% to 6% by weight relative to the total weight of the composition.

The compounds of formula (I) may be synthesized according to known methods, and in particular methods described in application WO 02/45675.

The cationic direct dyes comprising a heterocyclic group which may-preferably be used in the compositions according to the present application are heterocyclic dyes chosen from monoazo monocationic direct dyes, polyazo monocationic direct dyes, monoazo polycationic direct dyes and polyazo polycationic direct dyes, these direct dyes being such that the heterocyclic ring bears at least one cationic charge.

Preferably, the composition according to the invention will comprise at least one cationic monoazo dye, and the monoazo dye is preferably monocationic or dicationic. The heterocyclic ring comprises at least one and preferably one or two atoms chosen from O, S and N.

Preferably, the heterocyclic ring of the cationic direct dye is 5- or 6-membered and is optionally fused to an aromatic ring, preferably to a benzene ring.

Even more preferably, the heterocyclic ring contains at least one nitrogen atom.

As cationic direct dyes which may be used in the compositions according to the invention, mention may be made of dicationic diazo dyes, dicationic monoazo dyes and monocationic monoazo dyes.

The dicationic diazo dyes which may be used in the compositions according to the present application are for example:

(A)—the dicationic diazo dyes described in application FR 2822696. The passage in FR 2822696 that is devoted to dicationic diazo dyes and to their synthesis is incorporated by reference into the present application. These dyes correspond to the compounds of general formula Va:

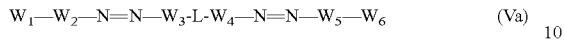

$$W_1-W_2-N=N-W_3-L-W_4-N=N-W_5-W_6 \quad (Va)$$

in which $W_1$ and $W_6$ represent, independently of each other, a radical $NR'_1R'_2$ $W_2$ and $W_5$ represent, independently of each other, a carbon-based aromatic, pyridine or pyridazinyl group of formula (II)

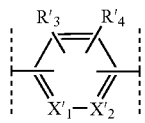

(II)

$W_3$ and $W_4$, represent, independently of each other, a heteroaromatic radical represented by formulae (A) and (B) below:

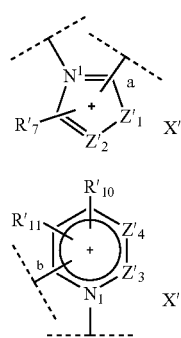

(A)

(B)

in which $X'_1$ represents a nitrogen atom or a radical $CR'_5$,
$X'_2$ represents a nitrogen atom or a radical $CR'_6$,
$Z'_1$ represents an oxygen or sulphur atom or a radical $NR'_8$,
$Z'_2$ represents a nitrogen atom or a radical $CR'_9$,
$Z'_3$ represents a nitrogen atom or a radical $CR'_{12}$,
$Z'_4$ represents a nitrogen atom or a radical $CR'_{13}$,
$N^1$ of the 5-membered ring of formula (A) is linked to the group L and the bond a of the same 5-membered ring is linked to the azo group of formula Va,
the bond b of the 6-membered ring of formula (B) is linked to the azo group of formula (Va) and $N^1$ of the 6-membered ring of formula (B) is linked to the group L,
L, $R'_1$, $R'_2$, $R'_3$, $R'_4$, $R'_5$, $R'_6$, $R'_7$, $R'_9$, $R'_{10}$, $R'_{11}$, $R'_{12}$ and $R'_{13}$ represent, together or independently of each other, a linear or branched $C_1$–$C_{16}$ hydrocarbon-based chain, which can form one or more 3- to 6-membered carbon-based rings, and which may be saturated or unsaturated, one or more carbon atoms of the carbon-based chain of which may be replaced with an oxygen, nitrogen or sulphur atom or with an $SO_2$ group, and the carbon atoms of which may be, independently of each other, substituted with one or more halogen atoms; $R'_1$, $R'_2$, $R'_3$, $R'_4$, $R'_5$, $R'_6$, $R'_7$, $R'_9$, $R'_{10}$, $R'_{11}$, $R'_{12}$ and $R'_{13}$ can represent hydrogen; L, $R'_1$, $R'_2$, $R'_3$, $R'_4$, $R'_5$, $R'_6$, $R'_7$, $R'_9$, $R'_{10}$, $R'_{11}$, $R'_{12}$ and $R'_{13}$ not comprising a peroxide bond or diazo or nitroso radicals, and L is a divalent radical, $R'_8$ represents a linear or branched $C_1$–$C_8$ alkyl radical, optionally substituted with one or more radicals chosen from hydroxyl, $C_1$–$C_2$ alkoxy, $C_2$–$C_4$ (poly)hydroxyalkoxy, amino, $C_1$–$C_2$ di(alkylamino), carboxyl or sulphonic radicals; an optionally substituted phenyl radical, $R'_7$ with $R'_9$, $R'_{10}$ with $R'_{11}$ and $R'_{12}$ with $R'_{13}$ may form a carbon-based aromatic ring, such as a phenyl, X is an organic or mineral anion.

In the context of the definitions of the cationic direct dyes, except where otherwise mentioned, the term "alkyl" means an alkyl radical comprising from 1 to 10 carbon atoms and preferably from 1 to 6 carbon atoms, which may be linear or branched. The term "alkoxy" means alkyl-O—, the term "alkyl" having the above meaning.

According to the invention, when it is indicated that one or more of the carbon atoms of a hydrocarbon-based chain may be replaced with an oxygen, nitrogen or sulphur atom or with an $SO_2$ group, and/or when these hydrocarbon-based chains are unsaturated, this means that it is possible, by way of example, to perform the following transformations:

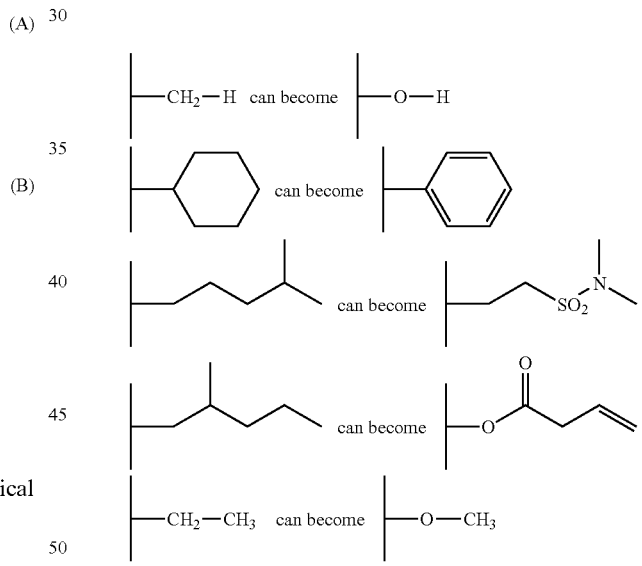

In particular, the experssion "branched hydrocarbon-based chain" means a chain that can form one or more 3- to 6-membered carbon-based rings. The expression "unsaturated hydrocarbon-based chain" means a chain that can comprise one or more double bonds and/or one or more triple bonds, this hydrocarbon-based chain possibly leading to aromatic groups.

X' is an organic or mineral anion chosen, for example, from a halide such as chloride, bromide, fluoride or iodide; a hydroxide; a sulphate; a hydrogen sulphate; a ($C_1$–$C_6$)alkyl sulphate such as for example a methyl sulphate or an ethyl sulphate; an acetate; a tartrate; an oxalate; a ($C_1$–$C_6$)alkylsulphonate such as methylsulphonate; an arylsulphonate which is unsubstituted or substituted with a $C_1$–$C_4$ alkyl radical, such as for example a 4-tolylsulphonate.

(B) the dicationic diazo dyes of general formula (Vb)

$$W_7-N=N-W_8-N=N-W_9 \quad (Vb)$$

in which

W$_7$ and W$_9$ represent independently of each other a heteroaromatic radical represented by formulae (C) and (D) below:

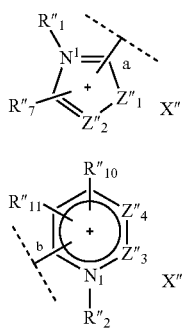

W$_8$ represents a carbon-based aromatic, pyridine or pyridazinyl group of formula (E)

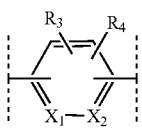

in which formulae (C), (D), (E):

X"$_1$ represents a nitrogen atom or a radical CR"$_5$
X"$_2$ represents a nitrogen atom or a radical CR"$_6$
Z"$_1$ represents an oxygen or sulphur atom or a radical NR"$_8$,
Z"$_2$ represents a nitrogen atom or a radical CR"$_9$,
Z"$_3$ represents a nitrogen atom or a radical CR"$_{12}$,
Z"$_4$ represents a nitrogen atom or a radical CR"$_{13}$,
the bond a of the 5-membered cationic ring of formula (C) is linked to the azo group of formula (Vb),
the bond b of the 6-membered cationic ring of formula (D) is linked to the azo group of formula (Vb)
R"$_3$, R"$_4$, R"$_5$, R"$_6$, R"$_7$, R"$_9$, R"$_{10}$, R"$_{11}$, R"$_{12}$ and R"$_{13}$, represent, together or independently of each other, a hydrogen atom, a linear or branched, saturated or unsaturated C$_1$–C$_{16}$ hydrocarbon-based chain, which can form one or more 3- to 6-membered carbon-based rings, one or more carbon atoms of the carbon-based chain of which may be replaced with an oxygen, nitrogen or sulphur atom or with an SO$_2$ group, and the carbon atoms of which may be, independently of each other, substituted with one or more halogen atoms; R"$_3$, R"$_4$, R"$_5$, R"$_6$, R"$_7$, R"$_9$, R"$_{10}$, R"$_{11}$, R"$_{12}$ and R"$_{13}$ not comprising a peroxide bond or diazo or nitroso radicals,
R"$_7$ with R"$_9$, R"$_{10}$ with R"$_{11}$ and R"$_{12}$ with R"$_{13}$ can form a carbon-based aromatic ring, such as a phenyl,
X" is an organic or mineral anion chosen for example from a halide such as chloride, bromide, fluoride or iodide; a hydroxide; a sulphate; a hydrogen sulphate; a (C$_1$–C$_6$)alkyl sulphate such as for example a methyl sulphate or an ethyl sulphate; an acetate; a tartrate; an oxalate; a (C$_1$–C$_6$)alkylsulphonate such as methylsulphonate; an arylsulphonate which is unsubstituted or substituted with a C$_1$–C$_4$ alkyl radical such as for example a 4-tolylsulphonate.

R"$_3$, R"$_4$, R"$_5$, R"$_6$, R"$_{10}$, R"$_{11}$, R"$_{12}$ and R"$_{13}$, represent, preferably and independently of each other, a hydrogen atom; a linear or branched C$_1$–C$_4$ alkyl radical, optionally substituted with one or more radicals chosen from hydroxyl, C$_1$–C$_2$ alkoxy, C$_2$–C$_4$ (poly)hydroxyalkoxy, amino, C$_1$–C$_2$ (di)alkylamino, carboxyl or sulphonic radicals; a phenyl radical optionally substituted with one or more radicals chosen from hydroxyl, C$_1$–C$_2$ alkoxy, C$_2$–C$_4$ (poly)hydroxyalkoxy, amino, C$_1$–C$_2$ (di)alkylamino, carboxyl or sulphonic radicals or a halogen atom such as chlorine, fluorine or bromine; a carboxyl radical; a sulphonylamino radical; a sulphonic radical; a C$_1$–C$_2$ alkoxy radical; a C$_2$–C$_4$ (poly)hydroxyalkoxy radical; an amino radical; a C$_1$–C$_2$ (di)alkylamino radical; a C$_2$–C$_4$ (poly)hydroxyalkylamino radical.

More preferably, R"$_3$, R"$_4$, R"$_5$, R"$_6$, R"$_{10}$, R"$_{11}$, R"$_{12}$ and R"$_{13}$ represent a hydrogen atom, a C$_1$–C$_4$ alkyl radical optionally substituted with one or more radicals chosen from hydroxyl, amino and C$_1$–C$_2$ (di)alkylamino radicals; a carboxyl radical; a C$_1$–C$_2$ alkoxy radical; an amino radical; a C$_1$–C$_2$ (di)alkylamino radical; a C$_2$–C$_4$ (poly)hydroxyalkylamino radical.

According to one particularly preferred embodiment, R"$_3$, R"$_4$, R"$_5$, R"$_6$, R"$_{10}$, R"$_{11}$, R"$_{12}$ and R"$_{13}$ represent a hydrogen atom, a methyl, phenyl or 2-hydroxymethyl radical, a carboxyl, a methoxy, ethoxy or 2-hydroxyethyloxy radical, an amino, methylamino, dimethylamino or 2-hydroxyethylamino radical.

R"$_7$ and R"$_9$ represent, independently of each other, a hydrogen atom; a linear or branched C$_1$–C$_4$ alkyl radical, optionally substituted with one or more radicals chosen from hydroxyl, C$_1$–C$_2$ alkoxy, C$_2$–C$_4$ (poly)hydroxyalkoxy, amino, C$_1$–C$_2$ (di)alkylamino, carboxyl or sulphonic radicals; an optionally substituted phenyl radical; a carboxyl radical; a sulphonylamino radical.

Among these substituents, R"$_7$ and R"$_9$ preferably represent a hydrogen atom, a phenyl radical, a C$_1$–C$_4$ alkyl radical optionally substituted with one or more radicals chosen from hydroxyl, amino, C$_1$–C$_2$ (di)alkylamino or carboxyl radicals.

According to one particularly preferred embodiment, R"$_7$ and R"$_9$ preferably represent a hydrogen atom, a methyl, phenyl or 2-hydroxymethyl radical or a carboxyl.

R"$_1$, R"$_2$ and R"$_8$ represent a linear or branched C$_1$–C$_8$ alkyl radical optionally substituted with one or more radicals chosen from hydroxyl, C$_1$–C$_2$ alkoxy, C$_2$–C$_4$ (poly)hydroxyalkoxy, amino, C$_1$–C$_2$ (di)alkylamino, carboxyl or sulphonic radicals; an optionally substituted phenyl radical.

Among these substituents, R"$_1$, R"$_2$ and R"$_8$ preferably represent a C$_1$–C$_4$ alkyl radical optionally substituted with one or more radicals chosen from hydroxyl, C$_1$–C$_2$ alkoxy, amino, C$_1$–C$_2$ (di)alkylamino, carboxyl or sulphonic radicals.

According to one particularly preferred embodiment, R"$_1$, R"$_2$ and R"$_8$ preferably represent a methyl, ethyl, 2-hydroxyethyl, 1-carboxymethyl, 2-carboxyethyl or 2-sulphonylethyl radical.

W$_7$ and W$_9$ preferably represent, independently of each other, a cationic imidazolium, triazolium, thiazolium or pyridinium group substituted with the preferred radicals R"$_1$, R"$_7$ R"$_{10}$, R"$_{11}$, R"$_{12}$ and R"$_{13}$.

W$_8$ preferably represents a phenyl or pyridyl group substituted with the preferred radicals R"$_3$, R"$_4$ R"$_5$ and R"$_6$.

Among the diazo dicationic dyes of formula (Vb), mention may be made especially of the following compounds:
1,3-dimethyl-2-[4-(1,3-dimethyl(imidazol-1-ium)-2-ylazo)-phenylazo]imidazol-1-ium.

1,4-dimethyl-3-[4-(1,4-dimethyl(triazol-2-ium)-3-ylazo)-phenylazo]triazol-2-ium.
1-methyl-2-[4-(1-methyl(pyridin-1-ium)-2-ylazo)phenylazo]-pyridin-1-ium.
1-methyl-3-[4-(1-methyl(pyridin-1-ium)-3-ylazo)phenylazo]-pyridin-1-ium.
1,3-dimethyl-2-[4-(3-methyl(thiazol-3-ium)-2-ylazo)-phenylazo]imidazol-1-ium.
1,4-dimethyl-3-[4-(3-methyl(thiazol-3-ium)-2-ylazo)-phenylazo]triazol-2-ium.
1,3-dimethyl-2-[4-(1,4-dimethyl(triazol-2-ium)-3-ylazo)-phenylazo]imidazol-1-ium.
1-methyl-2-[4-(3-methyl(thiazol-3-ium)-2-ylazo)phenylazo]-pyridin-1-ium.
1-methyl-3-[4-(3-methyl(thiazol-3-ium)-2-ylazo)phenylazo]-pyridin-1-ium.
1,3-dimethyl-2-[4-(1-methyl(pyridin-1-ium)-2-ylazo)-phenylazo]imidazol-1-ium.
1,4-dimethyl-3-[4-(1-methyl(pyridin-1-ium)-2-ylazo)-phenylazo]triazol-2-ium.
1,3-dimethyl-2-[4-(1-(2-hydroxyethyl)(pyridin-1-ium)-2-ylazo)phenylazo]imidazol-1-ium.
1,4-dimethyl-3-[4-(1-(2-hydroxyethyl)(pyridin-1-ium)-2-ylazo)phenylazo]triazol-2-ium.
1,3-dimethyl-2-[4-(1-methyl(pyridin-1-ium)-3-ylazo)-phenylazo]imidazol-1-ium.
1,4-dimethyl-3-[4-(1-methyl(pyridin-1-ium)-3-ylazo)-phenylazo]triazol-2-ium.
1,3-dimethyl-2-[4-(1-(2-hydroxyethyl)(pyridin-1-ium)-3-ylazo)phenylazo]imidazol-1-ium.
1,4-dimethyl-3-[4-(1-(2-hydroxyethyl)(pyridin-1-ium)-3-ylazo)phenylazo]triazol-2-ium.
1,3-dimethyl-2-[4-(1,3-dimethyl(imidazol-1-ium)-2-ylazo)-3-methoxyphenylazo]imidazol-1-ium.
1,3-dimethyl-2-[4-(1,4-dimethyl(triazol-2-ium)-3-ylazo)-3-methoxyphenylazo] imidazol-1-ium.
1,3-dimethyl-2-[4-(1-methyl(pyridin-1-ium)-2-ylazo)-3-methoxyphenylazo]imidazol-1-ium.

The methods for obtaining the compounds of formula (Vb) are based on reactions that are already well known in the literature and related, for example, in the following documents: U.S. Pat. No. 3,291,788, GB-1 186 753, U.S. Pat. No. 3,271,383, EP-0 757 083 and U.S. Pat. No. 5,708, 151.

(C) The dicationic direct dyes of formula (Vc), (Vd) or (Ve) below:

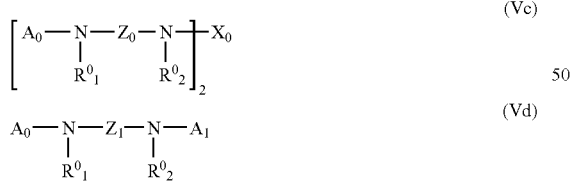

(Vc)

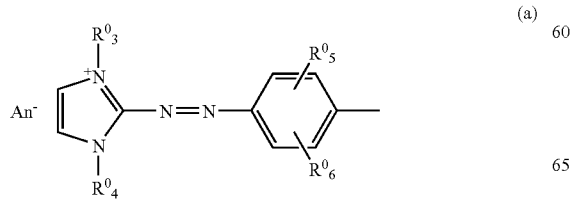

(Vd)

in which formula (Vc) or (Vd):
$A_0$ and $A_1$, independently of each other, denote a radical of formula (a) below (a)

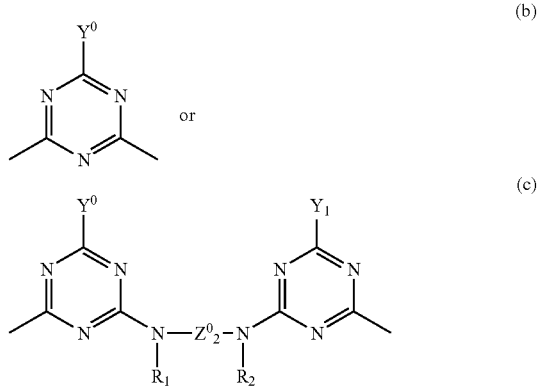

$Z_0$ denotes an apliphatic or aromatic radical,
$Z_1$ denotes an alkyl radical,
$R^O_1$ and $R^O_2$, independently of each other, denote a hydrogen atom, or a $(C_1-C_4)$alkyl radical or a $(C_1-C_4)$alkyl radical substituted with one or more halogen atoms, a hydroxyl, carboxyl or cyano radical, a $(C_1-C_4)$alkoxy radical, a $(C_1-C_4)$alkoxy radical substituted with one or more hydroxyl or $(C_1-C_4)$alkoxy radicals, an amino, alkylamino, dialkylamino, aminocarbonyl, phenyl, phenoxy or phenylaminocarbonyl radical, in which the phenyl radical is unsubstituted or substituted with a $(C_1-C_4)$alkyl, $(C_1-C_4)$alkoxy or phenoxy radical,
or alternatively $R^O_1$ and $R^O_2$ form, together with the two nitrogen atoms which bear them and the radical $Z_0$, a piperazine ring,
$X_0$ is a bridging radical chosen from: —CO—; —CO—CH$_2$—CH$_2$—CO—; —CO—CO—; 1,4-dicarbonylphenyl; —CH$_2$—CH$_2$—; or a triazine of formula (b) or (c) below:

(b)

(c)

in which:
$Y_0$ and $Y_1$, independently of each other, denote a halogen atom, or a hydroxyl, amino, monoalkylamino, dialkylamino, piperidino, morpholino or 1-piperazino radical, the piperazino radical being unsubstituted or substituted on the nitrogen atom not attached to the triazine ring with a $(C_1-C_4)$alkyl radical, the said alkyl radicals being unsubstituted or substituted with hydroxyl, amino, mono-$(C_1-C_4)$alkylamino or di-$(C_1-C_4)$alkylamino,
$Z^O_2$ denotes a $(C_2-C_8)$alkylene radical or forms, with the two adjacent nitrogen atoms and the radicals $R_1$ and $R_2$, a piperazine ring,
in the radical of formula (a),
$R^O_3$ and $R^O_4$, independently of each other, denote a hydrogen atom, or a $(C_1-C_4)$alkyl radical, a $(C_1-C_4)$alkyl radical substituted with one or more halogen atoms, a hydroxyl, carboxyl or cyano radical, a $(C_1-C_4)$alkoxy radical, a $(C_1-C_4)$alkoxy radical substituted with a hydroxyl or $(C_1-C_4)$alkoxy radical, an amino, alkylamino, dialkylamino, aminocarbonyl, phenyl, phenoxy or phenylaminocarbonyl radical, in which the phenyl radical is unsubstituted or substituted with a $(C_1-C_4)$alkyl, $(C_1-C_4)$alkoxy or phenoxy radical,
$R^O_5$ and $R^O_6$, independently of each other, denote a hydrogen atom, a $(C_1-C_4)$alkyl or $(C_1-C_4)$alkoxy radical optionally substituted with a hydroxyl, carboxyl, halogen or cyano radical, $(C_1-C_4)$alkoxy optionally substituted with a hydroxyl or $(C_1-C_4)$alkoxy radical, an amino, alkylamino, dialkylamino, aminocarbonyl, phenyl, phenoxy or phenylaminocarbonyl radical, in which the phenyl radical is unsubstituted or substituted with a ($C_1$–$C_4$)alkyl, ($C_1$–$C_4$)alkoxy or phenoxy radical, An⁻ denotes an anion.

Preferably, according to the invention, in formula (Vc), $R^o{}_1$ and $R^o{}_2$ independently of each other, denote hydrogen, ($C_1$–$C_4$)alkyl substituted with hydroxyl or ($C_1$–$C_4$) alkoxy, and even more particularly denote hydrogen or methyl, $Z_0$ denotes a linear, branched or cyclic $C_2$–$C_8$ alkyl radical, optionally substituted with a hydroxyl, alkoxy or halogen, the chain of the said radical being optionally interrupted with a group —O— or —$NR_1$—; a 1,4-phenyl radical, a 1,4-naphthyl radical optionally substituted with an alkyl, alkoxy or halogen; Z possibly forming a piperazine ring with $R_1$, $R_2$ and the 2 nitrogen atoms, $Z_0$ preferably denotes an unsubstituted phenyl radical, a phenyl or naphthyl radical substituted with one or two methyl or methoxy radicals, a piperazine radical via bonding with $R_1$, $R_2$ and the 2 nitrogen atoms, or a ($C_2$–$C_4$)alkylene radical which is unsubstituted or substituted with one or 2 hydroxyls, $X_0$ denotes a group of formula (b).

Preferably, according to the invention, in formula (Vd),

Z1 denotes a linear, branched or cyclic $C_2$–$C_8$ alkyl radical, optionally substituted with a hydroxyl, alkoxy or halogen atom, the chain of the said radical being optionally interrupted with a group —O— or —$NR_1$—; a piperazine ring formed with $R_1$, $R_2$ and the two nitrogen atoms, $Z_1$ preferably denotes a ($C_2$–$C_6$)alkylene radical which is unsubstituted or substituted with one or more hydroxyls, a piperazine ring formed with $R_1$, $R_2$ and the two nitrogen atoms; and even more particularly an unsubstituted ($C_2$–$C_4$)alkylene radical, $R^o{}_3$ and $R^o{}_4$ denote methyl or ethyl, and $R^o{}_5$ and $R^o{}_6$ denote hydrogen, methyl or methoxy.

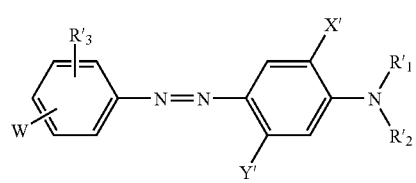

(Ve)

in which formula (Ve), the number of cationic charges is two,

X' and Y', independently of each other, denote hydrogen, halogen, ($C_1$–$C_4$)alkyl, ($C_1$–$C_4$)alkoxy, ($C_1$–$C_4$)alkylcarbonylamino, arylcarbonylamino, ureido or arylureido, $R'_1$ denotes hydrogen, a substituted alkyl or aryl radical, an unsubstituted alkyl or aryl radical, or has the same meaning as $R'_2$ $R'_2$ is a radical of formula (d) below:

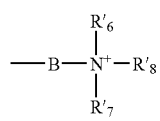

(d)

in which:

B denotes a linear or branched alkylene radical, $R'_6$ denotes hydrogen or substituted or unsubstituted alkyl, $R'_7$ and $R'_8$, independently of each other, denote substituted or unsubstituted alkyl, $R'_6$ and $R'_7$, together with the nitrogen, form a substituted or unsubstituted 5-, 6- or 7-membered ring, which may contain other heteroatoms, or alternatively $R'_6$ and $R'_7$ and $R'_8$ together form a pyridinium ring, $R'_3$ denotes hydrogen, halogen, ($C_1$–$C_4$)alkyl or ($C_1$–$C_4$) alkoxy, W is a radical of formula (e) below:

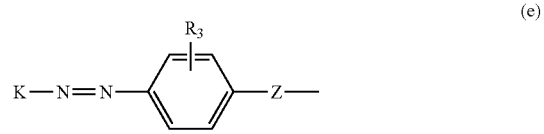

(e)

in which:

K is a coupling radical,

Z denotes a bridging radical chosen from the radicals of formulae:

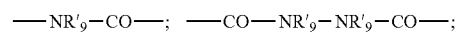

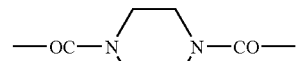

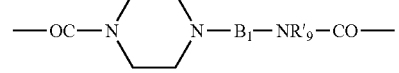

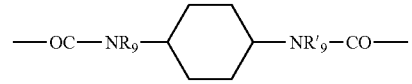

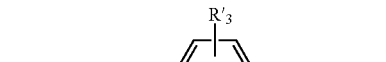

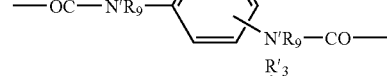

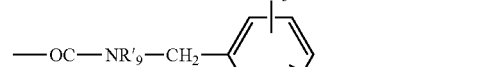

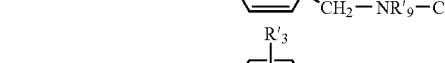

or alternatively

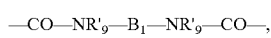

and in which $R'_9$ denotes hydrogen, substituted or unsubstituted ($C_2$–$C_4$)alkylene, the alkylene radical being linear or branched and possibly being interrupted with one or more groups chosen from: —$NR'_9$—, —O—, —S—.

Preferably, according to the invention, in formula (III),

B denotes ethylene, n-propylene, isopropylene or n-butylene,

K denotes a coupling compound chosen from those of formula (f), (g) or (h) below:

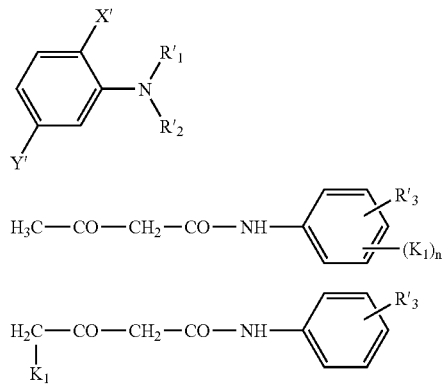

in which,

X', Y' and R'$_1$, and R'$_2$ have the same meaning as in formula (III), n is equal to 1 or 2, K$_1$ denotes the radical of formula:

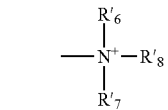

Among the compounds of formula (Vc), mention may be made more particularly of the compound having the following structure:

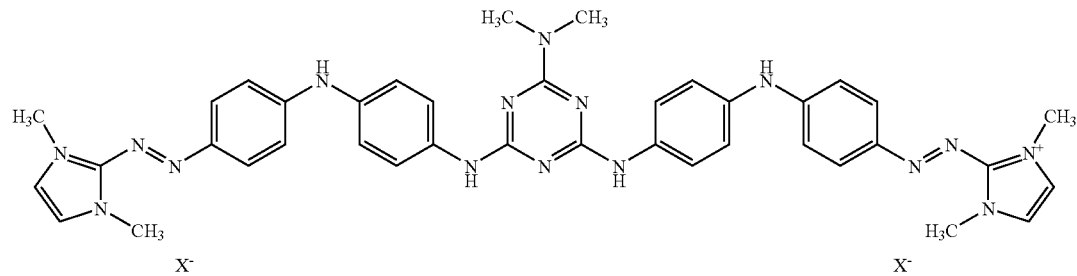

Mention may also be made of the compounds having the following formulae:

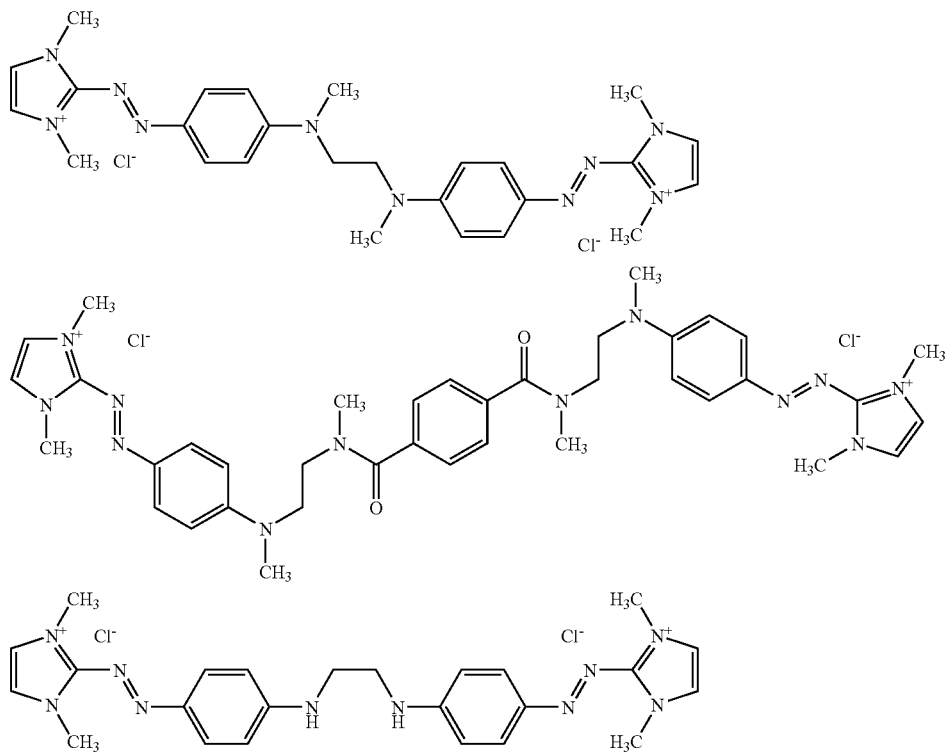

-continued

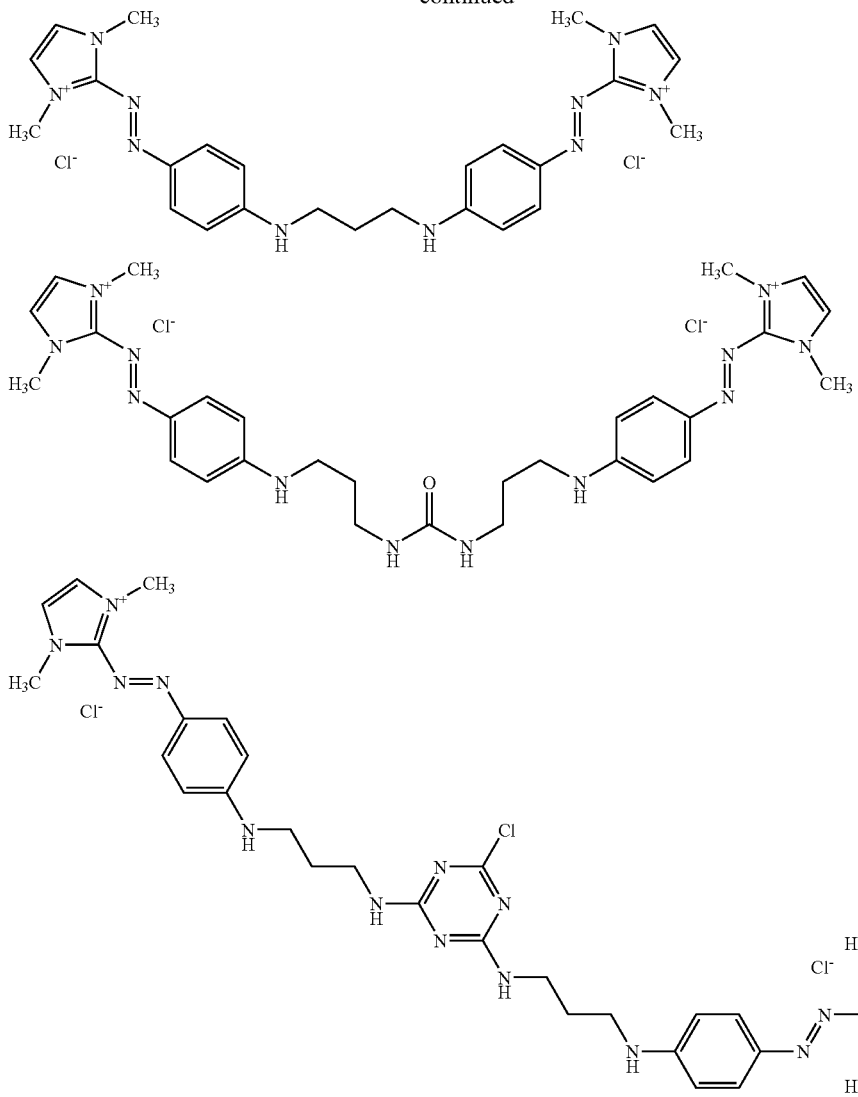

Among the compounds of formula (Ve), mention may be made more particularly of the compound having the following structure:

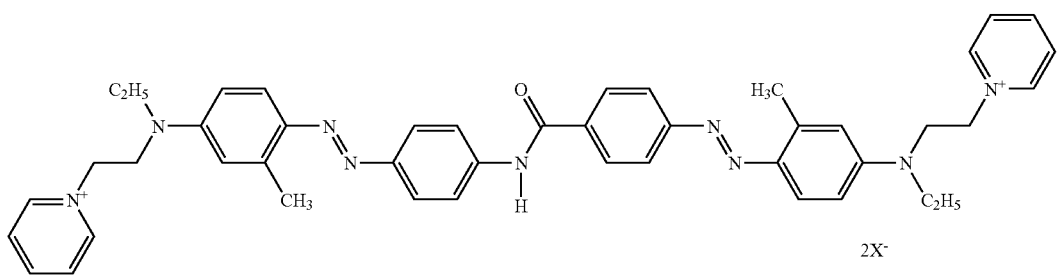

The dyes of formulae (Vc), (Vd) and (Ve) are known per se, and are described and prepared in patents U.S. Pat. No. 5,674,299 or U.S. Pat. No. 5,708,151.

The dicationic monazo dyes that may be used in the compositions according to the present application are for example those described in application FR 2822698. The passage in FR 2822698 which is devoted to dicationic monoazo dyes and to their synthesis is incorporated by reference in the present application.

These dyes correspond to the compounds of general formulae (Vf) and (Vg) below:

  (Vf)

  (Vg)

in which formulae
n is equal to 0 or 1,
$Z_1$ represents a 5- or 6-membered cationic heteroaromatic radical of formula (III) or (IV):

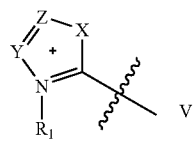  (III)

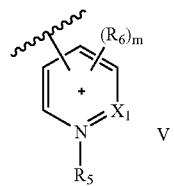  (IV)

in which
X represents $NR_3$, S or O, Z represents $CR_2$ or N and Y represents $CR_4$ or N with the following conditions:
when X is $NR_3$ or O and Z is $CR_2$, then Y is $CR_4$ or N,
when X is S, then Z is N or Y is N
when X is S and Z is N, then Y is $CR_4$
$X_1$ represents $CR_6$ or N,
m is an integer equal to 0, 1, 2 or 3,
$R_1$, $R_3$ and $R_5$ represent, independently of each other, a saturated or unsaturated, linear or branched $C_1$–$C_{10}$ hydrocarbon-based chain which can form an optionally aromatic, 5- to 7-membered carbon-based ring; one or more carbon atoms possibly being replaced with an oxygen, nitrogen, halogen or sulphur atom or with an $SO_2$ group, with the exception of the carbon linked to the nitrogen atom of the ring of formula (III) or (IV); the radicals $R_1$, $R_3$ or $R_5$ not comprising a peroxide bond or diazo, nitro or nitroso radicals;
$R_2$, $R_4$ and $R_6$ represent, independently of each other, a hydrogen atom; a saturated or unsaturated, linear or branched $C_1$–$C_{10}$ hydrocarbon-based chain which can form an optionally aromatic, 5- to 7-membered carbon-based ring; one or more carbon atoms possibly being replaced with one or more oxygen, nitrogen or sulphur atoms, or with an $SO_2$ group; the radicals $R_2$, $R_4$ or $R_6$ not comprising a peroxide bond or diazo, nitro or nitroso radicals; the radicals $R_2$ and $R_4$ can together form a carbon-based aromatic ring,
V represents an organic or mineral anion,
$A_1$ and $A_3$ represent, independently of each other, a divalent radical of formula (V) or (VI)

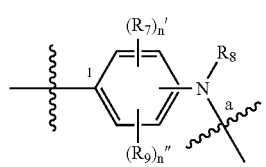  (V)

-continued

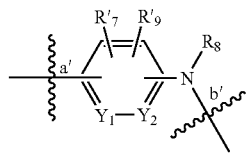  (VI)

in which
n' is an integer equal to 0, 1, 2 or 3,
n" is an integer equal to 0 or 1,
$Y_1$–$Y_2$ represents C—N or N—N,
when n=0, then the bond a of the group $A_1$ of formula (V) is linked to the function $Z_2$ of formula (Vf), or
when n=0, then the bond b' of the group A1 of formula (VI) is linked to the function $Z_2$ of formula (Vf),
when n=1, then the bond a of the group $A_1$ of formula (V) is linked to $C_1$ of the group $A_3$ of formula (V), the bond a of the group $A_3$ of formula (V) being linked to the function $Z_2$ of formula (Vf), or
when n=1, then the bond a of the group $A_1$ of formula (V) is linked to the carbon bearing the bond a' of the group $A_3$ of formula (VI), the bond b' being linked to the function $Z_2$ of formula (Vf),
when n=1, then the bond b' of the group $A_1$ of formula (VI) is linked to the carbon $C_1$ of the group $A_3$ of formula (V), the bond a being linked to the function $Z_2$ of formula (Vf), or
when n=1, then the bond b' of the group $A_1$ of formula (VI) is linked to the carbon bearing the bond a' of the group $A_3$ of formula (VI), the bond b' of the group $A_3$ of formula (VI) being linked to the function $Z_2$ of formula (Vf),
$R_8$ and $R'_8$ represent, independently of each other, a non-cationic group chosen from a hydrogen atom, a linear or branched $C_1$–$C_{10}$ hydrocarbon-based chain which can form an optionally aromatic 5- to 7-membered carbon-based ring; one or more carbon atoms of the hydrocarbon-based chain possibly being replaced with one or more oxygen, nitrogen or sulphur atoms or with an $SO_2$ group, with the exception of the carbon linked to the nitrogen atom; the radicals $R_8$ or $R'_8$ not comprising a peroxide bond or diazo, nitro or nitroso radicals;
$R_7$, $R_9$, $R'_7$ and $R'_9$ represent, independently of each other, a non-cationic group as defined for $R_2$ or a cationic group $Z_3$, with the condition that only one of the groups $R_7$, $R_9$, $R'_7$ and $R'_9$ is cationic
$R_7$ with $R_8$, or $R'_7$ with $R'_8$, can together form a saturated 5- or 6-membered heterocycle,
$Z_3$ is a cationic group represented by formula (VII) below

  (VII)

in which:
B represents a linear or branched hydrocarbon-based chain containing from 1 to 15 carbon atoms, which can form one or more optionally aromatic 3- to 7-membered rings, and one or more carbon atoms of which may be replaced with an oxygen, nitrogen or sulphur atom or with an $SO_2$ radical, with the exception of the carbon linked to the nitrogen atom; B not comprising a peroxide bond or diazo, nitro or nitroso radicals,
the radical B is linked to D via any of the atoms of the radical D,
n''' can take the value 0 or 1, 1) D is chosen from the cationic groups of formulae (VIII) and (IX) below:

$$\text{(VIII)}$$

[Structure showing ring with $T_1, T_2, T_3, p(T_4), T_5, T_6$, N, and V']

$$\text{(IX)}$$

$$R13-\overset{R12}{\underset{R10}{N^+}}-R11 \quad V'$$

in which:
p can take the value 0 or 1;
$T_1, T_2, T_3$ and $T_4$, independently of each other, represent an oxygen atom; a sulphur atom; a nitrogen atom which is unsubstituted or substituted with a radical $R_{14}$; or a carbon atom which is unsubstituted or substituted with one or two radicals $R_{14}$, which may be identical or different;
$T_5$ represents a nitrogen atom; or a carbon atom which is unsubstituted or substituted with a radical $R_{14}$;
$T_6$ can take the same meanings as those given below for the radical $R_{14}$, it being understood that $T_6$ is other than a hydrogen atom;
$T_1$ or $T_5$ can also form with $T_6$ a saturated or unsaturated 5- to 7-membered ring, each ring member being unsubstituted or substituted with one or two radicals $R_{14}$, which may be identical or different;
two of the adjacent radicals $T_1, T_2, T_3, T_4$ and $T_5$ can also form a 5- to 7-membered ring, each ring member being independently represented by a carbon atom which is unsubstituted or substituted with one or two radicals $R_{14}$, which may be identical or different, a nitrogen atom which is unsubstituted or substituted with a radical $R_{14}$, an oxygen atom or a sulphur atom;
$R_{10}, R_{11}, R_{12}, R_{13}$ and $R_{14}$, which may be identical or different, represent a hydrogen atom; a linear or branched, optionally aromatic hydrocarbon-based chain containing from 1 to 10 carbon atoms, and one or more carbon atoms of which may be replaced with an oxygen, nitrogen or sulphur atom or with an $SO_2$ group, and one or more carbon atoms of which may, independently of each other, be substituted with one or more halogen atoms; the said radical not comprising a peroxide bond or diazo, nitro or nitroso radicals;
$R_{10}, R_{11}$ and $R_{12}$ can also form, in pairs, with the quaternary nitrogen atom to which they are attached, one or more saturated 5- to 7-membered rings, each ring member being independently represented by a carbon atom which is unsubstituted or substituted with one or two radicals $R_{14}$, which may be identical or different, a nitrogen atom, which is unsubstituted or substituted with a radical $R_{14}$, an oxygen atom or a sulphur atom,
when n'''=0, then the group of formula (IX) may be linked to the compound of formulae (V) and (VI) directly via the nitrogen atom of the quaternary ammonium, $R_{13}$ in this case representing a single bond,
V' represents an organic or mineral anion,
$Z_2$ represents a linear or branched $C_1$–$C_{10}$ hydrocarbon-based chain which can form an optionally aromatic 5- to 7-membered carbon-based ring; one or more carbon atoms possibly being replaced with one or more oxygen, nitrogen or sulphur atoms or with an $SO_2$ group, the said radical $Z_2$ not comprising a peroxide bond or diazo, nitro or nitroso radicals; a cationic group $Z_3$ as defined above,
with the proviso that $Z_2$ is not cationic when $R_7, R_9, R_7'$ or $R_9'$ is cationic,
$A_2$ represents a radical of formula (X) corresponding to a carbon-based aromatic, pyridine or pyridazine radical substituted with a 5-membered cationic heteroaromatic radical, optionally substituted with one or more radicals $R_{19}$ of the same definition as $R_2$; a radical of formula (XI):

$$\text{(X)}$$

[Structure showing ring with $(R_{21})_t$, $Y_3=Y_4$, 5-membered ring with N, $(R_{19})_s$, V'']

$$\text{(XI)}$$

[Structure showing ring with X, $R_{16}$, $R_{17}$, $R_{15}$, $(R_{19})_q$, V'']

in which
r is an integer equal to 0 or 1,
q is an integer equal to 0, 1, 2 or 3,
s is an integer equal to 0, 1, 2, 3, 4 or 5,
t is an integer equal to 0, 1 or 2.
$Y_3=Y_4$ represents C=C, C=N or N=N,
if r=0, then X represents O, S, $NR_{18}$ or $CR_{20}$,
if r=1, then X represents $CR_{20}$,
$R_{15}$ and $R_{18}$ have the same definition as $R_1$ defined above,
$R_{16}, R_{17}, R_{19}, R_{20}$ and $R_{21}$ have the same definition as $R_2$ defined above,
V'' represents an organic or mineral anion,
with the condition that in formula (Vf) one of the groups $A_1, Z_2$ and $A_3$ is a cationic group.

The monocationic monoazo dyes which may be used in the compositions according to the present application are for example:
(A) the monocationic monoazo dyes described in application WO 02-078659, the passage of this application devoted to monocationic monoazo dyes and to their synthesis is incorporated by reference in the present application.

These dyes correspond to the compounds of general formula (Vh)

$$W_1-N=N-W_2-W_3$$

in which
$W_1$ represents a 5-membered cationic aromatic heterocycle of formula (II) below formula (II)

[Structure showing $R_9$, $N^1$, $R_{10}$, $Z_1'$, $Z_2'$, X, a]

$W_2$ represents a divalent carbon-based aromatic or pyridine group of formula (III) or (IV) below

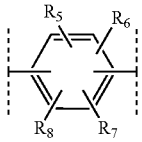

formula (III)

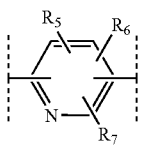

formula (IV)

$W_3$ represents a 5- or 6-membered heterocycle of formula (V) below

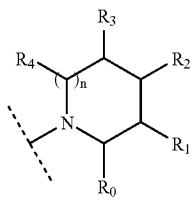

formula (V)

in which formulae $Z_1$ represents an oxygen or sulphur atom or a radical $NR_{12}$, $Z_2$ represents a nitrogen atom or a radical $CR_{11}$, $R_9$ and $R_{12}$ represent, independently of each other, a $C_1$–$C_8$ alkyl radical, optionally substituted with one or more radicals chosen from a hydroxyl, a $C_1$–$C_2$ alkoxy, a $C_2$–$C_4$ (poly)hydroxyalkoxy radical, an amino, a $C_1$–$C_2$ (di)alkylamino, a carboxyl or a sulphonic radical; an optionally substituted phenyl radical, $R_{10}$ and $R_{11}$ represent, independently of each other, a hydrogen atom; a $C_1$–$C_4$ alkyl radical, optionally substituted with one or more radicals chosen from a hydroxyl, a $C_1$–$C_2$ alkoxy, a $C_2$–$C_4$ (poly)hydroxyalkoxy, an amino, a $C_1$–$C_2$ (di)alkylamino, a carboxyl or a sulphonic radical; an optionally substituted phenyl radical; a carboxyl radical; a sulphonylamino radical;

$R_5$, $R_6$, $R_7$ and $R_8$ represent, independently of each other, a hydrogen atom; a chlorine atom; a bromine atom; a linear or branched $C_1$–$C_6$ hydrocarbon-based chain, which can form one or more 3- to 6-membered carbon-based rings, and which may be saturated or unsaturated, one or more carbon atoms of the carbon-based chain of which may be replaced with an oxygen, nitrogen or sulphur atom or with an $SO_2$ group, and the carbon atoms of which may, independently of each other, be substituted with one or more halogen atoms; $R_5$, $R_6$, $R_7$ and $R_8$ not comprising a peroxide bond or diazo or nitroso radicals, n is an integer equal to 0 or 1, $R_0$, $R_1$, $R_2$, $R_3$ and $R_4$ represent, independently of each other, a hydrogen atom, a hydroxyl radical; amino; acetoxy; a group —$NR_{13}R_{14}$, $R_{13}$ and $R_{14}$ representing, independently of each other, a hydrogen atom, a $C_1$–$C_4$ alkyl radical substituted with one or more radicals chosen from a halogen atom, a hydroxyl, $C_1$–$C_2$ alkoxy, amino or $C_1$–$C_2$ amino(di)alkyl radical; a sulphonylamino radical; a carboxyl radical; a carboxamido radical; an amido radical; a mono- or dialkylamido radical; a halogen; a $C_1$–$C_6$ alkyl radical substituted with one or more radicals chosen from a hydroxyl, $C_1$–$C_2$ alkoxy, $C_2$–$C_4$ (poly)hydroxyalkoxy, amino or $C_1$–$C_2$ (di)alkylamino radical, it being understood that at least one of the groups $R_0$, $R_1$, $R_2$, $R_3$ and $R_4$ is other than hydrogen, X is an organic or mineral anion.

(B) The monocationic monoazo dyes described in application WO 02-078658, the passage in this application devoted to monocationic monoazo dyes and to their synthesis is incorporated by reference in the present application.

These dyes correspond to the compounds of general formula (Vi)

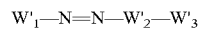

in which $W'_1$ represents a 5-membered cationic aromatic heterocycle of formula (II') below

formula (II')

$W'_2$ represents a divalent carbon-based aromatic or pyridine group of formula (III') or (IV') below

(III')

(IV')

$W'_3$ represents a 7- or 8-membered heterocycle of formula (V') below

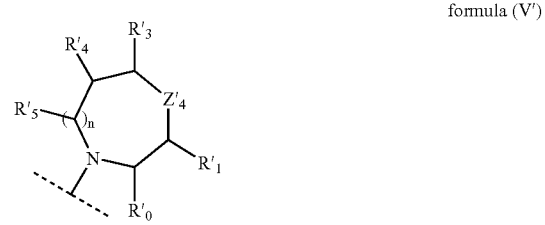

formula (V')

in which formulae $Z'_1$ represents an oxygen or sulphur atom or a radical $NR'_{12}$, $Z'_2$ represents a nitrogen atom or a radical $CR'_{11}$, $R'_{12}$ and $R'_{13}$ represent, independently of each other, a $C_1$–$C_8$ alkyl radical, optionally substituted with one or more radicals chosen from a hydroxyl, a $C_1$–$C_2$ alkoxy, a $C_2$–$C_4$ (poly)hydroxyalkoxy, an amino, a $C_1$–$C_2$ (di)alkylamino, a carboxyl or a sulphonic radical; an optionally substituted phenyl radical, $R'_{10}$ and $R'_{11}$ represent, independently of each other, a hydrogen atom; a $C_1$–$C_4$ alkyl radical, optionally substituted with one or more radicals chosen from a hydroxyl, a $C_1$–$C_2$ alkoxy, a $C_2$–$C_4$ (poly)hydroxyalkoxy, an amino, a $C_1$–$C_2$ (di)alkylamino, a carboxyl or a sulphonic radical; an optionally substituted phenyl radical; a carboxyl radical; a sulphonylamino radical;

$R'_6$, $R'_7$, $R'_8$ and $R'_9$ represent, independently of each other, a hydrogen atom; a chlorine atom; a bromine atom; a linear or branched $C_1$–$C_6$ hydrocarbon-based chain, which can form one or more 3- to 6-membered carbon-based rings, and which may be saturated or unsaturated, one or more carbon atoms of the carbon-based chain of which may be replaced with an oxygen, nitrogen or sulphur atom or with an $SO_2$ group, and the carbon atoms of which may, independently of each other, be substituted with one or more halogen atoms; $R'_6$, $R'_7$, $R'_8$ and $R'_9$ not comprising a peroxide bond or diazo or nitroso radicals, n is an integer equal to 1 or 2, $Z'_4$ represents an oxygen or sulphur atom, a radical $NR'_2$ or a radical $CR'_2R''_2$, $R'_0$, $R'_1$, $R'_2$, $R''_2$, $R'_3$, $R'_4$ and $R'_5$ represent, independently of each other, a hydrogen atom; an alkyl radical; an alkoxy radical; a hydroxyl radical; amino; acetoxy; a group —$NR_{14}R_{15}$, $R_{14}$ and $R_{15}$ representing, independently of each other, a hydrogen atom, a $C_1$–$C_4$ alkyl radical substituted with one or more radicals chosen from a halogen atom, a hydroxyl, $C_1$–$C_2$ alkoxy, amino or $C_1$–$C_2$ amino(di)alkyl radical; a sulphonylamino radical; a carboxyl radical; a carboxamido radical; an amido radical; a mono- or dialkylamido radical; a halogen; a $C_1$–$C_6$ alkyl radical substituted with one or more radicals chosen from a hydroxyl, $C_1$–$C_2$ alkoxy, $C_2$–$C_4$ (poly)hydroxyalkoxy, amino, or $C_1$–$C_2$ (di)alkylamino radical, X' is an organic or mineral anion.

(C) the monocationic monoazo dyes described in application WO 02-078657, the passage of this application devoted to monocationic monoazo dyes and to their synthesis is incorporated by reference in the present application.

These dyes correspond to the compounds of general formula (Vj):

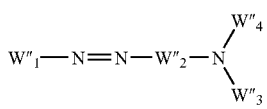

in which $W''_1$ represents a 5-membered cationic aromatic heterocycle of formula (II″) below:

formula (II″)

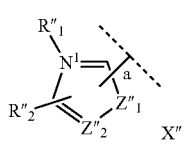

$W''_2$ represents a divalent carbon-based aromatic or pyridine group of formula (III″) or (IV″) below formula (III″)

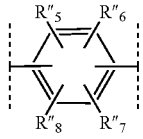

formula (IV″)

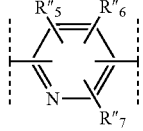

in which formulae $Z''_1$ represents an oxygen or sulphur atom or a radical $NR''_4$, $Z''_2$ represents a nitrogen atom or a radical $CR''_3$, $R''_1$ and $R''_4$ represent, independently of each other, a $C_1$–$C_8$ alkyl radical, optionally substituted with one or more radicals chosen from a hydroxyl, a $C_1$–$C_2$ alkoxy, a $C_2$–$C_4$ (poly)hydroxyalkoxy, an amino, a $C_1$–$C_2$ (di)alkylamino, a carboxyl or a sulphonic radical; an optionally substituted phenyl radical, $R''_2$ and $R''_3$ represent, independently of each other, a hydrogen atom; a $C_1$–$C_4$ alkyl radical, optionally substituted with one or more radicals chosen from a hydroxyl, a $C_1$–$C_2$ alkoxy, a $C_2$–$C_4$ (poly)hydroxyalkoxy, an amino, a $C_1$–$C_2$ (di)alkylamino, a carboxyl or a sulphonic radical; an optionally substituted phenyl radical; a carboxyl radical; a sulphonylamino radical;

$R''_5$, $R''_6$, $R''_7$, $R''_8$ and $W''_4$ represent, independently of each other, a hydrogen atom; a chlorine atom; a bromine atom; a linear or branched $C_1$–$C_6$ hydrocarbon-based chain, which can form one or more 3- to 6-membered carbon-based rings, and which may be saturated or unsaturated, one or more carbon atoms of the hydrocarbon-based chain of which may be replaced with an oxygen, nitrogen or sulphur atom or with an $SO_2$ group, and the carbon atoms of which may, independently of each other, be substituted with one or more halogen atoms; $R''_5$, $R''_6$, $R''_7$, $R''_8$ and $W''_4$ not comprising a peroxide bond or diazo or nitroso radicals, and $W''_4$ being a non-aromatic substituent, $W''_3$ represents a thienyl, pyrazolyl, pyrrolyl, imidazolyl, furyl, triazolyl, thiadiazolyl, isoxazolyl, isothiazolyl, thiazolyl, oxazolyl, pyridyl, pyrimidinyl, triazinyl, pyridazinyl or pyrazinyl radical, each of these heteroaromatic rings possibly being substituted with at least one $C_1$–$C_6$ alkyl radical, optionally substituted with one or more hydroxyl, $C_1$–$C_4$ alkoxy, (poly)hydroxyalkoxy, amino, $C_1$–$C_4$ (di)alkylamino, $C_2$–$C_4$ (poly)hydroxyalkylamino, carboxyl, sulphonyl, alkoxycarbonyl or $C_1$–$C_4$ thioether radicals; a phenyl radical optionally substituted with one or more radicals chosen from $C_1$–$C_2$ alkoxy, amino, $C_1$–$C_2$ (di)alkylamino, carboxyl, sulphonyl, $C_1$–$C_4$ alkyl, halogen or $C_1$–$C_2$ thioether radicals, a halogen such as a chlorine, fluorine or bromine atom; an amino radical; a $C_1$–$C_4$ alkylamino radical, a $C_2$–$C_4$ (poly)hydroxyalkylamino radical, a $C_1$–$C_4$ (di)alkylamino radical; a $C_1$–$C_2$ alkoxy radical; a carboxyl radical; a sulphonylamino radical, X″ is an organic or mineral anion.

(D) the monoazo dyes of formula (Vk):

$$W^o_1-W^o_2-N=N-W^o_3$$

in which $W^o_1$, represents a 5-, 6-, 7- or 8-membered heterocycle of formula (II$^o$) below formula (II$^o$)

[Chemical structure showing a ring with substituents $R^o_3$, $R^o_4$, $()_n$, $Z^o_1$, N, $R^o_1$, $R^o_0$]

$W^o_2$ represents a divalent carbon-based aromatic, pyridine or pyridazine group of formula (III$^o$) below formula (III$^o$)

[Chemical structure showing a ring with substituents $R^o_5$, $R^o_6$, $X^o_1$, $X^o_2$]

$W^o_3$ represents a cationic heteroaromatic radical represented by formula (IV$^o$) below:

(IV$^o$)

[Chemical structure showing a ring with substituents $R^o_9$, $R^o_{10}$, $R^o_{11}$, $R^o_{12}$, $R^o_{13}$, $+N$, $X^o$, $Z^o_2$, a]

in which formulae (II$^o$), (III$^o$) and (IV$^o$):

n=0, 1, 2 or 3, it being understood that when n is greater than or equal to 2, then the radicals $R^o_4$ may be identical or different, $X^o_1$ represents a nitrogen atom or a radical $CR^o_7$, $X^o_2$ represents a nitrogen atom or a radical $CR^o_8$, $Z^o_1$ represents a radical $CHR^o_2$, an oxygen or sulphur atom or a radical $NR^o_{14}$, $Z^o_2$ represents an oxygen or sulphur atom or a radical $NR^o_{15}$ $R^o_0$, $R^o_1$, $R^o_2$, $R^o_3$, $R^o_4$, $R^o_5$, $R^o_6$, $R^o_7$, $R^o_8$, $R^o_9$, $R^o_{10}$, $R^o_{11}$ and $R^o_{12}$, which may be identical or different, represent a hydrogen atom, a linear or branched $C_1-C_{10}$ hydrocarbon-based chain, which can form one or more 3- to 6-membered carbon-based rings, and which may be saturated or unsaturated, one or more carbon atoms of the carbon-based chain of which may be replaced with an oxygen, nitrogen or sulphur atom or with an $SO_2$ group, and the carbon atoms of which may be, independently of each other, substituted with one or more halogen atoms; $R^o_0$, $R^o_1$, $R^o_2$, $R^o_3$, $R^o_4$, $R^o_5$, $R^o_6$, $R^o_7$, $R^o_8$, $R^o_9$, $R^o_{11}$ and $R^o_{12}$ not comprising a peroxide bond or diazo or nitroso radicals, $R^o_{14}$ represents a hydrogen atom, a linear or branched $C_1-C_{10}$ hydrocarbon-based chain, which can form one or more 3- to 6-membered carbon-based rings, and which may be saturated or unsaturated, one or more carbon atoms of the carbon-based chain of which may be replaced with an oxygen, nitrogen or sulphur atom or with an $SO_2$ group, and the carbon atoms of which may be, independently of each other, substituted with one or more halogen atoms, $R^o_{14}$ not comprising a peroxide bond or diazo or nitroso radicals; it being understood that the said oxygen, nitrogen and sulphur atoms are not directly linked to the nitrogen atom bearing the radical $R^o_{14}$, $R^o_5$ with $R^o_6$ can form a carbon-based aromatic ring, such as a phenyl, $R^o_{13}$ and $R^o_{15}$, which may be identical or different, represent a $C_1-C_8$ alkyl radical, optionally substituted with one or more radicals chosen from the group consisting of a hydroxyl, a $C_1-C_2$ alkoxy, a $C_2-C_4$ (poly)hydroxyalkoxy, an amino, a $C_1-C_2$ (di)alkylamino, a carboxyl, a sulphonic or an optionally substituted phenyl radical;

the bond a of the cationic ring of formula (IV) is linked to the azo group of formula (I);

$X^o$ is an organic or mineral anion.

Among the monocationic monoazo dyes of formula (Vk), mention may especially be made, preferably, of:

1,3-dimethyl-2-[4-(pyrrolidin-1-yl)phenylazo]benzimidazol-1-ium, 1,3-dimethyl-2-[4-(3-hydroxypyrrolidin-1-yl)phenylazo]-benzimidazol-1-ium, 1,3-dimethyl-2-[4-(2-carboxypyrrolidin-1-yl)phenylazo]-benzimidazol-1-ium, 1,3-dimethyl-2-[4-(3-aminopyrrolidin-1-yl)phenylazo]-benzimidazol-1-ium, 1,3-dimethyl-2-[4-(2-carboxy-3-hydroxypyrrolidin-1-yl)-phenylazo]-benzimidazol-1-ium, 1,3-dimethyl-2-[4-(2-carboxamidopyrrolidin-1-yl)phenylazo]-benzimidazol-1-ium, 1,3-dimethyl-2-[4-(2-hydroxymethylpyrrolidin-1-yl)-phenylazo]benzimidazol-1-ium, 1,3-dimethyl-2-[4-(2-carboxy-4-hydroxypyrrolidin-1-yl)-phenylazo]benzimidazol-1-ium, 1,3-dimethyl-2-[4-(piperidin-1-yl)phenylazo]benzimidazol-1-ium, 1,3-dimethyl-2-[4-(3-hydroxypiperidin-1-yl)phenylazo]-benzimidazol-1-ium, 1,3-dimethyl-2-[4-(3-hydroxymethylpiperidin-1-yl)phenylazo]-benzimidazol-1-ium, 1,3-dimethyl-2-[4-(3-carboxypiperidin-1-yl)phenylazo]-benzimidazol-1-ium, 1,3-dimethyl-2-[4-(2-carboxypiperidin-1-yl)phenylazo]-benzimidazol-1-ium, 1,3-dimethyl-2-[4-(piperazin-1-yl)phenylazo]benzimidazol-1-ium, 1,3-dimethyl-2-[4-(homopiperazin-1-yl)phenylazo]-benzimidazol-1-ium, 5-amino-1,3-dimethyl-2-[4-(pyrrolidin-1-yl)phenylazo]-benzimidazol-1-ium, 5-amino-1,3-dimethyl-2-[4-(3-hydroxypyrrolidin-1-yl)phenylazo]benzimidazol-1-ium, 5-amino-1,3-dimethyl-2-[4-(2-carboxypyrrolidin-1-yl)-phenylazo]benzimidazol-1-ium, 5-amino-1,3-dimethyl-2-[4-(3-aminopyrrolidin-1-yl)-phenylazo]benzimidazol-1-ium, 5-amino-1,3-dimethyl-2-[4-(2-carboxy-3-hydroxypyrrolidin-1-yl)phenylazo]benzimidazol-1-ium, 5-amino-1,3-dimethyl-2-[4-(2-carboxamidopyrrolidin-1-yl)-phenylazo]benzimidazol-1-ium,
5-amino-1,3-dimethyl-2-[4-(2-hydroxymethylpyrrolidin-1-yl)-phenylazo]benzimidazol-1-ium,
5-amino-1,3-dimethyl-2-[4-(2-carboxy-4-hydroxypyrrolidin-1-yl)phenylazo]benzimidazol-1-ium,
5-amino-1,3-dimethyl-2-[4-(piperidin-1-yl)phenylazo]-benzimidazol-1-ium,
5-amino-1,3-dimethyl-2-[4-(3-hydroxypiperidin-1-yl)-phenylazo]benzimidazol-1-ium,
5-amino-1,3-dimethyl-2-[4-(3-hydroxymethylpiperidin-1-yl)-phenylazo]benzimidazol-1-ium,
5-amino-1,3-dimethyl-2-[4-(3-carboxypiperidin-1-yl)-phenylazo]benzimidazol-1-ium,
5-amino-1,3-dimethyl-2-[4-(2-carboxypiperidin-1-yl)-phenylazo]benzimidazol-1-ium,
5-amino-1,3-dimethyl-2-[4-(piperazin-1-yl)phenylazo]-benzimidazol-1-ium,
5-amino-1,3-dimethyl-2-[4-(homopiperazin-1-yl)phenylazo]-benzimidazol-1-ium,
5-dimethylamino-1,3-dimethyl-2-[4-(pyrrolidin-1-yl)-phenylazo]benzimidazol-1-ium,
5-dimethylamino-1,3-dimethyl-2-[4-(3-hydroxypyrrolidin-1-yl)phenylazo]benzimidazol-1-ium,
5-dimethylamino-1,3-dimethyl-2-[4-(2-carboxypyrrolidin-1-yl)-phenylazo]benzimidazol-1-ium,
5-dimethylamino-1,3-dimethyl-2-[4-(3-aminopyrrolidin-1-yl)-phenylazo]benzimidazol-1-ium,
5-dimethylamino-1,3-dimethyl-2-[4-(2-carboxy-3-hydroxypyrrolidin-1-yl)phenylazo]benzimidazol-1-ium,
5-dimethylamino-1,3-dimethyl-2-[4-(2-carboxamidopyrrolidin-1-yl)phenylazo]benzimidazol-1-ium,
5-dimethylamino-1,3-dimethyl-2-[4-(2-hydroxymethyl-pyrrolidin-1-yl)phenylazo]benzimidazol-1-ium,
5-dimethylamino-1,3-dimethyl-2-[4-(2-carboxy-4-hydroxypyrrolidin-1-yl)phenylazo]benzimidazol-1-ium,
5-dimethylamino-1,3-dimethyl-2-[4-(piperidin-1-yl)phenylazo]-benzimidazol-1-ium,
5-dimethylamino-1,3-dimethyl-2-[4-(3-hydroxypiperidin-1-yl)-phenylazo]benzimidazol-1-ium,
5-dimethylamino-1,3-dimethyl-2-[4-(3-hydroxymethyl-piperidin-1-yl)phenylazo]benzimidazol-1-ium,
5-dimethyl amino-1,3-dimethyl-2-[4-(3-carboxypiperidin-1-yl)-phenylazo]benzimidazol-1-ium,
5-dimethylamino-1,3-dimethyl-2-[4-(2-carboxypiperidin-1-yl)-phenylazo]benzimidazol-1-ium,
5-dimethylamino-1,3-dimethyl-2-[4-(piperazin-1-yl)-phenylazo]benzimidazol-1-ium,
5-dimethylamino-1,3-dimethyl-2-[4-(homopiperazin-1-yl)-phenylazo]benzimidazol-1-ium.

(E) the monocationic monoazo dyes are described in application EP 0953334, the passage of this application devoted to monocationic monoazo dyes and to their synthesis is incorporated by reference in the present application.

These dyes correspond to the compounds of general formulae (Vl), (Vm), (Vn) and (Vo) below:

a) the compounds of formula (Vl) below:

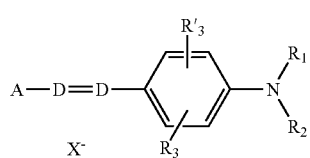

in which:

D represents a nitrogen atom or a —CH group, $R_1$ and $R_2$, which may be identical or different, represent a hydrogen atom; a $C_1$–$C_4$ alkyl radical which may be substituted with a —CN, —OH or —NH$_2$ radical or form, with a carbon atom of the benzene ring, a heterocycle optionally containing oxygen or nitrogen, which may be substituted with one or more $C_1$–$C_4$ alkyl radicals; a 4'-aminophenyl radical, $R_3$ and $R'_3$, which may be identical or different, represent a hydrogen atom, a halogen atom chosen from chlorine, bromine, iodine and fluorine, or a cyano, $C_1$–$C_4$ alkoxy or acetyloxy radical, $X^-$ represents an anion preferably chosen from chloride, methyl sulphate and acetate, A represents a group chosen from structures A1 to A19 below:

A$_1$

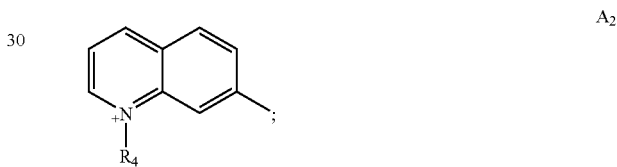

A$_2$

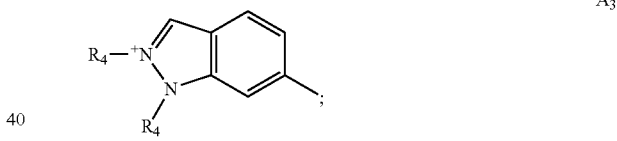

A$_3$

A$_4$

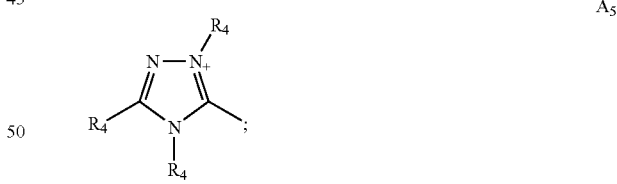

A$_5$

A$_6$

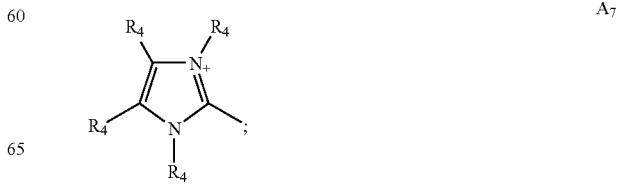

A$_7$

-continued

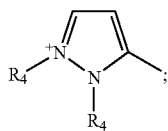
A8

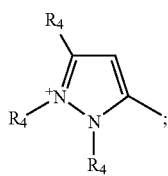
A9

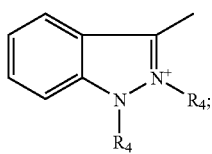
A10

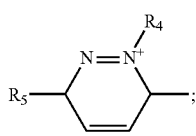
A11

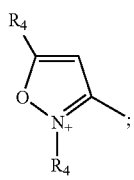
A12

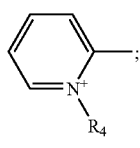
A13

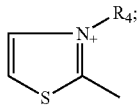
A14

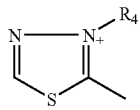
A15

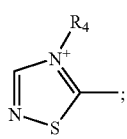
A16

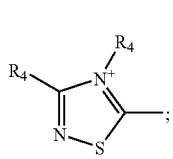
A17

-continued

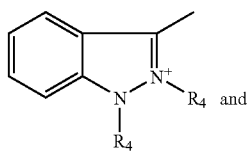
A18

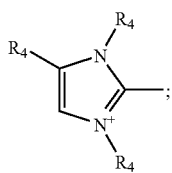
A19 in which $R_4$ represents a $C_1$–$C_4$ alkyl radical which may be substituted with a hydroxyl radical and $R_5$ represents a $C_1$–$C_4$ alkoxy radical, with the proviso that when D represents —CH, A represents $A_4$ or $A_{13}$ and $R_3$ is other than an alkoxy radical, then $R_1$ and $R_2$ do not simultaneously denote a hydrogen atom;

b) the compounds of formula (Vm) below:

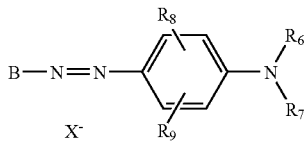

in which:

$R_6$ represents a hydrogen atom or a $C_1$–$C_4$ alkyl radical, $R_7$ represents a hydrogen atom, an alkyl radical which may be substituted with a —CN radical or with an amino group, a 4'-aminophenyl radical or forms with $R_6$ a heterocycle optionally containing oxygen and/or nitrogen, which may be substituted with a $C_1$–$C_4$ alkyl radical, $R_8$ and $R_9$, which may be identical or different, represent a hydrogen atom, a halogen atom such as bromine, chlorine, iodine or fluorine, a $C_1$–$C_4$ alkyl or $C_1$–$C_4$ alkoxy radical or a —CN radical, $X^-$ represents an anion preferably chosen from chloride, methyl sulphate and acetate, B represents a group chosen from structures B1 to B6 below:

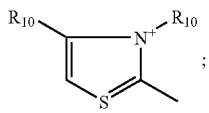
B1

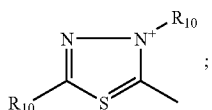
B2

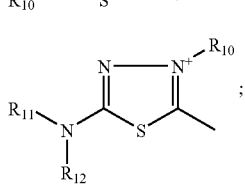
B3

-continued

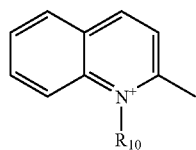
B4

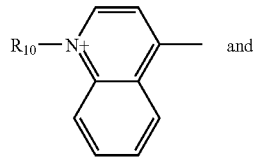
B5

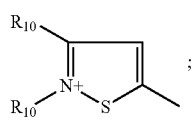
B6 in which $R_{10}$ represents a $C_1$–$C_4$ alkyl radical, $R_{11}$ and $R_{12}$, which may be identical or different, represent a hydrogen atom or a $C_1$–$C_4$ alkyl radical;

c) the compounds of formulae (Vn) and (Vo) below:

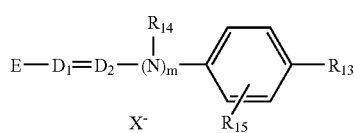
(Vn)

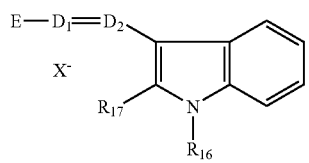
(Vo)

in which:

$R_{13}$ represents a hydrogen atom, a $C_1$–$C_4$ alkoxy radical, a halogen atom such as bromine, chlorine, iodine or fluorine, or an amino radical, $R_{14}$ represents a hydrogen atom, a $C_1$–$C_4$ alkyl radical or forms with a carbon atom of the benzene ring a heterocycle optionally containing oxygen and/or substituted with one or more $C_1$–$C_4$ alkyl groups, $R_{15}$ represents a hydrogen atom or a halogen atom such as bromine, chlorine, iodine or fluorine, $R_{16}$ and $R_{17}$, which may be identical or different, represent a hydrogen atom or a $C_1$–$C_4$ alkyl radical, $D_1$ and $D_2$, which may be identical or different, represent a nitrogen atom or a —CH group, m=0 or 1, it being understood that when $R_{13}$ represents an unsubstituted amino group, then $D_1$ and $D_2$ simultaneously represent a —CH group and m=0, $X^-$ represents an anion preferably chosen from chloride, methyl sulphate and acetate, E represents a group chosen from structures E1 to E8 below:

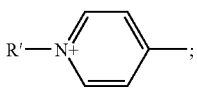
E1

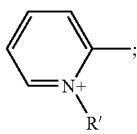
E2

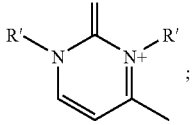
E3

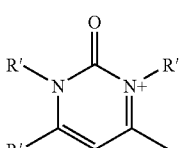
E4

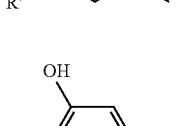
E5

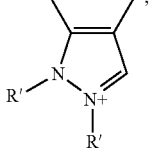
E6

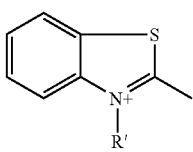
E7 and

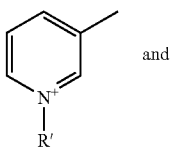
E8 in which R' represents a $C_1$–$C_4$ alkyl radical;

when m=0 and when $D_1$ represents a nitrogen atom, then E may also denote a group of structure E9 below:

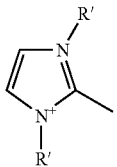

E9 in which R' represents a $C_1$–$C_4$ alkyl radical.

(F) the monocationic monoazo dyes described in application EP 0960617, the passage of this application devoted to monocationic monoazo dyes and to their synthesis is incorporated by reference in the present application.

These dyes correspond to the compounds of general formula (Vp):

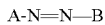

in which:

the symbol A represents a group chosen from structures A1 to A3 below:

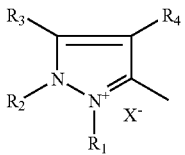 A1

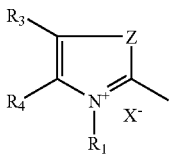 A2

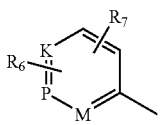 A3 in which structures A1 to A3, $R_1$ denotes a $C_1$–$C_4$ alkyl radical, a phenyl radical which may be substituted with a $C_1$–$C_4$ alkyl radical or a halogen atom chosen from chlorine, bromine, iodine and fluorine;

$R_2$ denotes a $C_1$–$C_4$ alkyl radical or a phenyl radical;

$R_3$ and $R_4$, which may be identical or different, represent a $C_1$–$C_4$ alkyl radical, a phenyl radical or, in the case of structure A1, may together form a substituted benzene ring, and in the case of structure A2, may together form a benzene ring optionally substituted with one or more $C_1$–$C_4$ alkyl, $C_1$–$C_4$ alkoxy or $NO_2$ radicals;

$R_3$ may also denote a hydrogen atom;

Z denotes an oxygen or sulphur atom or a group —$NR_2$;

M represents a group —CH, —CR (R denoting $C_1$–$C_4$ alkyl), or —$NR_5(X^-)_r$;

K represents a group —CH, —CR (R denoting $C_1$–$C_4$ alkyl), or —$NR_5(X^-)_r$;

P represents a group —CH, —CR (R denoting $C_1$–$C_4$ alkyl), or —$NR_5(X^-)_r$; r denotes zero or 1;

$R_5$ represents an atom $O^-$, a $C_1$–$C_4$ alkoxy radical or a $C_1$–$C_4$ alkyl radical;

$R_6$ and $R_7$, which may be identical or different, represent a hydrogen atom or a halogen atom chosen from chlorine, bromine, iodine and fluorine, a $C_1$–$C_4$ alkyl radical, a $C_1$–$C_4$ alkoxy radical or an —$NO_2$ radical;

$X^-$ represents an anion preferably chosen from chloride, iodide, methyl sulphate, ethyl sulphate, acetate and perchlorate;

with the proviso that, if $R_4$ denotes a $C_1$–$C_4$ alkyl radical and Z denotes a sulphur atom, then $R_3$ does not denote a hydrogen atom;

if $R_5$ denotes $O^-$, then r denotes zero;

if K or P or M denote —N—($C_1$–$C_4$)alkyl $X^-$, then $R_6$ or $R_7$ is other than a hydrogen atom;

if K denotes —$NR_5(X^-)_r$, then M=P=—CH; —CR;

if M denotes —$NR_5(X^-)_r$, then K=P=—CH; —CR;

if P denotes —$NR_5(X^-)_r$, then K=M and denote —CH or —CR;

if Z denotes —$NR_2$ and $R_2$ denotes a $C_1$–$C_4$ alkyl radical, then at least one of the radicals $R_1$, $R_3$ or $R_4$ of $A_2$ is other than a $C_1$–$C_4$ alkyl radical;

the symbol B represents:

(a) a group of structure $B_1$ below:

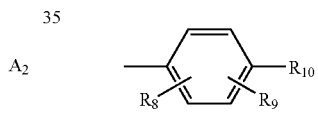 $B_1$ in which structure $B_1$, $R_8$ represents a hydrogen atom, a halogen atom chosen from chlorine, bromine, iodine and fluorine, a $C_1$–$C_4$ alkyl or $C_1$–$C_4$ alkoxy radical, a radical —OH, —$NO_2$, —$NHR_{11}$, —$NR_{12}R_{13}$ or —NHCO—($C_1$–$C_4$)alkyl, or forms with $R_9$ a 5- or 6-membered ring optionally containing one or more heteroatoms chosen from nitrogen, oxygen or sulphur;

$R_9$ represents a hydrogen atom, a halogen atom chosen from chlorine, bromine, iodine and fluorine, or a $C_1$–$C_4$ alkyl or $C_1$–$C_4$ alkoxy radical, or forms with $R_{10}$ or $R_{11}$ a 5- or 6-membered ring optionally containing one or more heteroatoms chosen from nitrogen, oxygen or sulphur;

$R_{10}$ represents a hydrogen atom, an —OH radical, a radical —$NHR_{11}$ or a radical —$NR_{12}R_{13}$;

$R_{11}$ represents a hydrogen atom, a $C_1$–$C_4$ alkyl radical, a $C_1$–$C_4$ monohydroxyalkyl radical, a $C_2$–$C_4$ polyhydroxyalkyl radical or a phenyl radical;

$R_{12}$ and $R_{13}$, which may be identical or different, represent a $C_1$–$C_4$ alkyl radical, a $C_1$–$C_4$ monohydroxyalkyl radical or a $C_2$–$C_4$ polyhydroxyalkyl radical;

(b) a 5- or 6-membered nitrogenous heterocyclic group which may contain other heteroatoms and/or carbonyl groups and which may be substituted with one or more $C_1$–$C_4$ alkyl, amino or phenyl radicals, and especially a group of structure B2 below:

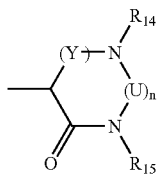

in which structure $B_2$, $R_{14}$ and $R_{15}$, which may be identical or different, represent a hydrogen atom, a $C_1$–$C_4$ alkyl radical or a phenyl radical;

Y denotes the —CO— radical or the radical

n=0 or 1 with, when n denotes 1, U denotes the CO radical.

In the structures defined above, the $C_1$–$C_4$ alkyl or alkoxy group preferably denotes methyl, ethyl, butyl, methoxy or ethoxy.

Most particularly, the monocationic monoazo direct dyes which will be used are those containing as heterocycle an imidazolium or pyridinium ring substituted with one or more (2, 3 or 4) alkyl groups, which are preferably $C_1$–$C_6$.

By way of example of the latter compounds, mention may be made of Basic Red 22, Basic Red 51 (compound of structure (VI), Basic Orange 31 (compound of structure VI) and Basic Yellow 87 (compound of structure $V_n$).

The cationic direct dye(s) of the invention represent(s) from 0.005% to 20%, preferably 0.01% to 10% and even more preferably from 0.05% to 5% by weight relative to the total weight of the compositions.

According to a first preferred embodiment, the composition according to the present invention additionally contains at least one cationic polymer.

For the purposes of the present invention, the expression "cationic polymer" denotes any polymer containing cationic groups and/or groups which are ionizable to cationic groups.

The cationic polymers which can be used in accordance with the present invention may be chosen from all those already known per se as improving the cosmetic properties of hair, namely in particular those described in patent application EP-A-337 354 and in French patents FR-2 270 846, 2 383 660, 2 598 611, 2 470 596 and 2 519 863.

The preferred cationic polymers are chosen from those which contain units comprising primary, secondary, tertiary and/or quaternary amine groups which may either be part of the main polymer chain, or which may be carried by a side substituent directly linked to the latter.

The cationic polymers used generally have a number-average molecular mass between 500 and $5.10^6$ approximately, and preferably between $10^3$ and $3.10^6$ approximately.

Among the cationic polymers, there may be mentioned more particularly polymers of the polyamine, polyamino amide and poly(quaternaryammonium) type.

They are known products. They are described in particular in French patents No. 2 505 348 or 2 542 997. Among the said polymers, there may be mentioned:

(1) the homopolymers or copolymers derived from acrylic or methacrylic esters or amides and comprising at least one of the units of the following formulae (VI), (VII), (VIII) or (IX):

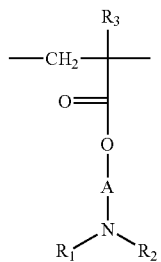

(VI)

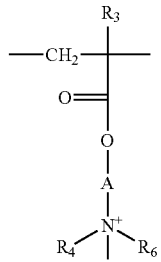

(VII)

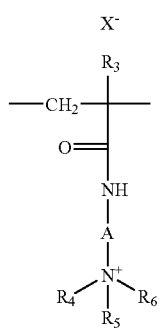

(VIII)

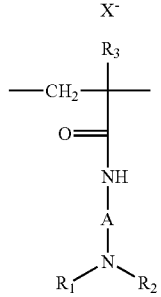

(IX)

in which:

$R_3$ denotes a hydrogen atom or a $CH_3$ radical;

A represents a linear or branched alkyl group of 1 to 6 carbon atoms, preferably 2 or 3 carbon atoms or a hydroxyalkyl group of 1 to 4 carbon atoms;

$R_4$, $R_5$, $R_6$, which are identical or different, represent an alkyl group having from 1 to 6 carbon atoms or a benzyl radical;

$R_1$ and $R_2$, which are identical or different, represent hydrogen or an alkyl group having from 1 to 6 carbon atoms and preferably methyl or ethyl;

$X^-$ denotes an anion derived from an inorganic or organic acid such as a methosulphate anion or a halide such as chloride or bromide.

The polymers of the family (1) may contain, in addition, one or more units derived from comonomers which may be chosen from the family of acrylamides, methacrylamides, diacetone acrylamides, acrylamides and methacrylamides substituted on the nitrogen with lower ($C_1$–$C_4$)alkyls, acrylic or methacrylic acids or esters thereof, vinyllactams such as vinylpyrrolidone or vinylcaprolactam, vinyl esters.

Thus, among these polymers of the family (1), there may be mentioned:

the copolymers of acrylamide and dimethylaminoethyl methacrylate quaternized with dimethyl sulphate or with a dimethyl halide such as that sold under the name HERCOFLOC by the company HERCULES, the copolymers of acrylamide and methacryloyloxy-ethyltrimethylammonium chloride described, for example, in Patent Application EP-A-080976 and sold under the name BINA QUAT P 100 by the company CIBA GEIGY, the copolymer of acrylamide and methacryloyloxy-ethyltrimethylammonium methosulphate sold under the name RETEN by the company HERCULES, the vinylpyrrolidone/dialkylaminoalkyl acrylate or methacrylate copolymers, quaternized or otherwise, such as the products sold under the name "GAFQUAT" by the company ISP such as for example "GAFQUAT 734" or "GAFQUAT 755" or alternatively the products called "COPOLYMER 845, 958 and 937". These polymers are described in detail in French Patents 2 077 143 and 2 393 573, the dimethylaminoethyl methacrylate/vinylcaprolactam/vinylpyrrolidone terpolymers such as the product sold under the name GAFFIX VC 713 by the company ISP, the vinylpyrrolidone/methacrylamidopropyldimethylamine copolymers marketed in particular under the name STYLEZE CC 10 by ISP, and the quaternized vinylpyrrolidone/dimethyl aminopropyl methacrylamide copolymers such as the product sold under the name "GAFQUAT HS 100" by the company ISP.

(2) The cellulose ether derivatives comprising quaternary ammonium groups, described in French Patent 1 492 597, and in particular the polymers marketed under the names "JR" (JR 400, JR 125, JR 30M) or "LR" (LR 400, LR 30M) by the company Union Carbide Corporation. These polymers are also defined in the CTFA dictionary as hydroxyethyl cellulose quaternary ammoniums which have reacted with an epoxide substituted by a trimethylammonium group.

(3) Cationic cellulose derivatives such as cellulose copolymers or cellulose derivatives grafted with a quaternary ammonium water-soluble monomer, and described especially in U.S. Pat. No. 4,131,576, such as hydroxyalkyl celluloses like hydroxymethyl, hydroxyethyl or hydroxypropyl celluloses grafted especially with a methacryloylethyltrimethylammonium, methacrylamidopropyl-trimethylammonium or dimethyldiallylammonium salt.

The commercialized products corresponding to this definition are more particularly the products sold under the name "Celquat L 200" and "Celquat H 100" by the company National Starch.

(4) The cationic polysaccharides described more particularly in U.S. Pat. Nos. 3,589,578 and 4,031,307 such as guar gums containing cationic trialkylammonium groups. Guar gums modified with a 2,3-epoxypropyltri methylammonium salt (e.g. chloride) are for example used.

Such products are marketed in particular under the trade names JAGUAR C13 S, JAGUAR C 15, JAGUAR C 17 or JAGUAR C162 by the company MEYHALL.

(5) Polymers consisting of piperazinyl units and of alkylene or hydroxyalkylene divalent radicals with straight or branched chains, optionally interrupted by oxygen, sulphur or nitrogen atoms or by aromatic or heterocyclic rings, as well as the oxidation and/or quaternization products of these polymers. Such polymers are described especially in French patents 2 162 025 and 2 280 361;

(6) Water-soluble polyaminoamides prepared in particular by polycondensation of an acid compound with a polyamine; these polyaminoamides may be crosslinked with an epihalohydrin, a diepoxide, a dianhydride, an unsaturated dianhydride, a diunsaturated derivative, a bishalohydrin, a bisazetidinium, a bishaloacyldiamine, an alkylbishalide or else with an oligomer resulting from the reaction of a difunctional compound which is reactive towards a bishalohydrin, a bisazetidinium, a bishaloacyldiamine, an alkylbishalide, an epihalohydrin, a diepoxide or a diunsaturated derivative; the crosslinking agent being employed in proportions ranging from 0.025 to 0.35 mol per amine group of the polyaminoamide; these polyaminoamides may be alkylated or, if they include one or more tertiary amine functional groups, quaternized. Such polymers are described especially in French Patents 2 252 840 and 2 368 508.

(7) Polyaminoamide derivatives resulting from the condensation of polyalkylenepolyamines with polycarboxylic acids, followed by an alkylation with difunctional agents. There may be mentioned, for example, the adipic acid/dialkylaminohydroxy-alkyldialkylenetriamine polymers in which the alkyl radical contains from 1 to 4 carbon atoms and preferably denotes methyl, ethyl or propyl. Such polymers are described especially in French Patent 1 583 363.

Among these derivatives there may be mentioned more particularly the adipic acid/dimethyl aminohydroxy-propyl/diethylenetriamine polymers sold under the name "Cartaretine F, F4 or F8" by the company Sandoz.

(8) Polymers obtained by reaction of a polyalkylenepolyamine containing two primary amine groups and at least one secondary amine group with a dicarboxylic acid chosen from diglycolic acid and saturated aliphatic dicarboxylic acids containing from 3 to 8 carbon atoms. The molar ratio of the polyalkylenepolyamine to the dicarboxylic acid being between 0.8:1 and 1.4:1; the polyaminoamide resulting therefrom being made to react with epichlorohydrin in a molar ratio of epichlorohydrin relative to the secondary amine group of the polyaminoamide of between 0.5:1 and 1.8:1. Such polymers are described especially in American Pat. Nos. 3,227,615 and 2,961,347.

Polymers of this type are marketed in particular under the name "Hercosett 57" by the company Hercules Inc. or else under the name of "PD 170" or "Delsette 101" by the company Hercules in the case of the copolymer of adipic acid/epoxypropyl/diethylene triamine.

(9) Cyclopolymers of alkyldiallylamine or of dialkyldiallylammonium, such as the homopolymers or copolymers comprising, as main constituent of the chain, units corresponding to the formulae (X) or (XI):

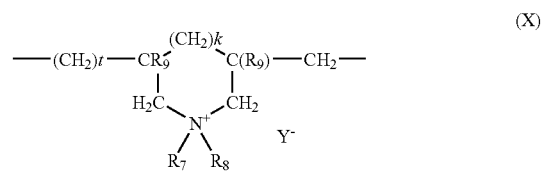

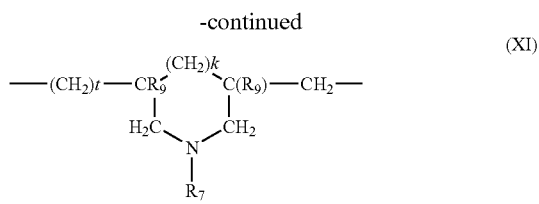

(XI)

in which formulae k and t are equal to 0 or 1, the sum k+t being equal to 1; $R_9$ denotes a hydrogen atom or a methyl radical; $R_7$ and $R_8$, independently of each other, denote an alkyl group containing from 1 to 6 carbon atoms, a hydroxyalkyl group in which the alkyl group preferably has 1 to 5 carbon atoms, or a lower ($C_1$–$C_4$)amidoalkyl group or $R_7$ and $R_8$ may denote, jointly with the nitrogen atom to which they are attached, heterocyclic groups such as piperidinyl or morpholinyl; $R_7$ and $R_8$, independently of each other, preferably denote an alkyl group having 1 to 4 carbon atoms; Y— is an anion such as bromide, chloride, acetate, borate, citrate, tartrate, bisulphate, bisulphite, sulphate or phosphate. These polymers are described especially in French Patent 2 080 759 and in its certificate of addition 2 190 406.

Among the polymers defined above there may be mentioned more particularly the dimethyldiallylammonium chloride homopolymer sold under the name "Merquat 100" by the company Calgon (and its homologues of low weight-average molecular masses) and the copolymers of diallyl dimethylammonium chloride and acrylamide marketed under the name "MERQUAT 550".

(10) The quaternary diammonium polymer containing repeat units corresponding to the formula:

(XII)

formula (XII) in which:

$R_{10}$, $R_{11}$, $R_{12}$ and $R_{13}$, which are identical or different, represent aliphatic, alicyclic or arylaliphatic radicals containing from 1 to 6 carbon atoms or lower hydroxyalkyl aliphatic radicals, or else $R_{10}$, $R_{11}$, $R_{12}$ and $R_{13}$, together or separately, form, with the nitrogen atoms to which they are attached, heterocyclic rings optionally containing a second heteroatom other than nitrogen, or else $R_{10}$, $R_{11}$, $R_{12}$ and $R_{13}$ denote a linear or branched $C_1$–$C_6$ alkyl radical substituted by a nitrile, ester, acyl, amide or —CO—O—$R_{14}$-D or —CO—NH—$R_{14}$-D group where $R_{14}$ is an alkylene and D a quaternary ammonium group;

$A_1$ and $B_1$ represent polymethylene groups containing from 2 to 20 carbon atoms which may be linear or branched, saturated or unsaturated and which may contain, bonded to or inserted into the main chain, one or more aromatic rings, or one or more oxygen or sulphur atoms or sulphoxide, sulphone, disulphide, amino, alkylamino, hydroxyl, quaternary ammonium, ureido, amide or ester groups, and X— denotes an anion derived from an inorganic or organic acid;

A1, $R_{10}$ and $R_{12}$, with the two nitrogen atoms to which they are attached, may form a piperazine ring; in addition if $A_1$ denotes a saturated or unsaturated, linear or branched alkylene or hydroxyalkylene radical, $B_1$ may also denote a group —$(CH_2)_n$—CO-D-OC—$(CH_2)_n$— in which D denotes:

a) a glycol residue of formula: —O-Z-O—, where Z denotes a linear or branched hydrocarbon radical or a group corresponding to one of the following formulae:

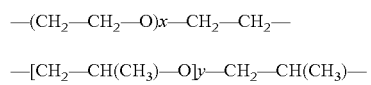

where x and y denote an integer from 1 to 4, representing a defined and unique degree of polymerization or any number from 1 to 4 representing a mean degree of polymerization;

b) a disecondary diamine residue such as a piperazine derivative;

c) a diprimary diamine residue of formula: —NH—Y—NH—, where Y denotes a linear or branched hydrocarbon radical or else the divalent radical

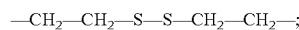

d) a ureylene group of formula: —NH—CO—NH—;

X— is preferably an anion such as chloride or bromide.

These polymers have a number-average molecular mass which is generally between 1 000 and 100 000.

Polymers of this type are described especially in French Patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is possible to use more particularly the polymers which consist of repeat units corresponding to the following formula (XIII):

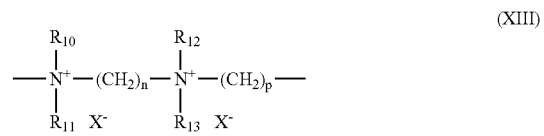

(XIII)

in which $R_{10}$, $R_{11}$, $R_{12}$ and $R_{13}$, which are identical or different, denote an alkyl or hydroxyalkyl radical having from 1 to 4 carbon atoms approximately, n and p are integers varying from 2 to 20 approximately and X— is an anion derived from an inorganic or organic acid.

(11) The quaternary polyammonium polymers consisting of repeat units of formula XIV):

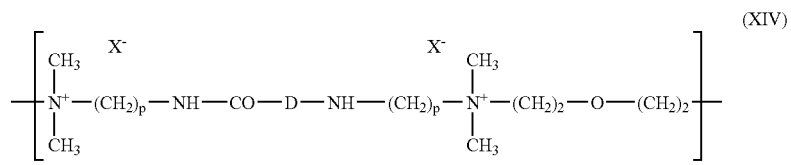

(XIV)

in which p denotes an integer varying from 1 to 6 approximately, D may be zero or may represent a group —(CH$_2$)$_r$—CO— in which r denotes a number equal to 4 or to 7, X— is an anion.

Such polymers may be prepared according to the methods described in U.S. Pat. No. 4,157,388, 4 702 906, 4 719 282. They are in particular described in patent application EP-A-122 324.

Among these, there may be mentioned for example the products "Mirapol A 15", "Mirapol AD1", "Mirapol AZ1" and "Mirapol 175" sold by the company Miranol.

(12) Quaternary vinylpyrrolidone and vinylimidazole polymers such as, for example, the products marketed under the names Luviquat FC 905, FC 550 and FC 370 by the company B.A.S.F.

(13) Polyamines like the Polyquart H sold by HENKEL, referenced under the name of "Polyethylene glycol (15) Tallow Polyamine" in the CTFA dictionary.

(14) The crosslinked polymers of methacryloyloxy(C$_1$–C$_4$ alkyl)tri(C$_1$–C$_4$ alkyl)ammonium salts such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. More particularly, it is possible to employ a crosslinked acrylamide/methacryloyloxyethyltrimethylammonium chloride copolymer (20/80 by weight) in the form of a dispersion containing 50% by weight of the said copolymer in mineral oil. This dispersion is marketed under the name of "SALCARE® SC 92" by the company ALLIED COLLOIDS. It is also possible to employ a crosslinked methacryloyloxyethyltrimethylammonium chloride homopolymer containing approximately 50% by weight of the homopolymer in mineral oil or in a liquid ester. These dispersions are marketed under the names of "SALCARE® SC 95" and "SALCARE® SC 96" by the company ALLIED COLLOIDS.

Other cationic polymers that may be employed within the scope of the invention are polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers which may be used in the context of the present invention, it is preferable to use the polymers of the families (1), (9), (10), (11) and (14) and more preferably still the polymers with the repeat units of the following formulae (W) and (U):

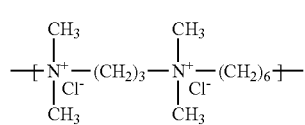

and in particular those whose molecular weight, determined by gel permeation chromatography, is between 9 500 and 9 900;

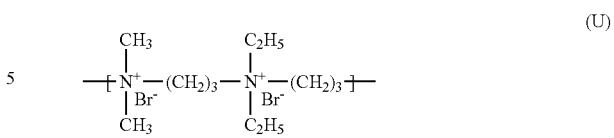

and in particular those whose molecular weight, determined by gel permeation chromatography, is about 1 200.

The cationic polymer concentration in the composition according to the present invention may vary from 0.01 to 10% by weight relative to the total weight of the composition, preferably from 0.05 to 5% and more preferably still from 0.1 to 3%.

According to a second preferred embodiment, the composition according to the present invention additionally contains at least one thickening polymer also called "rheology-adjusting agents".

The rheology-adjusting agents may be chosen from fatty acid amides (diethanol- or monoethanolamide of copra, monoethanolamide of oxyethylenated alkyl ether carboxylic acid), cellulosic thickeners (hydroxyethycellulose, hydroxypropylcellulose, carboxymethylcellulose), guar gum and its derivatives (hydroxypropylguar), gums of microbial origin (xanthan gum, scleroglucan gum), crosslinked homopolymers of acrylic acid or of acrylamidopropanesulphonic acid and the associative polymers as described below.

The associative polymers which can be used according to the invention are water-soluble polymers which are capable, in an aqueous medium, of reversibly combining with each other or with other molecules.

Their chemical structure comprises hydrophilic regions, and hydrophobic regions which are characterized by at least one fatty chain.

The associative polymers which can be used according to the invention may be of the anionic, cationic, amphoteric and preferably nonionic type.

Their concentration by weight in the dyeing composition may vary from about 0.01 to 10% of the total weight of the composition and in the ready-to-use composition (comprising the oxidizing agent) from about 0.0025 to 10% of the total weight of the composition. More preferably, this quantity varies from about 0.1 to 5% by weight in the dyeing composition and from about 0.025 to 10% in the ready-to-use composition.

Among the associative polymers of the anionic type, there may be mentioned:

(I) those comprising at least one hydrophilic unit and at least one allyl ether unit containing a fatty chain, more particularly those in which the hydrophilic unit consists of an ethylenic unsaturated anionic monomer, more particularly still of a vinylcarboxylic acid and most particularly of an acrylic acid, a methacrylic acid or mixtures thereof, and in which the allyl ether unit containing a fatty chain corresponds to the monomer having the following formula (XV):

$$CH_2=C\ R'CH_2O\ B_nR \qquad (XV)$$

in which R' denotes H or CH$_3$, B denotes the ethyleneoxy radical, n is zero or denotes an integer ranging from 1 to 100, R denotes a hydrocarbon radical chosen from the alkyl, arylalkyl, aryl, alkylaryl or cycloalkyl radicals, comprising from 8 to 30 carbon atoms, preferably 10 to 24, and more particularly still from 12 to 18 carbon atoms. A more particularly preferred unit of formula (XV) is a unit in which R' denotes H, n is equal to 10, and R denotes a stearyl ($C_{18}$) radical.

Anionic associative polymers of this type are described and prepared, according to a method of polymerization in emulsion, in patent EP-0 216 479.

Among these anionic associative polymers, the polymers formed from 20 to 60% by weight of acrylic acid and/or of methacrylic acid, from 5 to 60% by weight of lower alkyl (meth)acrylates, from 2 to 50% by weight of allyl ether containing a fatty chain of formula (XV), and from 0 to 1% by weight of a crosslinking agent which is a well-known copolymerizable polyethylenic unsaturated monomer such as diallyl phthalate, allyl (meth)acrylate, divinylbenzene, (poly)ethylene glycol dimethacrylate and methylenebisacrylamide, are particularly preferred according to the invention.

Among the latter, the crosslinked terpolymers of methacrylic acid, ethyl acrylate, polyethylene glycol (10 EO) stearyl alcohol ether (Steareth 10), in particular those sold by the company ALLIED COLLOIDS under the names SALCARE SC80® and SALCARE SC90® which are aqueous emulsions containing 30% of a crosslinked terpolymer of methacrylic acid, of ethyl acrylate and of steareth-10-allyl ether (40/50/10) are most particularly preferred.

(II) those comprising at least one hydrophilic unit of the olefinic unsaturated carboxylic acid type and at least one hydrophobic unit of the ($C_{10}$–$C_{30}$)alkyl ester of unsaturated carboxylic acid type.

Preferably, these polymers are chosen from those whose hydrophilic unit of the olefinic unsaturated carboxylic acid type corresponds to the monomer having the following formula (XVI):

$$CH_2=C(R_1)-C(=O)-OH \quad (XVI)$$

in which $R_1$ denotes H or $CH_3$ or $C_2H_5$, that is to say acrylic acid, methacrylic acid or ethacrylic acid units, and whose hydrophobic unit of the ($C_{10}$–$C_{30}$)alkyl ester of unsaturated carboxylic acid type corresponds to the monomer having the following formula (XVII):

$$CH_2=C(R_2)-C(=O)-OR_3 \quad (XVII)$$

in which $R_2$ denotes H or $CH_3$ or $C_2H_5$ (that is to say acrylate, methacrylate or ethacrylate units) and preferably H (acrylate units) or $CH_3$ (methacrylate units), $R_3$ denoting a $C_{10}$–$C_{30}$, and preferably $C_{12}$–$C_{22}$, alkyl radical.

($C_{10}$–$C_{30}$)alkyl esters of unsaturated carboxylic acids in accordance with the invention comprise for example lauryl acrylate, stearyl acrylate, decyl acrylate, isodecyl acrylate, dodecyl acrylate, and the corresponding methacrylates, lauryl methacrylate, stearyl methacrylate, decyl methacrylate, isodecyl methacrylate and dodecyl methacrylate.

Anionic polymers of this type are for example described and prepared according to patents U.S. Pat. Nos. 3,915,921 and 4,509,949.

Among this type of anionic associative polymers, there will be more particularly used polymers formed from a mixture of monomers comprising:

(i) essentially acrylic acid,
(ii) an ester having the formula (XVII) described above and in which $R_2$ denotes H or $CH_3$, $R_3$ denoting an alkyl radical having from 12 to 22 carbon atoms,
(iii) and a crosslinking agent, which is a well-known copolymerizable polyethylenic unsaturated monomer such as diallyl phthalate, allyl (meth)acrylate, divinylbenzene, (poly)ethylene glycol dimethacrylate and methylenebisacrylamide.

Among this type of anionic associative polymers, there will be more particularly used those consisting of 95 to 60% by weight of acrylic acid (hydrophilic unit), 4 to 40% by weight of $C_{10}$–$C_{30}$ alkyl acrylate (hydrophobic unit), and 0 to 6% by weight of crosslinking polymerizable monomer, or alternatively those consisting of 98 to 96% by weight of acrylic acid (hydrophilic unit), 1 to 4% by weight of $C_{10}$–$C_{30}$ alkyl acrylate (hydrophobic unit) and 0.1 to 0.6% by weight of crosslinking polymerizable monomer such as those described above.

Among said above polymers, the products sold by the company GOODRICH under the trade names PEMULEN TR1®, PEMULEN TR2®, CARBOPOL 1382®, and still more preferably PEMULEN TR1®, and the product sold by the company S.E.P.P.I.C. under the name COATEX SX®, are most particularly preferred according to the present invention.

(III) the terpolymers of maleic anhydride/$C_{30}$–$C_{38}$ α-olefin/alkyl maleate such as the product (maleic anhydride/$C_{30}$–$C_{38}$ α-olefin/isopropyl maleate copolymer) sold under the name PERFORMA V 1608® by the company NEWPHASE TECHNOLOGIES.

(IV) the acrylic terpolymers comprising:
(a) about 20% to 70% by weight of a carboxylic acid with α,β-monoethylenic unsaturation,
(b) about 20 to 80% by weight of a nonsurfactant monomer with α,β-monoethylenic unsaturation different from (a),
(c) about 0.5 to 60% by weight of a nonionic monourethane which is the product of the reaction of a monohydric surfactant with a monoisocyanate with monoethylenic unsaturation, such as those described in patent application EP-A-0 173 109 and more particularly that described in Example 3, namely a methacrylic acid/methyl acrylate/dimethyl metaisopropenyl benzyl isocyanate of ethoxylated (40 EO) behenyl alcohol terpolymer in 25% aqueous dispersion.

(V) the copolymers comprising among their monomers a carboxylic acid with α,β-monoethylenic unsaturation and an ester of a carboxylic acid with α,β-monoethylenic unsaturation and an oxyalkylenated fatty alcohol.

Preferably, these compounds also comprise, as monomer, an ester of a carboxylic acid with α,β-monoethylenic unsaturation and a $C_1$–$C_4$ alcohol.

By way of example of this type of compound, there may be mentioned ACULYN 22® sold by the company ROHM and HAAS, which is an oxyalkylenated stearyl methacrylate/ethyl acrylate/methacrylic acid terpolymer.

Among the associative polymers of the cationic type, there may be mentioned:

(I) the cationic associative polyurethanes the family of which has been described by the applicant in French patent application No. 0009609; it can be represented by the following general formula (XVIII):

$$R-X-(P)_n-[L-(Y)_m]_r-L'-(P')_p-X'-R' \quad (XVIII)$$

in which:
R and R', which are identical or different, represent a hydrophobic group or a hydrogen atom;

X and X', which are identical or different, represent a group containing an amine functional group carrying or otherwise a hydrophobic group, or alternatively the group L";

L, L' and L", which are identical or different, represent a group derived from a diisocyanate;

P and P', which are identical or different, represent a group containing an amine functional group carrying or otherwise a hydrophobic group;

Y represents a hydrophilic group;

r is an integer between 1 and 100, preferably between 1 and 50 and in particular between 1 and 25;

n, m and p are each, independently of the others, between 0 and 1000;

the molecule containing at least one protonated or quaternized amine functional group and at least one hydrophobic group.

In a preferred embodiment of these polyurethanes, the only hydrophobic groups are the groups R and R' at the chain ends.

A preferred family of cationic associative polyurethanes is that corresponding to the formula (XVIII) described above and in which:

R and R' both represent independently a hydrophobic group,

X, X' each represent a group L", n and p are between 1 and 1000, and

L, L', L", P, P', Y and m have the meaning indicated above.

Another preferred family of cationic associative polyurethanes is that corresponding to the formula (XVIII) above in which:

R and R' both represent independently a hydrophobic group, X, X' each represent a group L", n and p are equal to 0, and L, L', L", Y and m have the meaning indicated above.

The fact that n and p are equal to 0 means that these polymers do not contain units derived from a monomer containing an amine functional group, incorporated into the polymer during polycondensation. The protonated amine functional groups of these polyurethanes result from the hydrolysis of isocyanate functional groups, in excess, at the chain end, followed by alkylation of the primary amine functional groups formed by alkylating agents containing a hydrophobic group, that is to say compounds of the RQ or R'Q type, in which R and R' are as defined above and Q denotes a leaving group such as a halide, a sulphate and the like.

Yet another preferred family of cationic associative polyurethanes is that corresponding to the formula (Ia) above in which:

R and R' both represent independently a hydrophobic group,

X and X' both represent independently a group containing a quaternary amine, n and p are equal to zero, and L, L', Y and m have the meaning indicated above.

The number-average molecular mass of the cationic associative polyurethanes is preferably between 400 and 500 000, in particular between 1 000 and 400 000, and ideally between 1 000 and 300 000.

The expression hydrophobic group is understood to mean a radical or polymer containing a saturated or unsaturated, linear or branched hydrocarbon chain which may contain one or more heteroatoms such as P, O, N, S or a radical containing a perfluorinated or silicone chain. When it denotes a hydrocarbon radical, the hydrophobic group contains at least 10 carbon atoms, preferably from 10 to 30 carbon atoms, in particular from 12 to 30 carbon atoms, and more preferably from 18 to 30 carbon atoms.

Preferably, the hydrocarbon group is derived from a monofunctional compound.

By way of example, the hydrophobic group may be derived from a fatty alcohol such as stearyl alcohol, dodecyl alcohol, decyl alcohol. It may also denote a hydrocarbon polymer such as for example polybutadiene.

When X and/or X' denote a group containing a tertiary or quaternary amine, X and/or X' may represent one of the following formulae:

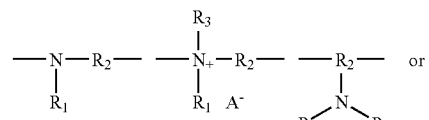

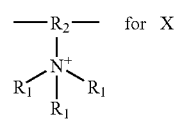 for X

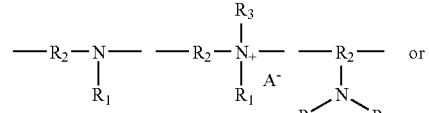

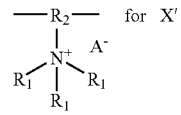 for X' in which:

$R_2$ represents a linear or branched alkylene radical having from 1 to 20 carbon atoms, containing or otherwise a saturated or unsaturated ring, or an arylene radical, it being possible for one or more of the carbon atoms to be replaced by a heteroatom chosen from N, S, O, P;

$R_1$ and $R_3$, which are identical or different, denote a linear or branched $C_1$–$C_{30}$ alkyl or alkenyl radical, an aryl radical, it being possible for at least one of the carbon atoms to be replaced by a heteroatom chosen from N, S, O, P;

$A^-$ is a physiologically acceptable counter-ion.

The groups L, L' and L" represent a group of formula:

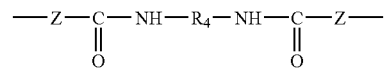

in which:

Z represents —O—, —S— or —NH—; and $R_4$ represents a linear or branched alkylene radical having from 1 to 20 carbon atoms, containing or otherwise a saturated or unsaturated ring, an arylene radical, it being possible for one or more of the carbon atoms to be replaced by a heteroatom chosen from N, S, O and P.

The groups P and P', comprising an amine functional group, may represent at least one of the following formulae:

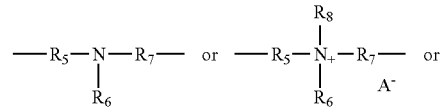

-continued

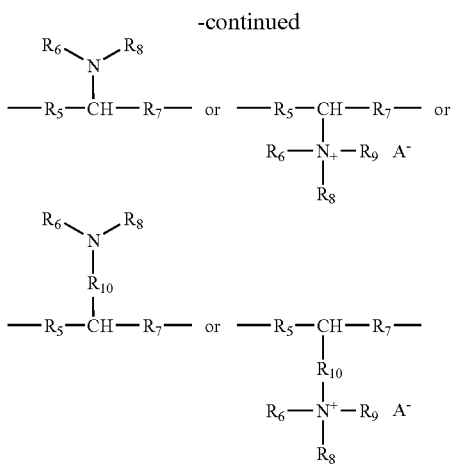

in which:

$R_5$ and $R_7$ have the same meanings as $R_2$ defined above;

$R_6$, $R_8$ and $R_9$ have the same meanings as $R_1$ and $R_3$ defined above;

$R_{10}$ represents a linear or branched alkylene group, which is optionally unsaturated and which may contain one or more heteroatoms chosen from N, O, S and P, and $A^-$ is a physiologically acceptable counter-ion.

As regards the meaning of Y, the expression hydrophilic group is understood to mean a polymeric or nonpolymeric water-soluble group.

By way of example, there may be mentioned, when polymers are not involved, ethylene glycol, diethylene glycol and propylene glycol.

In the case, in accordance with a preferred embodiment, of a hydrophilic polymer, there may be mentioned, by way of example, polyethers, sulphonated polyesters, sulphonated polyamides, or a mixture of these polymers. Preferably, the hydrophilic compound is a polyether and in particular a polyethylene oxide or a polypropylene oxide.

The cationic associative polyurethanes of formula (XVIII) which can be used according to the invention are formed from diisocyanates and from various compounds possessing functional groups containing a labile hydrogen. The functional groups containing a labile hydrogen may be alcohol functional groups, primary or secondary amine functional groups or thiol functional groups which give, after reaction with the diisocyanate functional groups, polyurethanes, polyureas and polythioureas, respectively. The term "polyurethanes" which can be used according to the present invention covers these three types of polymer, namely polyurethanes proper, polyureas and polythioureas and copolymers thereof.

A first type of compounds entering into the preparation of the polyurethane of formula (XVIII) is a compound containing at least one unit containing an amine functional group. This compound may be multifunctional, but preferably the compound is difunctional, that is to say that according to a preferred embodiment, this compound contains two labile hydrogen atoms carried for example by a hydroxyl, primary amine, secondary amine or thiol functional group. It is also possible to use a mixture of multifunctional and difunctional compounds in which the percentage of multifunctional compounds is low.

As indicated above, this compound may contain more than one unit containing an amine functional group. It is then a polymer carrying a repeat of the unit containing an amine functional group.

This type of compounds may be represented by one of the following formulae:

HZ-(P)$_n$-ZH, or

HZ-(P')$_p$-ZH, in which Z, P, P', n and p are as defined above.

By way of example of a compound containing an amine functional group, there may be mentioned N-methyldiethanolamine, N-tert-butyldiethanolamine, N-sulphoethyldiethanolamine.

The second compound entering into the preparation of the polyurethane of formula (XVIII) is a diisocyanate corresponding to the formula:

$$O=C=N-R_4-N=C=O$$

in which $R_4$ is defined above.

By way of example, there may be mentioned methylenediphenyl diisocyanate, methylenecyclohexane diisocyanate, isophorone diisocyanate, toluene diisocyanate, naphthalene diisocyanate, butane diisocyanate, hexane diisocyanate.

A third compound entering into the preparation of the polyurethane of formula (XVIII) is a hydrophobic compound intended to form the terminal hydrophobic groups of the polymer of formula (XVIII).

This compound consists of a hydrophobic group and a functional group containing a labile hydrogen, for example a hydroxyl, primary or secondary amine, or thiol functional group.

By way of example, this compound may be a fatty alcohol, such as in particular stearyl alcohol, dodecyl alcohol, decyl alcohol. When this compound contains a polymeric chain, it may be for example α-hydroxyl-hydrogenated polybutadiene.

The hydrophobic group of the polyurethane of formula (XVIII) may also result from the quaternization reaction of the tertiary amine of the compound containing at least one tertiary amine unit. Thus, the hydrophobic group is introduced by the quaternizing agent. This quaternizing agent is a compound of the RQ or R'Q type, in which R and R' are as defined above and Q denotes a leaving group such as a halide, a sulphate, and the like.

The cationic associative polyurethane may additionally comprise a hydrophilic sequence. This sequence is provided by a fourth type of compound entering into the preparation of the polymer. This compound may be multifunctional. It is preferably difunctional. It is also possible to have a mixture where the percentage of multifunctional compound is low.

The functional groups containing a labile hydrogen are alcohol, primary or secondary amine, or thiol functional groups. This compound may be a polymer terminated at the chain ends by one of these functional groups containing a labile hydrogen.

By way of example, there may be mentioned, when polymers are not involved, ethylene glycol, diethylene glycol and propylene glycol.

In the case of a hydrophilic polymer, there may be mentioned, by way of example, polyethers, sulphonated polyesters, sulphonated polyamides, or a mixture of these polymers. Preferably, the hydrophilic compound is a polyether and in particular a polyethylene oxide or a polypropylene oxide.

The hydrophilic group noted Y in formula (XVIII) is optional. Indeed, the units containing a quaternary or protonated amine functional group may suffice to provide the solubility or water-dispersibility necessary for this type of polymer in an aqueous solution.

Although the presence of a hydrophilic group Y is optional, cationic associative polyurethanes are nevertheless preferred which contain such a group.

(II) the quaternized cellulose derivatives and the polyacrylates with noncyclic amine-containing side groups.

The quaternized cellulose derivatives are in particular,
the quaternized celluloses modified by groups comprising at least one fatty chain, such as the alkyl, arylalkyl or alkylaryl groups comprising at least 8 carbon atoms, or mixtures thereof,
the quaternized hydroxyethylcelluloses modified by groups comprising at least one fatty chain, such as the alkyl, arylalkyl or alkylaryl groups comprising at least 8 carbon atoms, or mixtures thereof.

The alkyl radicals carried by the above quaternized celluloses or hydroxyethylcelluloses preferably comprise from 8 to 30 carbon atoms. The aryl radicals preferably denote phenyl, benzyl, naphthyl or anthryl groups.

There may be mentioned as examples of quaternized alkylhydroxyethylcelluloses containing $C_8$–$C_{30}$ fatty chains the products QUATRISOFT LM 200®, QUATRISOFT LM-X 529-18-A®, QUATRISOFT LM-X 529-18B® ($C_{12}$ alkyl) and QUATRISOFT LM-X 529-8® ($C_{18}$ alkyl) marketed by the company AMERCHOL and the products CRODACEL QM®, CRODACEL QL® ($C_{12}$ alkyl) and CRODACEL QS® ($C_{18}$ alkyl) marketed by the company CRODA.

Amphoteric Associative Polymers

The amphoteric associative polymers are preferably chosen from those containing at least one noncyclic cationic unit. Still more particularly, the ones that are preferred are those prepared from or comprising 1 to 20 mol % of monomer containing a fatty chain, and preferably 1.5 to 15 mol % and still more particularly 1.5 to 6 mol %, relative to the total number of moles of monomers.

The preferred amphoteric associative polymers according to the invention comprise, or are prepared by copolymerizing:

1) at least one monomer of formula (XIX) or (XX):

$$R_1-CH=C(R_2)-C(=O)-Z-(C_nH_{2n})-N^+(R_3)(R_4)R_5 \quad A^- \quad (XIX)$$

$$R_1-CH=C(R_2)-C(=O)-Z-(C_nH_{2n})-N(R_3)R_4 \quad (XX)$$

in which $R_1$ and $R_2$, which are identical or different, represent a hydrogen atom or a methyl radical, $R_3$, $R_4$ and $R_5$, which are identical or different, represent a linear or branched alkyl radical having from 1 to 30 carbon atoms,
Z represents an NH group or an oxygen atom,
n is an integer from 2 to 5,
A— is an anion derived from an organic or inorganic acid, such as a methosulphate anion or a halide such as chloride or bromide;

2) at least one monomer of formula (XXI)

$$R_6-CH=CR_7-COOH \quad (XXI)$$

in which $R_6$ and $R_7$, which are identical or different, represent a hydrogen atom or a methyl radical;
and 3) at least one monomer of formula (XXII):

$$R_6-CH=CR_7-COXR_8 \quad (XXII)$$

in which $R_6$ and $R_7$, which are identical or different, represent a hydrogen atom or a methyl radical, X denotes an oxygen or nitrogen atom and $R_8$ denotes a linear or branched alkyl radical having from 1 to 30 carbon atoms;
at least one of the monomers of formula (XIX), (XX) or (XXII) containing at least one fatty chain.

The monomers of formula (XIX) and (XX) of the present invention are preferably chosen from the group consisting of:

dimethylaminoethyl methacrylate, dimethylaminoethyl acrylate,
diethylaminoethyl methacrylate, diethylaminoethyl acrylate,
dimethylaminopropyl methacrylate, dimethylaminopropyl acrylate,
dimethylaminopropylmethacrylamide, dimethylaminopropylacrylamide, these monomers being optionally quaternized, for example with a $C_1$–$C_4$ alkyl halide or a $C_1$–$C_4$ dialkyl sulphate.

More particularly, the monomer of formula (XIX) is chosen from acrylamidopropyltrimethylammonium chloride and methacrylamidopropyltrimethylammonium chloride.

The monomers of formula (XXI) of the present invention are preferably chosen from the group consisting of acrylic acid, methacrylic acid, crotonic acid and 2-methylcrotonic acid. More particularly, the monomer of formula (XXI) is acrylic acid.

The monomers of formula (XXII) of the present invention are preferably chosen from the group consisting of $C_{12}$–$C_{22}$, and more particularly $C_{16}$–$C_{18}$ alkyl acrylates or methacrylates.

The monomers constituting the amphoteric polymers containing a fatty chain of the invention are preferably already neutralized and/or quaternized.

The ratio of the number of cationic charges/anionic charges is preferably equal to about 1.

The amphoteric associative polymers according to the invention preferably comprise from 1 to 10 mol % of the monomer containing a fatty chain (monomer of formula (XIX), (XX) or (XXII)), and preferably from 1.5 to 6 mol %.

The weight-average molecular weights of the amphoteric associative polymers according to the invention may vary from 500 to 50 000 000 and are preferably between 10 000 and 5 000 000.

The amphoteric associative polymers according to the invention may also contain other monomers such as nonionic monomers and in particular such as $C_1$–$C_4$ alkyl acrylates or methacrylates.

Amphoteric associative polymers according to the invention are for example described and prepared in patent application WO9844012.

Among the amphoteric associative polymers according to the invention, the acrylic acid/(meth)acrylamidopropyltrimethylammonium chloride/stearyl methacrylate terpolymers are preferred.

The associative polymers of the known ionic type which can be used according to the invention are preferably chosen from:

(1) celluloses modified by groups comprising at least one fatty chain;

there may be mentioned by way of example:

the hydroxyethylcelluloses modified by groups comprising at least one fatty chain such as alkyl, arylalkyl or alkylaryl groups, or mixtures thereof, and in which the alkyl groups are preferably $C_9$–$C_{22}$, such as the product NATROSOL PLUS GRADE 330 CS® ($C_{16}$ alkyls) sold by the company AQUALON, or the product BERMOCOLL EHM 100® sold by the company BEROL NOBEL, those modified by polyalkylene glycol ether of alkylphenol groups, such as the product AMERCELL POLYMER HM-1500® (polyethylene glycol (15) ether of nonylphenol) sold by the company AMERCHOL.

(2) hydroxypropylguars modified by groups comprising at least one fatty chain such as the product ESAFLOR HM 22® ($C_{22}$ alkyl chain) sold by the company LAMBERTI, the products RE210-18® ($C_{14}$ alkyl chain) and RE205-1® ($C_{20}$ alkyl chain) sold by the company RHONE POULENC.

(3) copolymers of vinylpyrrolidone and of hydrophobic monomers having a fatty chain, of which there may be mentioned by way of example:

the products ANTARON V216® or GANEX V216® (vinylpyrrolidone/hexadecene copolymer) sold by the company I.S.P.

the products ANTARON V220® or GANEX V220® (vinylpyrrolidone/eicosene copolymer) sold by the company I.S.P.

(4) copolymers of $C_1$–$C_6$ alkyl methacrylates or acrylates and of amphiphilic monomers comprising at least one fatty chain such as for example the oxyethylenated stearyl acrylate/methyl acrylate copolymer sold by the company GOLDSCHMIDT under the name ANTIL 208®.

(5) copolymers of hydrophilic methacrylates or acrylates and of hydrophobic monomers comprising at least one fatty chain such as for example the polyethylene glycol methacrylate/lauryl methacrylate copolymer.

(6) polyether-polyurethanes comprising in their chain both hydrophilic sequences which are most often of a polyoxyethylenated nature and hydrophobic sequences which may be aliphatic chains alone and/or cycloaliphatic and/or aromatic chains.

(7) polymers containing an aminoplast ether backbone possessing at least one fatty chain, such as the compounds PURE THIX® provided by the company SUD-CHEMIE.

Preferably, the polyether-polyurethanes comprise at least two lipophilic hydrocarbon chains, having from 6 to 30 carbon atoms, separated by a hydrophilic sequence, it being possible for the hydrocarbon chains to be pendent chains or chains at the end of a hydrophilic sequence. In particular, it is possible for one or more pendent chains to be envisaged. In addition, the polymer may comprise a hydrocarbon chain at one end or at both ends of a hydrophilic sequence.

The polyether-polyurethanes may be polyblocks, in particular in triblock form. The hydrophobic sequences may be at each end of the chain (for example: triblock copolymer with hydrophilic central sequence) or distributed both at the ends and in the chain (polyblock copolymer for example). These same polymers may also be in the form of graft units or may be star-shaped.

The nonionic polyether-polyurethanes containing a fatty chain may be triblock copolymers whose hydrophilic sequence is a polyoxyethylenated chain comprising from 50 to 1 000 oxyethylenated groups. Nonionic polyether-polyurethanes comprise a urethane bond between the hydrophilic sequences, hence the origin of the name.

By extension, those whose hydrophilic sequences are linked by other chemical bonds to the lipophilic sequences are also included among the nonionic polyether-polyurethanes containing a fatty chain.

By way of examples of nonionic polyether-polyurethanes containing a fatty chain which can be used in the invention, it is also possible to use Rhéolate 205® containing a urea functional group sold by the company RHEOX or the Rhéolates® 208, 204 or 212, as well as Acrysol RM 184®.

There may also be mentioned the product ELFACOS T210® containing a $C_{12-14}$ alkyl chain and the product ELFACOS T212® containing a $C_{18}$ alkyl chain from AKZO.

The product DW 1206B® from RHOM & HAAS containing a $C_{20}$ alkyl chain and with a urethane bond, sold at 20% dry matter content in water, may also be used.

It is also possible to use solutions or dispersions of these polymers in particular in water or in an aqueous alcoholic medium. By way of example of such polymers, there may be mentioned Rhéolate® 255, Rhéolate® 278 and Rhéolate® 244 sold by the company RHEOX. It is also possible to use the product DW 1206F and DW 1206J provided by the company ROHM & HAAS.

The polyether-polyurethanes which can be used according to the invention are in particular those described in the article by G. Fonnum, J. Bakke and Fk. Hansen-Colloid Polym. Sci 271, 380–389 (1993).

Still more particularly it is preferable to use a polyether-polyurethane which can be obtained by polycondensation of at least three compounds comprising (i) at least one polyethylene glycol comprising from 150 to 180 mol of ethylene oxide, (ii) stearyl alcohol or decyl alcohol and (iii) at least one diisocyanate.

Such polyether-polyurethanes are sold in particular by the company ROHM & HAAS under the names Aculyn 46® and Aculyn 44® [ACULYN 46® is a polycondensate of polyethylene glycol containing 150 or 180 mol of ethylene oxide, stearyl alcohol and methylenebis(4-cyclohexyl isocyanate) (SMDI), at 15% by weight in a matrix of maltodextrin (4%) and water (81%); ACULYN 44® is a polycondensate of polyethylene glycol containing 150 or 180 mol of ethylene oxide, decyl alcohol and methylenebis(4-cyclohexyl isocyanate) (SMDI), at 35% by weight in a mixture of propylene glycol (39%) and water (26%)].

According to a third preferred embodiment, the composition according to the present invention additionally contains at least one surfactant.

The surfactants which are suitable for carrying out the present invention are in particular the following:

(i) Anionic Surfactant(s):

By way of example of anionic surfactants which can be used, alone or as mixtures, in the context of the present invention there may be mentioned in particular (nonlimiting list) the salts (in particular alkali metal, especially sodium, salts, ammonium salts, amine salts, amino alcohol salts or magnesium salts) of the following compounds: alkyl sulphates, alkyl ether sulphates, alkylamido ether sulphates, alkylarylpolyether sulphates, monoglyceride sulphates; alkyl sulphonates, alkyl phosphates, alkylamidesulphonates, alkyl aryl sulphonates, α-olefinsulphonates, paraffinsulphonates; ($C_6$–$C_{24}$)alkyl sulphosuccinates, ($C_6$–$C_{24}$)alkyl ether sulphosuccinates, ($C_6$–$C_{24}$)alkylamide sulphosuccinates;

($C_6$–$C_{24}$)alkyl sulphoacetates; ($C_6$–$C_{24}$)acyl sarcosinates and ($C_6$–$C_{24}$)acyl glutamates. It is also possible to use ($C_6$–$C_{24}$)alkyl polyglycoside carboxylic esters such as alkyl glucoside citrates, alkyl polyglycoside tartrate and alkyl polyglycoside sulphosuccinates, alkyl sulphosuccinamates; acyl isethionates and N-acyltaurates, the alkyl or acyl radical of all these various compounds preferably comprising from 12 to 20 carbon atoms, and the aryl radical preferably denoting a phenyl or benzyl group. Among the anionic surfactants which can still be used, there may also be mentioned the salts of fatty acids such as the salts of oleic, ricinoleic, palmitic and stearic acids, the acids of copra oil or of hydrogenated copra oil; the acyllactylates whose acyl radical comprises 8 to 20 carbon atoms. It is also possible to use the alkyl D-galactoside uronic acids and their salts, the polyoxyalkylenated ($C_6$–$C_{24}$)alkyl ether carboxylic acids, the polyoxyalkylenated ($C_6$–$C_{24}$)alkylaryl ether carboxylic acids, the polyoxyalkylenated ($C_6$–$C_{24}$)alkyl amido ether carboxylic acids and their salts, in particular those comprising from 2 to 50 alkylene, in particular ethylene, oxide groups, and mixtures thereof.

(ii) Additional Nonionic Surfactant(s):

These additional surfactants are different from the monoglycerolated or polyglycerolated nonionic surfactants used as essential agents in the compositions according to the invention.

The nonionic surfactants themselves are also compounds which are well known per se (in this respect see especially the "Handbook of Surfactants" by M. R. Porter, published by Blackie & Son (Glasgow and London), 1991, pp. 116–178) and, in the context of the present invention, their nature does not assume any critical character. They can thus be chosen especially from (nonlimiting list) alcohols, alpha-diols or polyethoxylated or polypropoxylated alkylphenols which have a fatty chain containing, for example, 8 to 18 carbon atoms, it being possible for the number of ethylene oxide or propylene oxide groups to range especially from 2 to 50. The copolymers of ethylene oxide and propylene oxide and the condensates of ethylene oxide and propylene oxide with fatty alcohols may also be mentioned; the polyethoxylated fatty amides preferably containing from 2 to 30 mol of ethylene oxide, the polyglycerolated fatty amides containing on average 1 to 5 glycerol groups and in particular 1.5 to 4; the oxyethylenated fatty acid esters of sorbitan containing from 2 to 30 mol of ethylene oxide; the fatty acid esters of sucrose, the fatty acid esters of polyethylene glycol, alkylpolyglycosides, the N-alkylglucamine derivatives, amine oxides such as the oxides of (C10–C14)alkylamines or the N-acylaminopropylmorpholine oxides.

(iii) Amphoteric or Zwitterionic Surfactant(s):

The amphoteric or zwitterionic surfactants, the nature of which is not of critical importance in the context of the present invention, may be especially (nonlimiting list) derivatives of aliphatic secondary or tertiary amines in which the aliphatic radical is a linear or branched chain containing 8 to 18 carbon atoms and containing at least one water-solubilizing anionic group (for example carboxylate, sulphonate, sulphate, phosphate or phosphonate); ($C_8$–$C_{20}$) alkylbetaines, sulphobetaines, ($C_8$–$C_{20}$)alkylamido($C_1$–$C_6$) alkylbetaines or ($C_8$–$C_{20}$)alkylamido($C_1$–$C_6$)alkylsulphobetaines may further be mentioned.

Among the amine derivatives, there may be mentioned the products sold under the name MIRANOL, as described in patents U.S. Pat. No. 2,528,378 and U.S. Pat. No. 2,781,354 and classified in the CTFA dictionary, 3rd edition, 1982, under the names Amphocarboxyglycinates and Amphocarboxypropionates having the respective structures:

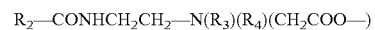

in which: R2 denotes an alkyl radical of an acid $R_2$—COOH present in hydrolysed copra oil, a heptyl, nonyl or undecyl radical, R3 denotes a beta-hydroxyethyl group and $R_4$ a carboxymethyl group;
and

in which:
B represents —$CH_2CH_2OX'$, C represents —$(CH_2)_z$—Y', with z=1 or 2,
X' denotes the —$CH_2CH_2$—COOH group or a hydrogen atom
Y' denotes —COOH or the radical —$CH_2$—CHOH—$SO_3H$
$R_2'$ denotes an alkyl radical of an acid $R_9$ —COOH present in copra oil or in hydrolysed linseed oil, an alkyl radical, especially $C_7$, $C_9$, $C_{11}$ or $C_{13}$, a $C_{17}$ alkyl radical and its iso form or an unsaturated $C_{17}$ radical.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauro amphodipropionic acid, Cocoamphodipropionic acid.

By way of example, there may be mentioned the cocoamphodiacetate marketed under the trade name MIRANOL® C2M concentrated by the company RHODIA CHIMIE.

(iv) Cationic Surfactants:

Among the cationic surfactants, there may be mentioned in particular (nonlimiting list): the salts of optionally polyoxyalkylenated primary, secondary or tertiary amines; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives or amine oxides of a cationic nature.

The quantities of surfactants present in the composition according to the invention may vary from 0.01 to 40% and preferably from 0.5 to 30% of the total weight of the composition.

The composition of the present invention may additionally comprise one or more additional oxidation bases which are conventionally used in oxidation dyeing other than the para-phenylenediamines of formula I. By way of example, these additional oxidation bases are chosen from phenylenediamines, bisphenylalkylenediamines, para-aminophenols, ortho-aminophenols, heterocyclic bases other than the heterocyclic para-phenylenediamines of formula I and their addition salts.

Among the para-phenylenediamines, there may be mentioned, by way of example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine and their addition salts with an acid.

Among the para-phenylenediamines mentioned above, there are particularly preferred para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and their addition salts with an acid.

Among the bisphenylalkylenediamines, there may be mentioned, by way of example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and their addition salts.

Among the para-aminophenols, there may be mentioned, by way of example, para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and their addition salts with an acid.

Among the ortho-aminophenols, there may be mentioned, by way of example, 2-aminophenol, 2-amino-5-methylphenol, 2-amino-6-methylphenol, 5-acetamido-2-aminophenol, and their addition salts.

Among the heterocyclic bases, there may be mentioned, by way of example, pyridine derivatives, pyrimidine derivatives and pyrazole derivatives.

Among the pyridine derivatives, there may be mentioned the compounds described for example in patents GB 1 026 978 and GB 1 153 196, such as 2,5-diaminopyridine, 2-(4-methoxyphenyl)amino-3-aminopyridine, 3,4-diaminopyridine, and their addition salts.

Other pyridine oxidation bases useful in the present invention are the oxidation bases 3-aminopyrazolo[1,5-a]pyridines or their addition salts which are described, for example, in patent application FR 2801308. By way of example, there may be mentioned pyrazolo[1,5-a]pyridin-3-ylamine; 2-acetylaminopyrazolo[1,5-a]pyridin-3-ylamine; 2-morpholin-4-ylpyrazolo[1,5-a]pyridin-3-ylamine; 3-aminopyrazolo[1,5-a]pyridine-2-carboxylic acid; 2-methoxypyrazolo[1,5-a]pyridin-3-ylamino; (3-aminopyrazolo[1,5-a]pyridin-7-yl)methanol; 2-(3-aminopyrazolo[1,5-a]pyridin-5-yl)ethanol; 2-(3-aminopyrazolo[1,5-a]pyridin-7-yl)ethanol; (3-aminopyrazolo[1,5-a]pyridin-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyridin-3-ylamine; pyrazolo[1,5-a]pyridine-3,5-diamine; 5-morpholin-4-ylpyrazolo[1,5-a]pyridin-3-ylamine; 2-[(3-aminopyrazolo[1,5-a]pyridin-5-yl)(2-hydroxyethyl)amino]ethanol; 2-[(3-aminopyrazolo[1,5-a]pyridin-7-yl)(2-hydroxyethyl)amino]ethanol, 3-aminopyrazolo[1,5-a]pyridin-5-ol; 3-aminopyrazolo[1,5-a]pyridin-4-ol, 3-aminopyrazolo[1,5-a]pyridin-6-ol; 3-aminopyrazolo[1,5-a]pyridin-7-ol; and their addition salts.

Among the pyrimidine derivatives, there may be mentioned the compounds described for example in patents DE 2 359 399; JP 88-169 571; JP 05-63124; EP 0 770 375 or patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and their addition salts and their tautomeric forms, when a tautomeric equilibrium exists.

Among the pyrazole derivatives, there may be mentioned the compounds described in patents DE 3 843 892, DE 4 133 957 and patent applications WO 94/08969, WO 94/08970, FR-A-2 733 749 and DE 195 43 988 such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(P-hydroxyethyl)amino-1-methylpyrazole, and their addition salts.

The additional oxidation base(s) present in the composition of the invention are generally present in a quantity of between 0.001 to 20% by weight approximately of the total weight of the dyeing composition, preferably between 0.005 and 6%.

The composition according to the invention preferably contains, one or more additional couplers conventionally used for dyeing keratinous fibres. Among these couplers, there may be mentioned in particular meta-phenylenediamines, meta-diphenols, naphthalene couplers, heterocyclic couplers and their addition salts.

By way of example, there may be mentioned 1,3-dihydroxybenzene, 1,3-dihydroxy-2-methylbenzene, 4-chloro-1,3-dihydroxybenzene, 2,4-diamino-1-(P-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(p-hydroxyethylamino)toluene and their addition salts.

In the composition of the present invention, the coupler(s) are generally present in a quantity of between 0.001 and 20% by weight approximately of the total weight of the dyeing composition, preferably ranging from 0.005 to 6%.

In general, the addition salts of the oxidation bases and couplers which can be used in the context of the invention are in particular chosen from the addition salts with an acid such as the hydrochlorides, hydrobromides, sulphates, citrates, succinates, tartrates, lactates, tosylates, benzenesulphonates, phosphates and acetates and the addition salts with a base such as sodium hydroxide, potassium hydroxide, ammonium hydroxide, amines or alkanolamines.

The dyeing composition in accordance with the invention may additionally contain one or more additional direct dyes, other than the cationic direct dyes comprising a heterocycle group useful for the invention which may be chosen in particular from neutral, acidic or cationic nitro dyes of the benzene series, neutral, acidic or cationic azo direct dyes, neutral, acidic or cationic quinone and in particular anthraquinone direct dyes, azine direct dyes, triarylmethane direct dyes, indoamine direct dyes and natural direct dyes.

Among the benzene direct dyes which can be used according to the invention, the following compounds may be mentioned without limitation:
1,4-diamino-2-nitrobenzene,
1-amino-2 nitro-4-β-hydroxyethylaminobenzene
1-amino-2 nitro-4-bis(β-hydroxyethyl)aminobenzene
1,4-bis(β-hydroxyethylamino)-2-nitrobenzene
1-β-hydroxyethylamino-2-nitro-4-bis-(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris-(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis-(β-hydroxyethyl)amino-3-nitrobenzene
1-β-hydroxyethylamino-2-nitrobenzene
1-hydroxy-4-β-hydroxyethylamino-3-nitrobenzene.

There may also be mentioned, among the azo direct dyes, the following dyes, which are described in COLOUR INDEX INTERNATIONAL 3rd edition:

Disperse Red 17
Acid Yellow 9
Acid Black 1
Basic Red 76
Basic Yellow 57
Basic Brown 16
Acid Yellow 36
Acid Orange 7
Acid Red 33
Acid Red 35
Basic Brown 17
Acid Yellow 23
Acid Orange 24
Disperse Black 9.

There may also be mentioned 1-(4'-aminodiphenylazo)-2-methyl-4bis(β-hydroxyethyl)aminobenzene and 4-hydroxy-3-(2-methoxyphenylazo)-1-naphtalenesulphonic acid.

Among the quinone direct dyes, the following dyes may be mentioned:
Disperse Red 15
Solvent Violet 13
Acid Violet 43
Disperse Violet 1
Disperse Violet 4
Disperse Blue 1
Disperse Violet 8
Disperse Blue 3
Disperse Red 11
Acid Blue 62
Disperse Blue 7
Basic Blue 22
Disperse Violet 15
Basic Blue 99 and the following compounds:
1-N-methylmorpholiniumpropylamino-4-hydroxyanthraquinone
1-aminopropylamino-4-methylaminoanthraquinone
1-aminopropylaminoanthraquinone
5-p-hydroxyethyl-1,4-diaminoanthraquinone
2-aminoethylaminoanthraquinone
1,4-bis(β,γ-dihydroxypropylamino)anthraquinone.

Among the azine dyes, the following compounds may be mentioned:
Basic Blue 17
Basic Red 2.

Among the triarylmethane dyes which can be used according to the invention, the following compounds may be mentioned:
Basic Green 1
Acid blue 9
Basic Violet 3
Basic Violet 14
Basic Blue 7
Acid Violet 49
Basic Blue 26
Acid Blue 7

Among the indoamine dyes which can be used according to the invention, the following compounds may be mentioned:
2-β-hydroxyethylamino-5-[bis(β-4'-hydroxyethyl)amino]anilino-1,4-benzoquinone
2-β-hydroxyethylamino-5-(2'-methoxy-4'-amino)anilino-1,4-benzoquinone
3-N(2'-chloro-4'-hydroxy)phenylacetylamino-6-methoxy-1,4-benzoquinoneimine 3-N(3'-chloro-4'-methylamino)phenylureido-6-methyl-1,4-benzoquinoneimine 3-[4'-N-(ethylcarbamylmethyl)amino]phenylureido-6-methyl-1,4-benzoquinoneimine Among the natural direct dyes which can be used according to the invention, there may be mentioned lawsone, juglone, alizarin, purpurin, carminic acid, kermesic acid, purpurogallin, protocatechaldehyde, indigo, isatin, curcumin, spinulosin and apigenidin. It is also possible to use extracts or decoctions containing these natural dyes and in particular henna-based poultices or extracts.

The additional direct dye(s) preferably represent from 0.001 to 20% by weight approximately of the total weight of the ready-to-use composition and still more preferably from 0.005 to 10% by weight approximately.

The composition according to the invention may also contain at least one hydroxylated solvent, such as in particular ethanol, propylene glycol, glycerol, polyol monoethers, benzyl alcohol.

It may also contain a nonhydroxylated solvent.

The hydroxylated solvents and the nonhydroxylated solvents are preferably present in proportions preferably between 1 and 40% by weight approximately relative to the total weight of the dyeing composition, and still more preferably between 5 and 30% by weight approximately.

The dyeing composition in accordance with the invention may also contain various adjuvants conventionally used in hair dyeing compositions, such as antioxidants, penetrating agents, sequestering agents, perfumes, buffers, dispersing agents, conditioning agents such as for example modified or unmodified, volatile or nonvolatile silicones, film-forming agents, ceramides, preservatives and opacifying agents.

The above adjuvants are generally present in a quantity, for each of them, of between 0.01 and 20% by weight relative to the weight of the composition.

Of course, persons skilled in the art will be careful to choose this or these optional additional compounds such that the advantageous properties intrinsically attached to the oxidation dyeing composition in accordance with the invention are not, or not substantially, impaired by the addition(s) envisaged.

The pH of the dyeing composition in accordance with the invention is generally between 3 and 12 approximately, and preferably between 5 and 11 approximately. It may be adjusted to the desired value by means of acidifying or alkalinizing agents customarily used in dyeing keratinous fibres or with the aid of conventional buffering systems.

Among the acidifying agents, there may be mentioned, by way of example, inorganic or organic acids such as hydrochloric acid, orthophosphoric acid, sulphuric acid, carboxylic acids such as acetic acid, tartaric acid, citric acid, lactic acid and sulphonic acids.

Among the alkalinizing agents, there may be mentioned, by way of example, ammonium hydroxide, alkali metal carbonates, alkanolamines such as mono-, di- and triethanolamines and the derivatives thereof, sodium or potassium hydroxides and the compounds of the following formula (XXIII):

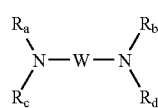

(XXIII)

in which W is a propylene residue optionally substituted with a hydroxyl group or a $C_1$–$C_4$ alkyl radical; $R_a$, $R_b$, $R_c$ and $R_d$, which may be identical or different, represent a hydrogen atom, a $C_1$–$C_4$ alkyl radical or a $C_1$–$C_4$ hydroxyalkyl radical.

The dyeing composition according to the invention may be provided in various forms, such as in the form of liquids, creams or gels, or in any other appropriate form for dyeing keratinous fibres, and in particular human hair.

The method of the present invention is a method in which the composition according to the present invention, as defined above, is applied to the fibres, and the colour is developed using an oxidizing agent. The colour may be developed at acidic, neutral or alkaline pH and the oxidizing agent may be added to the composition of the invention just at the time of use or it can be used from an oxidizing composition containing it, applied simultaneously or sequentially with the composition of the invention.

According to a particular embodiment, the composition according to the present invention is mixed, preferably at the time of use, with a composition containing, in a medium appropriate for dyeing, at least one oxidizing agent, this oxidizing agent being present in a sufficient quantity to develop a colour. The mixture obtained is then applied to the keratinous fibres. After an exposure time of 3 to 50 minutes approximately, preferably 5 to 30 minutes approximately, the keratinous fibres are rinsed, washed with shampoo, rinsed again and then dried.

The cationic direct dye(s) used according to the invention is (are) present either in the composition containing the cationic pyrrolidine oxidation base(s) or in the oxidizing composition, or in both, or in another composition which is mixed with the preceding compositions at the time of use.

The oxidizing agents conventionally used for the oxidation dyeing of keratinous fibres are, for example, hydrogen peroxide, urea peroxide, alkali metal bromates, persalts such as perborates and persulphates, peracids and the oxidase enzymes, among which there may be mentioned peroxidases, oxidoreductases with 2 electrons such as uricases and oxygenases with 4 electrons such as laccases. Hydrogen peroxide is particularly preferred.

The oxidizing composition may also contain various adjuvants conventionally used in hair dyeing compositions and as defined above.

The pH of the oxidizing composition containing the oxidizing agent is such that, after mixing with the dyeing composition, the pH of the resulting composition applied to keratinous fibres preferably varies between 3 and 12 approximately, and still more preferably between 5 and 11. It may be adjusted to the desired value by means of acidifying or alkalinizing agents customarily used for dyeing keratinous fibres and as defined above.

The ready-to-use composition which is finally applied to the keratinous fibres may be provided in various forms, such as in the form of liquids, creams or gels, or in any other form appropriate for dyeing keratinous fibres, and in particular human hair.

The subject of the invention is finally a multicompartment device or dyeing "kit" in which a first compartment contains the dyeing composition defined above and a second compartment contains an oxidizing composition. This device may equipped with means which make it possible to deliver the desired mixture to the hair, such as the devices described in patent FR-2 586 913 in the name of the applicant.

Another device is a device in which a first compartment contains a composition comprising at least one cationic tertiary para-phenylenediamine containing a pyrrolidine ring, a second compartment contains a composition containing at least one cationic direct dye comprising at least one heterocyclic group and a third compartment contains an oxidizing composition.

Using these devices, it is possible to dye keratinous fibres using a method which comprises mixing a dyeing composition in accordance with the invention as such or produced by mixing two compositions at the time of use with an oxidizing agent as defined above, and applying the mixture obtained to the keratinous fibres for a time sufficient to develop the desired colour.

The following examples serve to illustrate the invention without, however, exhibiting a limiting character.

DETAILED DESCRIPTION

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Dyeing Composition: (Expressed in Grams)

| | |
|---|---|
| Oleyl alcohol | 6 |
| Oleic acid | 3 |
| Polyglycerolenated oleyl alcohol containing 2 moles of glycerol | 6 |
| Polyglycerolenated oleyl alcohol containing 6 moles of glycerol | 6 |
| Diethylaminopropyl laurylaminosuccinamate, sodium salt | 3 |
| Oxyethylenated oleyl amine containing 2 moles of ethylene oxide | 7 |
| Monoethanolamide of alkyl ether carboxylic acid containing 2 moles of ethylene oxide | 10 |
| Ammonium acetate | 20 |
| Propylene glycol | 20 |
| Dilinoleic acid | 1.5 |
| Reducing agents, antioxidants | 0.915 |
| Sequestrants | 1 |
| 1,3-Dihydroxybenzene (resorcinol) | 0.085 |
| [1-(4-Aminophenyl)pyrrolidin-3-yl]trimethylammonium chloride | 1.0 |
| 2-Methyl-5-aminophenol | 0.5 |
| Niacinamide | 0.2 |
| Perfume | qs |
| Ammonium hydroxide (containing 20.5% ammonia) | 10.2 |
| Demineralized water qs | 100 |

At the time of application, 50 g of the dye composition of Example 1 is mixed on a weight for weight basis with 20-volumes aqueous hydrogen peroxide solution, and 0.2 g of Basic Red 51 is then added to the mixture obtained.

The mixture obtained is applied for 30 minutes to grey hair which is 90% white. A purplish brownish red coloration is obtained on this hair after rinsing, shampooing and drying.

EXAMPLE 2

Dyeing Composition: (Expressed in Grams)

| | |
|---|---|
| Oleyl alcohol | 4 |
| Oleic acid | 5 |
| Polyglycerolenated oleyl alcohol containing 2 moles of glycerol | 4 |
| Polyglycerolenated lauryl alcohol containing 4 moles of glycerol | 3.6 |
| Oxyethylenated rape acid amide containing 4 moles of ethylene oxide | 8 |
| Oxyethylenated oleyl amine containing 2 moles of ethylene oxide | 4 |
| Oxyethylenated decyl alcohol containing 3 moles of ethylene oxide | 2.7 |
| Propylene glycol | 20 |
| Adipic acid | 1.3 |
| Reducing agents, antioxidants | 0.63 |
| Sequestrant | 1 |
| 3-[1-(4-aminophenyl)pyrrolidin-3-yl]-1-methyl-3H-imidazol-1-ium chloride | 0.8 |
| 5N(β-hydroxyethyl)amino-2-methylphenol | 0.4 |
| Pure monoethanolamine | 2 |
| Panthenol | 0.1 |
| Perfume | qs |
| Ammonium hydroxide (containing 20.5% ammonia) | 10 |
| Demineralized water qs | 100 |

At the time of application, 50 g of the dye composition of Example 2 is mixed on a weight for weight basis with 20-volumes aqueous hydrogen peroxide solution, and 0.2 g of Basic Red 51 is then added to the mixture obtained.

The mixture obtained is applied for 30 minutes to grey hair which is 90% white. A deep purplish red coloration is obtained on this hair after rinsing, shampooing and drying.

What is claimed is:

1. A dyeing composition for dyeing keratinous fibres comprising, in an appropriate dyeing medium, at least one cationic tertiary para-phenylenediamine comprising a pyrrolidine ring, and a dicationic diazo dye of general formula Vb

in which $W_7$ and $W_9$ represent independently of each other a heteroaromatic radical represented by formulae (C) and (D) below:

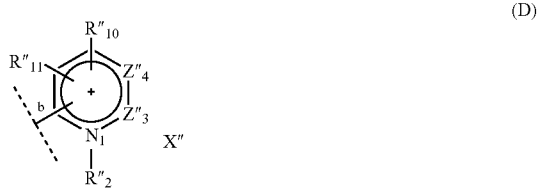

$W_8$ represents a carbon-based aromatic, pyridine or pyridazinyl group of formula (E)

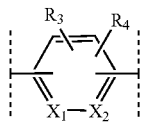
(E)

in which formulae (C), (D), (E):
X"$_1$ represents a nitrogen atom or a radical CR"$_5$
X"$_2$ represents a nitrogen atom or a radical CR"$_6$
Z"$_1$ represents an oxygen or sulphur atom or a radical NR"$_8$,
Z"$_2$ represents a nitrogen atom or a radical CR"$_9$,
Z"$_3$ represents a nitrogen atom or a radical CR"$_{12}$,
Z"$_4$ represents a nitrogen atom or a radical CR"$_{13}$,
the bond a of the 5-membered cationic ring of formula (C) is linked to the azo group of formula (Vb),
the bond b of the 6-membered cationic ring of formula (D) is linked to the azo group of formula (Vb)
R"$_3$, R"$_4$, R"$_5$, R"$_6$, R"$_7$, R"$_9$, R"$_{10}$, R"$_{11}$, R"$_{12}$ and R"$_{13}$, represent, together or independently of each other, a hydrogen atom, a linear or branched, saturated or unsaturated $C_1$–$C_{16}$ hydrocarbon-based chain, which can form one or more 3- to 6-membered carbon-based rings, one or more carbon atoms of the carbon-based chain of which may be replaced with an oxygen, nitrogen or sulphur atom or with an $SO_2$ group, and the carbon atoms of which may be, independently of each other, substituted with one or more halogen atoms; R"$_3$, R"$_4$, R"$_5$, R"$_6$, R"$_7$, R"$_9$, R"$_{10}$, R"$_{11}$, R"$_{12}$ and R"$_{13}$ not comprising a peroxide bond or diazo or nitroso radicals,
R"$_7$ with R"$_9$, R"$_{10}$ with R"$_{11}$ and R"$_{12}$ with R"$_{13}$ can form a carbon-based aromatic ring, such as a phenyl,
X" is an organic or mineral anion; and
wherein said cationic tertiary paraphenylenediamine containing a pyrrolidine ring corresponds to formula I:

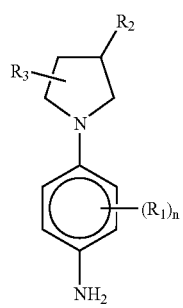
(I)

in which
n varies from 0 to 4, it being understood that when n is greater than or equal to 2, then the radicals $R_1$ may be identical or different,
$R_1$ represents a halogen atom; a saturated or unsaturated, aliphatic or alicylic, $C_1$–$C_6$ hydrocarbon chain, it being possible for the chain to contain one or more oxygen, nitrogen, silicon or sulphur atoms or an $SO_2$ group, and it being possible for the chain to be substituted with one or more hydroxyl or amino radicals; an onium radical Z, the radical $R_1$ not containing a peroxide bond, or diazo, nitro or nitroso radicals,
$R_2$ represents an onium radical Z or a radical —X—C=NR$_8$—NR$_9$R$_{10}$ in which X represents an oxygen atom or a radical —NR$_{11}$ and R$_8$, R$_9$, R$_{10}$ and R$_{11}$ represent a hydrogen atom, a $C_1$–$C_4$ alkyl radical or a $C_1$–$C_4$ hydroxyalkyl radical,
$R_3$ represents a hydrogen atom or a hydroxyl radical.

2. The composition of claim 1, wherein the dye is selected from the group consisting of:
1,3-dimethyl-2-[4-(1,3-dimethyl(imidazol-1-ium)-2-ylazo)phenylazo]imidazol-1-ium
1,4-dimethyl-3-[4-(1,4-dimethyl(triazol-2-ium)-3-ylazo)phenylazo]triazol-2-ium
1-methyl-2-[4-(1-methyl(pyridin-1-ium)-2-ylazo)phenylazo]pyridin-1-ium
1-methyl-3-[4-(1-methyl(pyridin-1-ium)-3-ylazo)phenylazo]pyridin-1-ium
1,3-dimethyl-2-[4-(3-methyl(thiazol-3-ium)-2-ylazo)phenylazo]imidazol-1-ium
1,4-dimethyl-3-[4-(3-methyl(thiazol-3-ium)-2-ylazo)phenylazo]triazol-2-ium
1,3-dimethyl-2-[4-(1,4-dimethyl(triazol-2-ium)-3-ylazo)phenylazo]imidazol-1-ium
1-methyl-2-[4-(3-methyl(thiazol-3-ium)-2-ylazo)phenylazo]pyridin-1-ium
1-methyl-3-[4-(3-methyl(thiazol-3-ium)-2-ylazo)phenylazo]pyridin-1-ium
1,3-dimethyl-2-[4-(1-methyl(pyridin-1-ium)-2-ylazo)phenylazo]imidazol-1-ium
1,4-dimethyl-3-[4-(1-methyl(pyridin-1-ium)-2-ylazo)-phenylazo]-triazol-2-ium
1,3-dimethyl-2-[4-(1-(2-hydroxyethyl)(pyridin-1-ium)-2-ylazo)phenylazo]imidazol-1-ium
1,4-dimethyl-3-[4-(1-(2-hydroxyethyl)(pyridin-1-ium)-2-ylazo)phenylazo]triazol-2-ium
1,3-dimethyl-2-[4-(1-methyl(pyridin-1-ium)-3-ylazo)phenylazo]imidazol-1-ium
1,4-dimethyl-3-[4-(1-methyl(pyridin-1-ium)-3-ylazo)phenylazo]triazol-2-ium
1,3-dimethyl-2-[4-(1-(2-hydroxyethyl)(pyridin-1-ium)-3-ylazo)phenylazo]imidazol-1-ium
1,4-dimethyl-3-[4-(1-(2-hydroxyethyl)(pyridin-1-ium)-3-ylazo)phenylazo]triazol-2-ium
1,3-dimethyl-2-[4-(1,3-dimethyl(imidazol-1-ium)-2-ylazo)-3-methoxyphenylazo]imidazol-1-ium
1,3-dimethyl-2-[4-(1,4-dimethyl(triazol-2-ium)-3-ylazo)-3-methoxyphenylazo]imidazol-1-ium
1,3-dimethyl-2-[4-(1-methyl(pyridin-1-ium)-2-ylazo)-3-methoxyphenylazo]imidazol-1-ium.

3. A dyeing composition for dyeing keratinous fibres comprising, in an appropriate dyeing medium, at least one cationic tertiary para-phenylenediamine comprising a pyrrolidine ring, and a monocationic monoazo dye of formula (Vk)

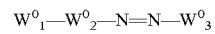

in which
W°$_1$ represents a 5-, 6-, 7- or 8-membered heterocycle of formula (II°) below

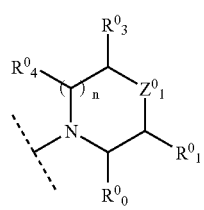
(II°)

$W^0_2$ represents a divalent carbon-based aromatic, pyridine or pyridazine group of formula (III°) below

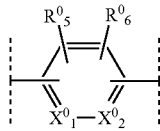

(III°)

$W^0_3$ represents a cationic heteroaromatic radical represented by formula (IV°) below:

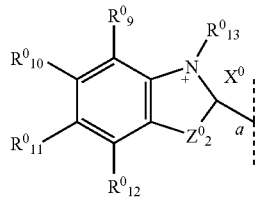

(IV°)

in which formulae (II°), (III°) and (IV°):
n=0, 1, 2 or 3, it being understood that when n is greater than or equal to 2, then the radicals $R^0_4$ may be identical or different,
$X^0_1$ represents a nitrogen atom or a radical $CR^0_7$,
$X^0_2$ represents a nitrogen atom or a radical $CR^0_8$,
$Z^0_1$ represents a radical $CHR^0_2$, an oxygen or sulphur atom or a radical $NR^0_{14}$,
$Z^0_2$ represents an oxygen or sulphur atom or a radical $NR^0_{15}$
$R^0_0$, $R^0_1$, $R^0_2$, $R^0_3$, $R^0_4$, $R^0_5$, $R^0_6$, $R^0_7$, $R^0_8$, $R^0_9$, $R^0_{10}$, $R^0_{11}$ and $R^0_{12}$, which may be identical or different, represent a hydrogen atom, a linear or branched $C_1$–$C_{10}$ hydrocarbon-based chain, which can form one or more 3- to 6-membered carbon-based rings, and which may be saturated or unsaturated, one or more carbon atoms of the carbon-based chain of which may be replaced with an oxygen, nitrogen or sulphur atom or with an $SO_2$ group, and the carbon atoms of which may be, independently of each other, substituted with one or more halogen atoms; $R^0_0$, $R^0_1$, $R^0_2$, $R^0_3$, $R^0_4$, $R^0_5$, $R^0_6$, $R^0_7$, $R^0_8$, $R^0_9$, $R^0_{11}$ and $R^0_{12}$ not comprising a peroxide bond or diazo or nitroso radicals,
$R^0_{14}$ represents a hydrogen atom, a linear or branched C1–C10 hydrocarbonbased chain, which can form one or more 3- to 6-membered carbon-based rings, and which may be saturated or unsaturated, one or more carbon atoms of the carbon-based chain of which may be replaced with an oxygen, nitrogen or sulphur atom or with an $SO_2$ group, and the carbon atoms of which may be, independently of each other, substituted with one or more halogen atoms, $R^0_{14}$ not comprising a peroxide. bond or diazo or nitroso radicals; it being understood that the said oxygen, nitrogen and sulphur atoms are not directly linked to the nitrogen atom bearing the radical $R^0_{14}$,
$R^0_5$ with $R^0_6$ can form a carbon-based aromatic ring, such as a phenyl,
$R^0_{13}$ and $R^0_{15}$, which may be identical or different, represent a $C_1$–$C_8$ alkyl radical, optionally substituted with one or more radicals chosen from the group consisting of a hydroxyl, a $C_1$–$C_2$ alkoxy, a $C_2$–$C_4$ (poly)hydroxyalkoxy, an amino, a $C_1$–$C_2$ (di)alkylamino, a carboxyl, a sulphonic or an optionally substituted phenyl radical;
the bond a of the cationic ring of formula (IV) is linked to the azo group of formula (I);
$X^0$ is an organic or mineral anion; and
wherein said cationic tertiary paraphenylenediamine containing a pyrrolidine ring corresponds to formula I:

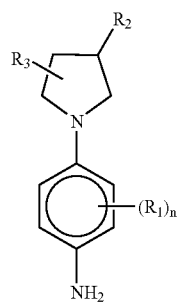

(I)

in which
n varies from 0 to 4, it being understood that when n is greater than or equal to 2, then the radicals $R_1$ may be identical or different,
$R_1$ represents a halogen atom: a saturated or unsaturated, aliphatic or alicylic, $C_1$–$C_6$ hydrocarbon chain, it being possible for the chain to contain one or more oxygen, nitrogen, silicon or sulphur atoms or an $SO_2$ group, and it being possible for the chain to be substituted with one or more hydroxyl or amino radicals; an onium radical Z, the radical $R_1$ not containing a peroxide bond, or diazo, nitro or nitroso radicals,
$R_2$ represents an onium radical Z or a radical —X—C=$NR_8$—$NR_9R_{10}$ in which X represents an oxygen atom or a radical —$NR_{11}$ and $R_8$, R9, $R_{10}$ and $R_{11}$ represent a hydrogen atom, a $C_1$–$C_4$ alkyl radical or a $C_1$–$C_4$ hydroxyalkyl radical,
$R_3$ represents a hydrogen atom or a hydroxyl radical.
4. The composition of claim 3, wherein the dye is selected from the group consisting of:
1,3-dimethyl-2-[4-(pyrrolidin-1-yl)phenylazo]benzimidazol-1-ium,
1,3-dimethyl-2-[4-(3-hydroxypyrrolidin-1-yl)phenylazo]benzimidazol-1-ium,
1,3-dimethyl-2-[4-(2-carboxypyrrolidin-1-yl)phenylazo]benzimidazol-1-ium,
1,3-dimethyl-2-[4-(3-aminopyrrolidin-1-yl)phenylazo]benzimidazol-1-ium,
1,3-dimethyl-2-[4-(2-carboxy-3-hydroxypyrrolidin-1-yl)phenylazo]benzimidazol-1-ium,
1,3-dimethyl-2-[4-(2-carboxamidopyrrolidin-1-yl)phenylazo]benzimidazol-1-ium,
1,3-dimethyl-2-[4-(2-hydroxymethylpyrrolidin-1-yl)phenylazo]benzimidazol-1-ium,
1,3-dimethyl-2-[4-(2-carboxy-4-hydroxypyrrolidin-1-yl)phenylazo]benzimidazol-1-ium,
1,3-dimethyl-2-[4-(piperidin-1-yl)phenylazo]benzimidazol-1-ium,
1,3-dimethyl-2-[4-(3-hydroxypiperidin-1-yl)phenylazo]benzimidazol-1-ium,
1,3-dimethyl-2-[4-(3-hydroxymethylpiperidin-1-yl)phenylazo]benzimidazol-1-ium, 1,3-dimethyl-2-[4-(3-carboxypiperidin-1-yl)phenylazo]
benzimidazol-1-ium,
1,3-dimethyl-2-[4-(2-carboxypiperidin-1-yl)phenylazo]
benzimidazol-1-ium,
1,3-dimethyl-2-[4-(piperazin-1-yl)phenylazo]benzimidazol-1-ium,
1,3-dimethyl-2-[4-(homopiperazin-1-yl)phenylazo]benzimidazol-1-ium,
5-amino-1,3-dimethyl-2-[4-(pyrrolidin-1-yl)phenylazo]
benzimidazol-1-ium,
5-amino-1,3-dimethyl-2-[4-(3-hydroxypyrrolidin-1-yl)
phenylazo]benzimidazol-1-ium,
5-amino-1,3-dimethyl-2-[4-(2-carboxypyrrolidin-1-yl)
phenylazo]benzimidazol-1-ium,
5-amino-1,3-dimethyl-2-[4-(3-aminopyrrolidin-1-yl)phenylazo]benzimidazol-1-ium,
5-amino-1,3-dimethyl-2-[4-(2-carboxy-3-hydroxypyrrolidin-1-yl)phenylazo]benzimidazol-1-ium,
5-amino-1,3-dimethyl-2-[4-(2-carboxamidopyrrolidin-1-yl)phenylazo]benzimidazol-1-ium,
5-amino-1,3-dimethyl-2-[4-(2-hydroxymethylpyrrolidin-1-yl)phenylazo]benzimidazol-1-ium,
5-amino-1,3-dimethyl-2-[4-(2-carboxy-4-hydroxypyrrolidin-1-yl)phenylazo]benzimidazol-1-ium,
5-amino-1,3-dimethyl-2-[4-(piperidin-1-yl)phenylazo]
benzimidazol-1-ium,
5-amino-1,3-dimethyl-2-[4-(3-hydroxypiperidin-1-yl)
phenylazo]benzimidazol-1-ium,
5-amino-1,3-dimethyl-2-[4-(3-hydroxymethylpiperidin-1-yl)phenylazo]benzimidazol-1-ium,
5-amino-1,3-dimethyl-2-[4-(3-carboxypiperidin-1-yl)
phenylazo]benzimidazol-1-ium,
5-amino-1,3-dimethyl-2-[4-(2-carboxypiperidin-1-yl)
phenylazo]benzimidazol-1-ium,
5-amino-1,3-dimethyl-2-[4-(piperazin-1-yl)phenylazo]
benzimidazol-1-ium,
5-amino-1,3-dimethyl-2-[4-(homopiperazin-1-yl)phenylazo]benzimidazol-1-ium,
5-dimethylamino-1,3-dimethyl-2-[4-(pyrrolidin-1-yl)-phenylazo]benzimidazol-1-ium,
5-dimethylamino-1,3-dimethyl-2-[4-(3-hydroxypyrrolidin-1-yl)phenylazo]benzimidazol-1-ium,
5-dimethylamino-1,3-dimethyl-2-[4-(2-carboxypyrrolidin-1-yl)phenylazo]benzimidazol-1-ium,
5-dimethylamino-1,3-dimethyl-2-[4-(3-aminopyrrolidin-1-yl)phenylazo]benzimidazol-1-ium,
5-dimethylamino-1,3-dimethyl-2-[4-(2-carboxy-3-hydroxypyrrolidin-1-yl)phenylazo]benzimidazol-1-ium,
5-dimethylamino-1,3-dimethyl-2-[4-(2-carboxamidopyrrolidin-1-yl)phenylazo]benzimidazol-1-ium,
5-dimethylamino-1,3-dimethyl-2-[4-(2-hydroxymethylpyrrolidin-1-yl)phenylazo]benzimidazol-1-ium,
5-dimethylamino-1,3-dimethyl-2-[4-(2-carboxy-4-hydroxypyrrolidin-1-yl)phenylazo]benzimidazol-1-ium,
5-dimethylamino-1,3-dimethyl-2-[4-(piperidin-1-yl)phenylazo]benzimidazol-1-ium,
5-dimethylamino-1,3-dimethyl-2-[4-(3-hydroxypiperidin-1-yl)phenylazo]benzimidazol-1-ium,
5-dimethylamino-1,3-dimethyl-2-[4-(3-hydroxymethylpiperidin-1-yl)phenylazo]benzimidazol-1-ium,
5-dimethylamino-1,3-dimethyl-2-[4-(3-carboxypiperidin-1-yl)phenylazo]benzimidazol-1-ium,
5-dimethylamino-1,3-dimethyl-2-[4-(2-carboxypiperidin-1-yl)phenylazo]benzimidazol-1-ium,
5-dimethylamino-1,3-dimethyl-2-[4-(piperazin-1-yl)phenylazo]benzimidazol-1-ium,
5-dimethylamino-1,3-dimethyl-2-[4-(homopiperazin-1-yl)phenylazo]benzimidazol-1-ium.

5. The composition of claim 1, wherein the cationic tertiary para-phenylenediamine is such that n is equal to 0.

6. The composition of claim 1, wherein the cationic tertiary para-phenylenediamine is such that n is equal to 1 and $R_1$ is chosen from the group consisting of a halogen atom; a saturated or unsaturated, aliphatic or alicyclic, $C_1$–$C_6$ hydrocarbon chain; it being possible for one or more carbon atoms to be replaced by an oxygen, nitrogen, silicon or sulphur atom, or by an $SO_2$ group, the radical $R_1$ not containing a peroxide bond, or diazo, nitro or nitroso radicals.

7. The composition of claim 1, wherein the cationic tertiary para-phenylenediamine is such that $R_1$ is chosen from chlorine, bromine, $C_1$–$C_4$ alkyl, $C_1$–$C_4$ hydroxyalkyl, $C_1$–$C_4$ aminoalkyl, $C_1$–$C_4$ alkoxy or $C_1$–$C_4$ hydroxyalkoxy radicals.

8. The composition of claim 7, wherein the cationic tertiary para-phenylenediamine is such that $R_1$ is chosen from a methyl, hydroxymethyl, 2-hydroxyethyl, 1,2-dihydroxyethyl, methoxy, isopropyloxy or 2-hydroxyethoxy radical.

9. The composition of claim 1, wherein the cationic tertiary para-phenylenediamine is such that $R_2$ represents the onium radical Z corresponding to formula (II)

$$-D\left[\begin{array}{c}(R_7)_x\ R4\\ \diagdown\ /\\ N^+-R5\\ /\ \diagdown\\ Y\ \ \ R6\end{array}\right] \quad (II)$$

in which

D is a single bond of a linear or branched $C_1$–$C_{14}$ alkylene chain which may contain one or more heteroatoms chosen from oxygen, sulphur or nitrogen, and which may be substituted with one or more hydroxyl, $C_1$–$C_6$ alkoxy or amino radicals and which may carry one or more ketone functional groups;

$R_4$, $R_5$ and $R_6$, taken separately, represent a $C_1$–$C_{15}$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$) alkyl radical; an aryl radical; a benzyl radical; a $C_1$–$C_6$ amidoalkyl radical; a tri($C_1$–$C_6$)alkylsilane($C_1$–$C_6$) alkyl radical; a $C_1$–$C_6$ aminoalkyl radical; a $C_1$–$C_6$ aminoalkyl radical in which the amine is mono- or di-substituted with a $C_1$–$C_4$ alkyl, ($C_1$–$C_6$)alkylcarbonyl, amido or ($C_1$–$C_6$)alkylsulphonyl radical; or $R_4$, $R_5$ and $R_6$ together, in pairs, form, with the nitrogen atom to which they are attached, a 4-, 5-, 6- or 7-membered saturated carbon ring which may contain one or more heteroatoms, it being possible for the cationic ring to be substituted with a halogen atom, a hydroxyl radical, a $C_1$–$C_6$ alkyl radical, a $C_1$–$C_6$ monohydroxyalkyl radical, a $C_2$–$C_6$ polyhydroxy-alkyl radical, a $C_1$–$C_6$ alkoxy radical, a tri($C_1$–$C_6$)alkylsilane ($C_1$–$C_6$)alkyl radical, an amido radical, a carboxyl radical, a ($C_1$–$C_6$)alkylcarbonyl radical, a thio (—SH) radical, a $C_1$–$C_6$ thioalkyl (—R—SH) radical, a ($C_1$–$C_6$)alkylthio radical, an amino radical, an amino radical which is mono- or di-substituted with a ($C_1$–$C_6$) alkyl, ($C_1$–$C_6$)alkylcarbonyl, amido or $C_1$–$C_6$)alkylsulphonyl radical;

$R_7$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical; a $C_1$–$C_6$ aminoalkyl radical whose amine is mono- or di-substituted with a ($C_1$–$C_6$)alkyl, ($C_1$–$C_6$)alkylcarbonyl, amido or ($C_1$–$C_6$)alkylsulphonyl radical; a $C_1$–$C_6$ carboxyalkyl radical; a $C_1$–$C_6$ carbamylalkyl radical; a $C_1$–$C_6$ trifluroalkyl radical; a tri($C_1$–$C_6$)alkylsilane($C_1$–$C_6$)alkyl radical; a $C_1$–$C_6$ suiphonamidoalkyl radical; a ($C_1$–$C_6$)alkylcarboxy($C_1$–$C_6$)alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; a $C_1$–$C_6$ alkylcarbonyl($C_1$–$C_6$)alkyl radical; an N—($C_1$–$C_6$)alkylcarbonyl($C_1$–$C_6$)alkyl radical; an N—($C_1$–$C_6$)alkylsulphonamido($C_1$–$C_6$)alkyl radical;

x is 0 or 1, when x=0, then the linking arm is attached to the nitrogen atom carrying the radicals $R_4$ to $R_6$;

when x=1, then two of the radicals $R_4$ to $R_6$ form, together with the nitrogen atom to which they are attached, a 4-, 5-, 6- or 7-membered saturated ring and D is linked to the carbon atom of the saturated ring;

Y is a counter-ion.

10. The composition of claim 9, wherein the cationic tertiary para-phenylenediamine is such that $R_2$ corresponds to formula II in which x is equal to 0 and $R_4$, $R_5$ and $R_6$ separately are preferably chosen from a $C_1$–$C_6$ alkyl radical, a $C_1$–$C_4$ monohydroxyalkyl radical, a $C_2$–$C_4$ polyhydroxyalkyl radical, a ($C_1$–$C_6$)alkoxy($C_1$–$C_4$)alkyl radical, a $C_1$–$C_6$ amidoalkyl radical, a tri($C_1$–$C_6$)alkylsilane($C_1$–$C_6$)alkyl radical, or $R_4$ with $R_5$ form together an azetidine ring, a pyrrolidine, piperidine, piperazine or morpholine ring, $R_6$ being chosen in this case from a $C_1$–$C_6$ alkyl radical; a $C_1$–$C_6$ monohydroxyalkyl radical, a $C_2$–$C_6$ polyhydroxyalkyl radical; a $C_1$–$C_6$ aminoalkyl radical, an aminoalkyl radical which is mono- or di-substituted with a ($C_1$–$C_6$)alkyl radical, a ($C_1$–$C_6$)alkylcarbonyl, amido or ($C_1$–$C_6$)alkylsulphonyl radical; a $C_1$–$C_6$ carbamylalkyl radical; a tri($C_1$–$C_6$)alkylsilane($C_1$–$C_6$)alkyl radical; a ($C_1$–$C_6$)alkyl carboxy($C_1$–$C_6$)alkyl radical; a ($C_1$–$C_6$)alkylcarbonyl($C_1$–$C_6$)alkyl radical; an N—($C_1$–$C_6$)alkylcarbamyl($C_1$–$C_6$)alkyl radical.

11. The composition of claim 9, wherein the cationic tertiary para-phenylenediamine is such that $R_2$ corresponds to formula II in which x is equal to 1 and $R_7$ is chosen from a $C_1$–$C_6$ alkyl radical; a $C_1$–$C_6$ monohydroxyalkyl radical; a $C_2$–$C_6$ polyhydroxy-alkyl radical; a $C_1$–$C_6$ aminoalkyl radical, a $C_1$–$C_6$ aminoalkyl radical whose amine is mono- or di-substited with a ($C_1$–$C_6$)alkyl, ($C_1$–$C_6$)alkylcarbonyl, amido or a ($C_1$–$C_6$)alkylsulphonyl radical; a $C_1$–$C_6$ carbamylalkyl radical, a tri($C_1$–$C_6$)alkylsilane($C_1$–$C_6$)alkyl radical; a ($C_1$–$C_6$)alkylcarboxy($C_1$–$C_6$)alkyl radical; a ($C_1$–$C_6$)alkylcarbonyl($C_1$–$C_6$)alkyl radical; an N—($C_1$–$C_6$)alkylcarbamyl($C_1$–$C_6$)alkyl radical; $R_4$ with $R_5$ together form an azetidine, pyrrolidine, piperidine, piperazine or morpholine ring, $R_6$ being chosen in this case from a $C_1$–$C_6$ alkyl radical; a $C_1$–$C_6$ monohydroxyalkyl radical; a $C_2$–$C_6$ polyhydroxyl alkyl radical; a $C_1$–$C_6$ aminoalkyl radical; a $C_1$–$C_6$ aminoalkyl radical whose amine is mono- or di-substituted with a ($C_1$–$C_6$)alkyl, ($C_1$–$C_6$)alkylcarbonyl, amido or ($C_1$–$C_6$)alkylsulphonyl radical; a $C_1$–$C_6$ carbamylalkyl radical; a tri($C_1$–$C_6$)alkylsilane($C_1$–$C_6$)alkyl radical; a ($C_1$–$C_6$)alkylcarboxy($C_1$–$C_6$)alkyl radical; a ($C_1$–$C_6$)alkylcarbonyl($C_1$–$C_6$)alkyl radical; an N—($C_1$–$C_6$)alkylcarbamyl($C_1$–$C_6$)alkyl radical.

12. The composition of claim 9, wherein the cationic tertiary para-phenylenediamine is such that D is a single bond or an alkylene chain which may be substituted.

13. The composition of claim 9, wherein the cationic tertiary para-phenylenediamine is such that $R_2$ is a trialkylammonium radical.

14. The composition of claim 1, wherein the cationic tertiary para-phenylenediamine is such that $R_2$ represents the onium radical Z corresponding to formula III

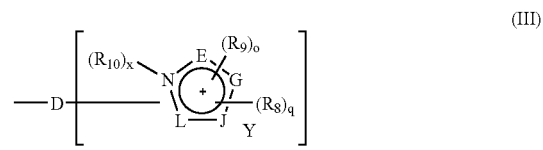

in which

D is a single bond or a linear or branched $C_1$–$C_{14}$ alkylene chain which may contain one or more heteroatoms chosen from oxygen, sulphur or nitrogen, and which may be substituted with one or more hydroxyl, $C_1$–$C_6$ alkoxy or amino radicals, and which may carry one or more ketone functional groups;

the vertices E, G, J, L, which are identical or different, represent a carbon, oxygen, sulphur or nitrogen atom to form a pyrrole, pyrazole, imidazole, triazole, oxazole, isooxazole, thiazole, isothiazole ring, q is an integer between 0 and 4 inclusive;

is an integer between 0 and 3 inclusive;

q+o is an integer between 0 and 4;

the radicals $R_8$, which are identical or different, represent a halogen atom, a hydroxyl radical, a $C_1$–$C_6$ alkyl radical, a $C_1$–$C_6$ monohydroxyalkyl radical, a $C_1$–$C_6$ polyhydroxyalkyl radical, a $C_1$–$C_6$ alkoxy radical, a tri($C_1$–$C_6$)alkylsilane($C_1$–$C_6$)alkyl radical, an amido radical, a carboxyl radical, a $C_1$–$C_6$ alkylcarbonyl radical, a thio radical, a $C_1$–$C_6$ thioalkyl radical, a ($C_1$–$C_6$) alkylthio radical, an amino radical, an amino radical which is mono- or di-substituted with a ($C_1$–$C_6$)alkyl, ($C_1$–$C_6$)alkylcarbonyl, amido or ($C_1$–$C_6$)alkylsulphonyl radical; a $C_1$–$C_6$ monohydroxyalkyl radical or a $C_2$–$C_6$ polyhydroxyalkyl radical; it being understood that the radicals $R_8$ are carried by a carbon atom, the radicals $R_9$, which are identical or different, represent a $C_1$–$C_6$ alkyl radical, a $C_1$–$C_6$ monohydroxyalkyl radical, a $C_2$–$C_6$ polyhydroxyalkyl radical, a tri($C_1$–$C_6$)alkylsilane($C_1$–$C_6$)alkyl radical, a ($C_1$–$C_6$)alkoxy($C_1$–$C_6$)alkyl radical, a $C_1$–$C_6$ carbamylalkyl radical, a ($C_1$–$C_6$)alkylcarboxy($C_1$–$C_6$)alkyl radical, a benzyl radical; it being understood that the radicals $R_9$ are carried by a nitrogen, $R_{10}$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical whose amine is substituted with a ($C_1$–$C_6$)alkyl, ($C_1$–$C_6$)alkylcarbonyl, amido or ($C_1$–$C_6$)alkylsulphonyl radical; a $C_1$–$C_6$ carboxyalkyl radical; a $C_1$–$C_6$ carbamylalkyl radical; a $C_1$–$C_6$ trifluoroalkyl radical; a tri($C_1$–$C_6$)alkylsilane($C_1$–$C_6$)alkyl radical; a $C_1$–$C_6$ sulphonamidoalkyl radical; a ($C_1$–$C_6$)alkylcarboxy($C_1$–$C_6$)alkyl radical; a ($C_1$–$C_6$)alkylsulphonyl($C_1$–$C_6$)alkyl radical; a ($C_1$–$C_6$)alkylsulphonyl($C_1$–$C_6$)alkyl radical; a ($C^1$–$C_6$)alkylcarbonyl($C_1$–$C_6$)alkyl radical; an N—($C_1$–$C_6$)alkylcarbamyl($C_1$–$C_6$)alkyl radical; an N—($C_1$–$C_6$)alkylsulphonamido($C_1$–$C_6$)alkyl radical;

x is 0 or 1 when x=0, the linking arm D is attached to the nitrogen atom, when x=1, the linking arm D is attached to one of the vertices E, G, J or L, Y is a counter-ion.

15. The composition of claim 14, wherein the cationic tertiary para-phenylenediamine is such that the vertices E, G, J and L form an imidazole ring.

16. The composition of claim 14, wherein the cationic tertiary para-phenylenediamine is such that x is equal to 0, D is a single bond or an alkylene chain which may be substituted.

17. The composition of claim 1, wherein the cationic tertiary para-phenylenediamine is such that $R_2$ represents an onium radical Z corresponding to formula IV

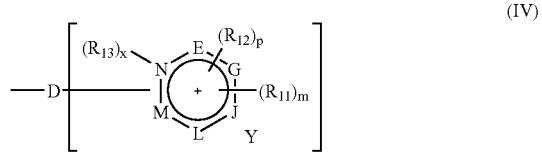

(IV)

in which:

D is a single bond or a linear or branched $C_1$–$C_{14}$ alkylene chain which may contain one or more heteroatoms chosen from an oxygen, sulphur or nitrogen atom, and which may be substituted with one or more hydroxyl, $C_1$–$C_6$ alkoxy or amino radicals, and which may carry one or more ketone functional groups;

the vertices E, G, J, L and M, which are identical or different, represent a carbon, oxygen, sulphur or nitrogen atom to form a ring chosen from the pyridine, pyrimidine, pyrazine, triazine and pyridazine rings;

p is an integer between 0 and 3 inclusive;

m is an integer between 0 and 5 inclusive;

p+m is an integer between 0 and 5;

the radicals $R_{11}$, which are identical or different, represent a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical, a tri($C_1$–$C_6$)alkylsilane($C_1$–$C_6$)alkyl radical, an amido radical, a carboxyl radical, a $C_1$–$C_6$ alkylcarbonyl radical, a thio radical, a $C_1$–$C_6$ thioalkyl radical, a ($C_1$–$C_6$)alkylthio radical, an amino radical, an amino radical which is substituted with a ($C_1$–$C_6$)alkyl, ($C_1$–$C_6$)alkylcarbonyl, amido or ($C_1$–$C_6$)alkylsulphonyl radical; a $C_1$–$C_6$ monohydroxyalkyl radical or a $C_2$–$C_6$ polyhydroxyalkyl radical; it being understood that the radicals $R_{11}$ are carried by a carbon atom, the radicals $R_{12}$, which are identical or different, represent a $C_1$–$C_6$ alkyl radical, a $C_1$–$C_6$ monohydroxyalkyl radical, a $C_2$–$C_6$ polyhydroxyalkyl radical, a tri($C_1$–$C_6$)alkylsilane($C_1$–$C_6$)alkyl radical, a ($C_1$–$C_6$)alkoxy($C_1$–$C_6$)alkyl radical, a $C_1$–$C_6$ carbamylalkyl radical, a ($C_1$–$C_6$)alkylcarboxy($C_1$–$C_6$)alkyl radical, a benzyl radical; it being understood that the radicals $R_{12}$ are carried by a nitrogen, $R_{13}$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical whose amine is mono- or di-substituted with a ($C_1$–$C_6$)alkyl, ($C_1$–$C_6$)alkylcarbonyl, amido or ($C_1$–$C_6$)alkylsulphonyl radical; a $C_1$–$C_6$ carboxyalkyl radical; a $C_1$–$C_6$ carbamylalkyl radical; a $C_1$–$C_6$ trifluoroalkyl radical; a tri($C_1$–$C_6$)alkylsilane($C_1$–$C_6$)alkyl radical; a $C_1$–$C_6$ sulphonamidoalkyl radical; a ($C_1$–$C_6$)alkylcarboxy($C_1$–$C_6$)alkyl radical; a ($C_1$–$C_6$)alkylsulphonyl($C_1$–$C_6$)alkyl radical; a ($C_1$–$C_6$)alkylsulphonyl($C_1$–$C_6$)alkyl radical; a ($C_1$–$C_6$)alkylcarbonyl($C_1$–$C_6$)alkyl radical; an N—($C_1$–$C_6$)alkylcarbamyl($C_1$–$C_6$)alkyl radical; an N—($C_1$–$C_6$)alkylsulphonamido($C_1$–$C_6$)alkyl radical;

x is 0 or 1 when x=0, the linking arm D is attached to the nitrogen atom, when x=1, the linking arm D is attached to one of the vertices E, G, J, L or M, Y is a counter-ion.

18. The composition of claim 17, wherein the vertices E, G, J, L and M form, with the nitrogen of the ring, a ring chosen from pyridine and pyrimidine rings.

19. The composition of claim 17, wherein the cationic tertiary para-phenylenediamine is such that x is equal to 0 and $R_{11}$ is chosen from a hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical, a tri($C_1$–$C_6$)alkylsilane($C_1$–$C_6$)alkyl radical, an amido radical, a $C_1$–$C_6$ alkylcarbonyl radical, an amino radical, an amino radical which is mono- or di-substituted with a ($C_1$–$C_6$)alkyl, a ($C_1$–$C_6$)alkylcarbonyl, amido or ($C_1$–$C_6$)alkylsulphonyl radical; a $C_1$–$C_6$ monohydroxyalkyl radical or a $C_2$–$C_6$ polyhydroxyalkyl radical and $R_{12}$ is chosen from a $C_1$–$C_6$ alkyl radical, a $C_1$–$C_6$ monohydroxyalkyl radical, a $C_2$–$C_6$ polyhydroxyalkyl radical, a tri($C_1$–$C_6$)alkylsilane($C_1$–$C_6$)alkyl radical, a ($C_1$–$C_6$)alkoxy($C_1$–$C_6$)alkyl radical, a $C_1$–$C_6$ carbamylalkyl radical.

20. The composition of claim 17, wherein the cationic tertiary para-phenylenediamine is such that x is equal to 1 and $R_{13}$ is chosen from a $C_1$–$C_6$ alkyl radical; a $C_1$–$C_6$ monohydroxyalkyl radical; a $C_2$–$C_6$ polyhydroxyalkyl radical; a $C_1$–$C_6$ aminoalkyl radical, a $C_1$–$C_6$ aminoalkyl radical whose amine is mono- or di-substituted with a ($C_1$–$C_6$)alkyl radical, a ($C_1$–$C_6$)alkylcarbonyl radical, an amido radical, a ($C_1$–$C_6$)alkylsulphonyl radical; a $C_1$–$C_6$ carbamylalkyl radical; a tri($C_1$–$C_6$)alkylsilane($C_1$–$C_6$)alkyl radical; a ($C_1$–$C_6$)alkylcarbonyl($C_1$–$C_6$)alkyl radical; an N—($C_1$–$C_6$)alkylcarbamyl($C_1$–$C_6$)alkyl radical; $R_{11}$ is chosen from a hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical, a tri($C_1$–$C_6$)alkylsilane($C_1$–$C_6$)alkyl radical, an amido radical, a $C_1$–$C_6$ alkylcarbonyl radical, an amino radical, an amino radical which is mono- or di- substituted with a ($C_1$–$C_6$)alkyl, ($C_1$–$C_6$)alkylcarbonyl, amido or ($C_1$–$C_6$)alkylsulphonyl radical; and $R_{12}$ is chosen from a $C_1$–$C_6$ alkyl radical, a $C_1$–$C_6$ monohydroxyalkyl radical, a $C_2$–$C_6$ polyhydroxyalkyl radical, a tri($C_1$–$C_6$)alkylsilane ($C_1$–$C_6$)alkyl radical, a ($C_1$–$C_6$)alkoxy($C_1$–$C_6$)alkyl radical, a $C_1$–$C_6$ carbamylalkyl radical.

21. The composition of claim 17, wherein the cationic tertiary para-phenylenediamine is such that $R_{11}$, $R_{12}$ and $R_{13}$ are alkyl radicals which may be substituted.

22. The composition of claim 1, wherein the cationic tertiary para-phenylenediamine is such that the radical $R_2$ is the radical of formula —XP(O)(O—) OCH$_2$CH$_2$N$^+$(CH$_3$)$_3$ where X represents an oxygen atom or a radical —NR$_{14}$, $R_{14}$ representing a hydrogen, a $C_1$–$C_4$ alkyl radical or a hydroxyalkyl radical.

23. The composition of claim 1, wherein the cationic tertiary para-phenylenediamine is such that the radical $R_2$ is a guanidine radical of formula —X—C=$NR_8$—$NR_9R_{10}$, X represents an oxygen atom or a radical —$NR_{11}$, $R_8$, $R_9$, $R_{10}$ and $R_{11}$ representing a hydrogen, a $C_1$–$C_4$ alkyl radical or a hydroxyalkyl radical.

24. The composition of claim 1, wherein the cationic tertiary para-phenylene is chosen from the group consisting of:

[1-(4-Aminophenyl)pyrrolidin-3-yl]trimethylammonium chloride,

[1-(4-Aminophenyl)pyrrolidin-3-yl]dimethyltetradecylammonium bromide

N'-[1-(4-Aminophenyl)pyrrolidin-3-yl]-N,N-dimethylguanidinium chloride

N-[1-(4-Aminophenyl)pyrrolidin-3-yl]guanidinium chloride

3-[1-(4-Aminophenyl)pyrrolidin-3-yl]-1-methyl-3H-imidazol-1-ium chloride

[1-(4-Aminophenyl)pyrrolidin-3-yl]-(2-hydroxyethyl) dimethylammonium chloride

[1-(4-Aminophenyl)pyrrolidin-3-yl]dimethyl-(3-trimethylsilanylpropyl)ammonium chloride

[1-(4-Aminophenyl)pyrrolidin-3-yl]-(trimethylammonium-hexyl)dimethylammonium dichloride

[1-(4-Aminophenyl)pyrrolidin-3-yl]oxophosphoryleholine

{2-[1-(4-Aminophenyl)pyrrolidin-3-yloxy]ethyl}trimethylanmonium chloride

1-{2-[1-(4-Aminophenyl)pyrrolidin-3-yloxy]ethyl}-1-methylpyrrolidinium chloride

3-{3-[1-(4-Aminophenyl)pyrrolidin-3-yloxy]propyl}-1-methyl-3H-imidazol-1-ium chloride 1-{2-[1-(4-Aminophenyl)pyrrolidin-3-yloxy]ethyl}-1-methylpiperidinium chloride 3-{3-[1-(5-trimethylsilanylethyl-4-Amino-3-trimethylsilanylethylphenyl)pyrrolidin-3-yloxy]propyl}-1-methyl-3H-imidazol-1-um chloride

[1-(4-Amino-3-methylphenyl)pyrrolidin-3-yl]trimethylammonium chloride

[1-(4-Amino-3-methylphenyl)pyrrolidin-3-yl]dimethyltetradecylammonium chloride

N'-[1-(4-Amino-3-methylphenyl)pyrrolidin-3-yl]-N,N-dimethylguanidinium chloride

N-[1-(4-Amino-3-methylphenyl)pyrrolidin-3-yl]guanidinium chloride

3-[1-(4-Amino-3-methylphenyl)pyrrolidin-3-yl]-1-methyl-3H-imidazol-1-ium chloride

[1-(4-Amino-3-methylphenyl)pyrrolidin-3-yl]-(2-hydroxyethyl)dimethylammonium chloride

[1-(4-Amino-3-methylphenyl)pyrrolidin-3-yl]dimethyl-(3-trimethylsilanylpropyl chloride

[1-(4-Amino-3-methylphenyl)pyrrolidin-3-yl]-(trimethylammoniumhexyl-dimethylammonium dichloride

[1-(4-Amino-3-methylphenyl)pyrrolidin-3-yl]oxophosphorylcholine

{2-[1-(4-Amino-3-methylphenyl)pyrrolidin-3-yloxy]ethyl}trimethylammonium chloride 1-{2-[1-(4-Amino-3-methylphenyl)pyrrolidin-3-yloxy]ethyl}-1-methylpyrrolidinium chloride 3-{3-[1-(4-Amino-3-methylphenyl)pyrrolidin-3-yloxy]propyl}1-methyl-3H-imidazol-1-ium chloride 1-{2-[1-(4-Amino-3-methylphenyl)pyrrolidin-3-yloxy]ethyl}-1-methylpiperidinium chloride

[1-(4-Amino-3-trimethylsilanylethylphenyl)pyrrolidin-3-yl]trimethylammonium chloride 3-[1-(4-Amino-3-trimethylsilanylethylphenyl)pyrrolidin-3-yl]-1-methyl-3H-imidazol-1-ium chloride 3-{3-[1-(4-Amino-3-trimethylsilanylethylphenyl)pyrrolidin-3-yloxy]propyl}-1-methyl-3H-imidazol-1-urn chloride

[1-(5-trimethylsilanylethyl-4-Amino-3-trimethylsilanylethylphenyl)pyrrolidin-3-yl]trimethylammonium chloride 3-[1-(5-trimethylsilanylethyl-4-Amino-3-trimethylsilanylethylphenyl)pyrrolidin-3-yl]-1-methyl-3H-imidazol-1-ium chloride 1'-(4-Aminophenyl)-1-methyl-1,3'bipyrrolidinyl-1-ium chloride 1'-(4-Amino-3-methylphenyl)-1-methyl-1,3'bipyrrolidinyl-1-ium chloride 3-{[1-(4-Aminophenyl)pyrrolidin-3-ylcarbamoyl]methyl}-1-methyl-3H-imidazol-1-ium chloride 3-{[1-(4-Amino-3-methylphenyl)pyrrolidin-3-ylcarbamoyl]methyl}-1-methyl-3H-imidazol-1-ium chloride 3-[1-(4-Aminophenyl)pyrrolidin-3-yl]-1-(3-trimethylsilanylpropyl)-3H-imidazol-1-ium chloride 3-[1-(4-Aminophenyl)pyrrolidin-3-yl]-1-(3-trimethylsilanylpropyl)-3H-imidazol-1-ium chloride

[1-(4-aminophenyl)pyrrolidin-3-yl]ethyldimethylammonium chloride

[1-(4-aminophenyl)pyrrolidin-3-yl]ethyldimethylammonium iodide

[1-(4-aminophenyl)pyrrolidin-3-yl]propyldimethylammonium iodide,

[1-(4-aminophenyl)pyrrolidin-3-yl]propyldimethylammonium bromide

[1-(4-aminophenyl)pyrrolidin-3-yl]propyldimethylammonium methosulphate

[1-(4-aminophenyl)pyrrolidin-3-yl]butyldimethylammonium iodide

[1-(4-aminophenyl)pyrrolidin-3-yl]pentyldimethylammonium iodide

[1-(4-aminophenyl)pyrrolidin-3-yl]hexyldimethylanimonium iodide

[1-(4-aminophenyl)pyrrolidin-3-yl]heptyldimethylammonium iodide

[1-(4-Aminophenyl)pyrrolidin-3-yl]octyldimethylammonium iodide

[1-(4-aminophenyl)pyrrolidin-3-yl]decyldimethylammonium iodide

[1-(4-aminophenyl)pyrrolidin-3-yl]hexadecyldimethylammonium iodide

[1-(4-aminophenyl)pyrrolidin-3-yl]hydroxyethyldimethylammonium chloride

[1-(4-aminophenyl)pyrrolidin-3-yl]hydroxyethyldimethylammonium iodide.

25. The composition of claim 1, wherein the cationic tertiary para-phenylene is chosen from the group consisting of:

[1-(4-Aminophenyl)pyrrolidin-3-yl]trimethylanimonium chloride

[1-(4-Aminophenyl)pyrrolidin-3-yl]dimethyltetradecylammonium bromide

N'-[1-(4-Aminophenyl)pyrrolidin-3-yl]-N,N-dimethylguanidinium chloride

N-[1-(4-Aminophenyl)pyrrolidin-3-yl]guanidinium chloride

3-[1-(4-Aminophenyl)pyrrolidin-3-yl]-1-methyl-3H-imidazol-1-ium chloride

[1-(4-Aminophenyl)pyrrolidin-3-yl]-(2-hydroxyethyl) dimethylammonium chloride

[1-(4-Aminophenyl)pyrrolidin-3-yl]dimethyl-(3-trimethylsilanylpropyl)ammonium chloride
[1-(4-Amino-3-methylphenyl)pyrrolidin-3-yl]trimethylammonium chloride
[1-(4-Amino-3-methylphenyl)pyrrolidin-3-yl]dimethyltetradecylammonium chloride
N'-[1-(4-Amino-3-methylphenyl)pyrrolidin-3-yl]-N,N-dimethylguanidinium chloride
N-[1-(4-Amino-3-methylphenyl)pyrrolidin-3-yl]guanidinium chloride
3-[1-(4-Amino-3-methylphenyl)pyrrolidin-3-yl]-1-methyl-3H-imidazol-1-ium chloride
[1-(4-Amino-3-methylphenyl)pyrrolidin-3-yl]-(2-hydroxyethyl)dimethylammonium chloride
[1-(4-Amino-3-methylphenyl)pyrrolidin-3-yl]dimethyl-(3-trimethylsilanylpropylammonium chloride
1'-(4-Aminophenyl)-1-methyl-[1,3']bipyrrolidinyl-1-ium chloride
1'-(4-Amino-3-methylphenyl)-1-methyl-[1,3']bipyrrolidinyl-1-ium chloride
3-{[1-(4-Aminophenyl)pyrrolidin-3-ylcarbamoyl]methyl}-1-methyl-3H-imidazol-1-ium chloride
3-{[1-(4-Amino-3-methylphenyl)pyrrolidin-3-ylcarbamoyl]methyl}-1-methyl-3H-imidazol-1-ium chloride
3-[1-(4-Aminophenyl)pyrrolidin-3-yl]-1-(3-trimethylsilanylpropyl)-3H-imidazol-1-ium chloride
3-[1-(4-Amino-3-methylphenyl)pyrrolidin-3-yl]-1-(3-trimethylsilanyl-propyl)-3H-imidazol-1-ium chloride
[1-(4-aminophenyl)pyrrolidin-3-yl]ethyldimethylammonium chloride
[1-(4-aminophenyl)pyrrolidin-3-yl]ethyldimethylammonium iodide
[1-(4-Aminophenyl)pyrrolidin-3-yl]propyldimethylammonium iodide
[1-(4-aminophenyl)pyrrolidin-3-yl]propyldimethylammonium bromide
[1-(4-aminophenyl)pyrrolidin-3-yl]propyldimethylammonium methosulphate
[1-(4-aminophenyl)pyrrolidin-3-yl]butyldimethylammonium iodide
[1-(4-aminophenyl)pyrrolidin-3-yl]pentyldimethylammonium iodide
[1-(4-aminophenyl)pyrrolidin-3-yl]hexyldimethylammonium iodide
[1-(4-aminophenyl)pyrrolidin-3-yl]heptyldimethylammonium iodide
[1-(4-aminophenyl)pyrrolidin-3-yl]octyldimethylammonium iodide
[1-(4-aminophenyl)pyrrolidin-3-yl]decyldimethylammonium iodide
[1-(4-aminophenyl)pyrrolidin-3-yl]hexadecyldimethylammonium iodide
[1-(4-aminophenyl)pyrrolidin-3-yl]hydroxyethyldimethylammonium chloride
[1-(4-aminophenyl)pyrrolidin-3-yl]hydroxyethyldimethylammonium iodide.

26. The composition of claim 1, wherein the cationic tertiary para-phenylene is chosen from the group consisting of:
[1-(4-Aminophenyl)pyrrolidin-3-yl]trimethylammonium chloride
[1-(4-Aminophenyl)pyrrolidin-3-yl]dimethyltetradecylammonium bromide
N'-[1-(4-Aminophenyl)pyrrolidin-3-yl]-N,N-dimethylguanidinium chloride
N-[1-(4-Aminophenyl)pyrrolidin-3-yl]guanidinium chloride
3-[1-(4-Aminophenyl)pyrrolidin-3-yl]-1-methyl-3H-imidazol-1-ium chloride
[1-(4-Aminophenyl)pyrrolidin-3-yl]-(2-hydroxyethyl)dimethylammonium chloride
[1-(4-Aminophenyl)pyrrolidin-3-yl]dimethyl-(3-trimethylsilanylpropyl)ammonium chloride
[1-(4-Aminophenyl)pyrrolidin-3-yl]-(trimethylammoniumhexyl)dimethylammonium dichloride
1'-(4-Aminophenyl)-1-methyl-[1,3']bipyrrolidinyl-1-ium chloride
3-[1-(4-Aminophenyl)pyrrolidin-3-yl]-1-(3-trimethylsilanylpropyl)-3H-imidazol-1-ium chloride
3-[-1-(4-Amino-3-methylphenyl)pyrrolidin-3-yl]-1-(3-trimethylsilanylpropyl)-3H-imidazol-1-ium chloride
[1-(4-aminophenyl)pyrrolidin-3-yl]ethyldimethylammonium chloride
[1-(4-aminophenyl)pyrrolidin-3-yl]ethyldimethylammonium iodide
[1-(4-aminophenyl)pyrrolidin-3-yl]propyldimethylammonium iodide
[1-(4-aminophenyl)pyrrolidin-3-yl]propyldimethylammonium bromide
[1-(4-aminophenyl)pyrrolidin-3-yl]propyldimethylammonium methosulphate
[1-(4-aminophenyl)pyrrolidin-3-yl]butyldimethylammonium iodide
[1-(4-aminophenyl)pyrrolidin-3-yl]pentyldimethylammonium iodide
[1-(4-aminophenyl)pyrrolidin-3-yl]hexyldimethylammonium iodide
[1-(4-aminophenyl)pyrrolidin-3-yl]heptyldimethylammonium iodide
[1-(4-aminophenyl)pyrrolidin-3-yl]octyldimethylammonium iodide
[1-(4-aminophenyl)pyrrolidin-3-yl]decyldimethylammonium iodide
[1-(4-aminophenyl)pyrrolidin-3-yl]hexadecyldimethylammonium iodide
[1-(4-aminophenyl)pyrrolidin-3-yl]hydroxyethyldimethylammonium chloride
[1-(4-aminophenyl)pyrrolidin-3-yl]hydroxyethyldimethylammonium iodide.

27. The composition of claim 1, wherein the cationic tertiary para-phenylene is chosen from the group consisting of:
[1-(4-Aminophenyl)pyrrolidin-3-yl]trimethylammonium chloride
3-[1-(4-Aminophenyl)pyrrolidin-3-yl]-1-methyl-3H-imidazol-1-ium chloride
[1-(4-Aminophenyl)pyrrolidin-3-yl]-(2-hydroxyethyl)dimethylammonium chloride
1'-(4-Aminophenyl)-1-methyl-[1,3']bipyrrolidinyl-1-ium chloride.

28. The composition of claim 1, wherein the cationic tertiary para-phenylene is chosen from the group consisting of:
[1-(4-Aminophenyl)pyrrolidin-3-yl]trimethylammonium chloride, and
[1-(4-Aminophenyl)pyrrolidin-3-yl]-(2-hydroxyethyl)dimethylammonium chloride.

29. The composition of claim 2, wherein the cationic tertiary para-phenylenediamine is such that n is equal to 0.

30. The composition of claim 2, wherein the cationic tertiary para-phenylenediamine is such that n is equal to 1 and $R_1$ is chosen from the group consisting of a halogen atom; a saturated or unsaturated, aliphatic or alicyclic, $C_1$–$C_6$ hydrocarbon chain; it being possible for one or more carbon atoms to be replaced by an oxygen, nitrogen, silicon or sulphur atom, or by an $SO_2$ group, the radical $R_1$ not containing a peroxide bond, or diazo, nitro or nitroso radicals.

31. The composition of claim 2, wherein the cationic tertiary para-phenylenediamine is such that $R_1$ is chosen from chlorine, bromine, $C_1$–$C_4$ alkyl, $C_1$–$C_4$ hydroxyalkyl, $C_1$–$C_4$ aminoalkyl, $C_1$–$C_4$ alkoxy or $C_1$–$C_4$ hydroxyalkoxy radicals.

32. The composition of claim 31, wherein the cationic tertiary para-phenylenediamine is such that $R_1$ is chosen from a methyl, hydroxymethyl, 2-hydroxyethyl, 1,2-dihydroxyethyl, methoxy, isopropyloxy or 2-hydroxyethoxy radical.

33. The composition of claim 2, wherein the cationic tertiary para-phenylenediamine is such that $R_2$ represents the onium radical Z corresponding to formula (II)

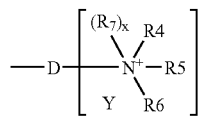

in which
- D is a single bond of a linear or branched $C_1$–$C_{14}$ alkylene chain which may contain one or more heteroatoms chosen from oxygen, sulphur or nitrogen, and which may be substituted with one or more hydroxyl, $C_1$–$C_6$ alkoxy or amino radicals and which may carry one or more ketone functional groups;
- $R_4$, $R_5$ and $R_6$, taken separately, represent a $C_1$–$C_{15}$ alkyl radical; a $C_1$–$C_6$ monohydroxyalkyl radical; a $C_2$–$C_6$ polyhydroxyalkyl radical; a $(C_1$–$C_6)$alkoxy$(C_1$–$C_6)$ alkyl radical; an aryl radical; a benzyl radical; a $C_1$–$C_6$ amidoalkyl radical; a tri$(C_1$–$C_6)$alkylsilane$(C_1$–$C_6)$ alkyl radical; a $C_1$–$C_6$ aminoalkyl radical; a $C_1$–$C_6$ aminoalkyl radical in which the amine is mono- or di-substituted with a $C_1$–$C_4$ alkyl, $(C_1$–$C_6)$alkylcarbonyl, amido or $(C_1$–$C_6)$alkylsulphonyl radical; or
- $R_4$, $R_5$ and $R_6$ together, in pairs, form, with the nitrogen atom to which they are attached, a 4-, 5-, 6- or 7-membered saturated carbon ring which may contain one or more heteroatoms, it being possible for the cationic ring to be substituted with a halogen atom, a hydroxyl radical, a $C_1$–$C_6$ alkyl radical, a $C_1$–$C_6$ monohydroxyalkyl radical, a $C_2$–$C_6$ polyhydroxy-alkyl radical, a $C_1$–$C_6$ alkoxy radical, a tri$(C_1$–$C_6)$alkylsilane $(C_1$–$C_6)$alkyl radical, an amido radical, a carboxyl radical, a $(C_1$–$C_6)$alkylcarbonyl radical, a thio (—SH) radical, a $C_1$–$C_6$ thioalkyl (—R—SH) radical, a $(C_1$–$C_6)$alkylthio radical, an amino radical, an amino radical which is mono- or di-substituted with a $(C_1$–$C_6)$ alkyl, $(C_1$–$C_6)$alkylcarbonyl, amido or $(C_1$–$C_6)$alkylsulphonyl radical;
- $R_7$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical; a $C_1$–$C_6$ aminoalkyl radical whose amine is mono- or di-substituted with a $(C_1$–$C_6)$alkyl, $(C_1$–$C_6)$ alkylcarbonyl, amido or $(C_1$–$C_6)$alkylsulphonyl radical; a $C_1$–$C_6$ carboxyalkyl radical; a $C_1$–$C_6$ carbamylalkyl radical; a $C_1$–$C_6$ trifluroalkyl radical; a tri $(C_1$–$C_6)$alkylsilane$(C_1$–$C_6)$alkyl radical; a $C_1$–$C_6$ sulphonamidoalkyl radical; a $(C_1$–$C_6)$alkylcarboxy $(C_1$–$C_6)$alkyl radical; a $(C_1$–$C_6)$alkylsulphinyl$(C_1$–$C_6)$ alkyl radical; a $(C_1$–$C_6)$alkylsulphonyl$(C_1$–$C_6)$alkyl radical; a $(C_1$–$C_6)$alkylcarbonyl$(C_1$–$C_6)$alkyl radical; an N—$(C_1$–$C_6)$alkylcarbamyl$(C_1$–$C_6)$alkyl radical; an N—$(C_1$–$C_6)$alkylsulphonamido$(C_1$–$C_6)$alkyl radical;
- x is 0 or 1,
    - when x=0, then the linking arm is attached to the nitrogen atom carrying the radicals $R_4$ to $R_6$;
    - when x=1, then two of the radicals $R_4$ to $R_6$ form, together with the nitrogen atom to which they are attached, a 4-, 5-, 6- or 7-membered saturated ring and D is linked to the carbon atom of the saturated ring;
- Y is a counter-ion.

34. The composition of claim 33, wherein the cationic tertiary para-phenylenediamine is such that $R_2$ corresponds to formula II in which x is equal to 0 and $R_4$, $R_5$ and $R_6$ separately are preferably chosen from a $C_1$–$C_6$ alkyl radical, a $C_1$–$C_4$ monohydroxyalkyl radical, a $C_2$–$C_4$ polyhydroxyalkyl radical, a $(C_1$–$C_6)$alkoxy$(C_1$–C4)alkyl radical, a $C_1$–$C_6$ amidoalkyl radical, a tri$(C_1$–$C_6)$alkylsilane$(C_1$–$C_6)$alkyl radical, or $R_4$ with $R_5$ form together an azetidine ring, a pyrrolidine, piperidine, piperazine or morpholine ring, $R_6$ being chosen in this case from a $C_1$–$C_6$ alkyl radical; a $C_1$–$C_6$ monohydroxyalkyl radical, a $C_2$–$C_6$ polyhydroxyalkyl radical; a $C_1$–$C_6$ aminoalkyl radical, an aminoalkyl radical which is mono- or di-substituted with a $(C_1$–$C_6)$alkyl radical, a $(C_1$–$C_6)$alkylcarbonyl, amido or $(C_1$–$C_6)$alkylsulphonyl radical; a $C_1$–$C_6$ carbamylalkyl radical; a tri$(C_1$–$C_6)$ alkylsilane$(C_1$–$C_6)$alkyl radical; a $(C_1$–$C_6)$alkyl carboxy $(C_1$–$C_6)$alkyl radical; a $(C_1$–$C_6)$alkylcarbonyl$(C_1$–$C_6)$alkyl radical; an $(C_1$–$C_6)$alkylcarbamyl$(C_1$–$C_6)$alkyl radical.

35. The composition of claim 33, wherein the cationic tertiary para-phenylenediamine is such that $R_2$ corresponds to formula II in which x is equal to 1 and $R_7$ is chosen from a $C_1$–$C_6$ alkyl radical; a $C_1$–$C_6$ monohydroxyalkyl radical; a $C_2$–$C_6$ polyhydroxy-alkyl radical; a $C_1$–$C_6$ aminoalkyl radical, a $C_1$–$C_6$ aminoalkyl radical whose amine is mono- or di-substited with a $(C_1$–$C_6)$alkyl, $(C_1$–$C_6)$alkylcarbonyl, amido or a $(C_1$–$C_6)$alkylsulphonyl radical; a $C_1$–$C_6$ carbamylalkyl radical, a tri$(C_1$–$C_6)$alkylsilane$(C_1$–$C_6)$alkyl radical; a $(C_1$–$C_6)$alkylcarboxy$(C_1$–$C_6)$alkyl radical; a $(C_1$–$C_6)$alkylcarbonyl$(C_1$–$C_6)$alkyl radical; an N—$(C_1$–$C_6)$ alkylcarbamyl$(C_1$–$C_6)$alkyl radical; $R_4$ with $R_5$ together form an azetidine, pyrrolidine, piperidine, piperazine or morpholine ring, $R_6$ being chosen in this case from a $C_1$–$C_6$ alkyl radical; a $C_1$–$C_6$ monohydroxyalkyl radical; a $C_2$–$C_6$ polyhydroxyl alkyl radical; a $C_1$–$C_6$ aminoalkyl radical; a $C_1$–$C_6$ aminoalkyl radical whose amine is mono- or di-substituted with a $(C_1$–$C_6)$alkyl, $(C_1$–$C_6)$alkylcarbonyl, amido or $(C_1$–$C_6)$alkylsulphonyl radical; a $C_1$–$C_6$ carbamylalkyl radical; a tri$(C_1$–$C_6)$alkylsilane$(C_1$–$C_6)$alkyl radical; a $(C_1$–$C_6)$alkylcarboxy$(C_1$–$C_6)$alkyl radical; a $(C_1$–$C_6)$alkylcarbonyl$(C_1$–$C_6)$alkyl radical; an N—$(C_1$–$C_6)$alkylcarbamyl$(C_1$–$C_6)$alkyl radical.

36. The composition of claim 33, wherein the cationic tertiary para-phenylenediamine is such that D is a single bond or an alkylene chain which may be substituted.

37. The composition of claim 33, wherein the cationic tertiary para-phenylenediamine is such that $R_2$ is a trialkylammonium radical.

38. The composition of claim 2, wherein the cationic tertiary para-phenylenediamine is such that $R_2$ represents the onium radical Z corresponding to formula III

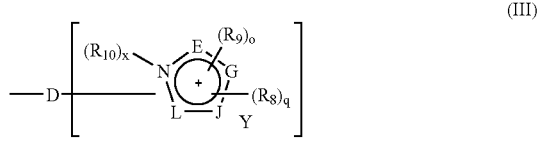

in which
- D is a single bond or a linear or branched $C_1$–$C_{14}$ alkylene chain which may contain one or more heteroatoms chosen from oxygen, sulphur or nitrogen, and which may be substituted with one or more hydroxyl, $C_1$–$C_6$ alkoxy or amino radicals, and which may carry one or more ketone functional groups;
- the vertices E, G, J, L, which are identical or different, represent a carbon, oxygen, sulphur or nitrogen atom to form a pyrrole, pyrazole, imidazole, triazole, oxazole, isooxazole, thiazole, isothiazole ring,
- q is an integer between 0 and 4 inclusive;
- is an integer between 0 and 3 inclusive;
- q+o is an integer between 0 and 4;
- the radicals $R_8$, which are identical or different, represent a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical, a tri($C_1$–$C_6$)alkylsilane($C_1$–$C_6$)alkyl radical, an amido radical, a carboxyl radical, a $C_1$–$C_6$ alkylcarbonyl radical, a thio radical, a $C_1$–$C_6$ thioalkyl radical, a ($C_1$–$C_6$) alkylthio radical, an amino radical, an amino radical which is mono- or di-substituted with a ($C_1$–$C_6$)alkyl, ($C_1$–$C_6$)alkylcarbonyl, amido or ($C_1$–$C_6$)alkylsulphonyl radical; a $C_1$–$C_6$ monohydroxyalkyl radical or a $C_2$–$C_6$ polyhydroxyalkyl radical; it being understood that the radicals $R_8$ are carried by a carbon atom,
- the radicals $R_9$, which are identical or different, represent a $C_1$–$C_6$ alkyl radical, a $C_1$–$C_6$ monohydroxyalkyl radical, a $C_2$–$C_6$ polyhydroxyalkyl radical, a tri($C_1$–$C_6$)alkylsilane($C_1$–$C_6$)alkyl radical, a ($C_1$–$C_6$)alkoxy($C_1$–$C_6$)alkyl radical, a $C_1$–$C_6$ carbamylalkyl radical, a ($C_1$–$C_6$)alkylcarboxy($C_1$–$C_6$)alkyl radical, a benzyl radical; it being understood that the radicals $R_9$ are carried by a nitrogen,
- $R_{10}$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical whose amine is substituted with a ($C_1$–$C_6$)alkyl, ($C_1$–$C_6$)alkylcarbonyl, amido or ($C_1$–$C_6$)alkylsulphonyl radical; a $C_1$–$C_6$ carboxyalkyl radical; a $C_1$–$C_6$ carbamylalkyl radical; a $C_1$–$C_6$ trifluroalkyl radical; a tri($C_1$–$C_6$)alkylsilane($C_1$–$C_6$)alkyl radical; a $C_1$–$C_6$ sulphonamidoalkyl radical; a ($C_1$–$C_6$)alkylcarboxy($C_1$–$C_6$)alkyl radical; a ($C_1$–$C_6$)alkylsulphonyl($C_1$–$C_6$)alkyl radical; a ($C_1$–$C_6$)alkylsulphonyl($C_1$–$C_6$)alkyl radical; a ($C_1$–$C_6$)alkylcarbonyl($C_1$–$C_6$)alkyl radical; an N—($C_1$–$C_6$)alkylcarbamyl($C_1$–$C_6$)alkyl radical; an N—($C_1$–$C_6$) alkylsulphonamido($C_1$–$C_6$)alkyl radical;
- x is 0 or 1
  - when x=0, the linking arm D is attached to the nitrogen atom,
  - when x=1, the linking arm D is attached to one of the vertices E, G, J or L,
- Y is a counter-ion.

39. The composition of claim 38, wherein the cationic tertiary para-phenylenediamine is such that the vertices E, G, J and L form an imidazole ring.

40. The composition of claim 38, wherein the cationic tertiary para-phenylenediamine is such that x is equal to 0, D is a single bond or an alkylene chain which may be substituted.

41. The composition of claim 2, wherein the cationic tertiary para-phenylenediamine is such that $R_2$ represents an onium radical Z corresponding to formula IV

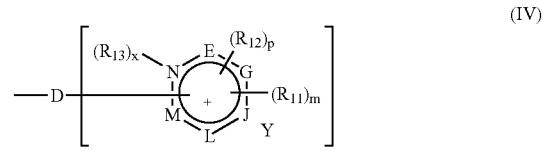

in which:
- D is a single bond or a linear or branched $C_1$–$C_{14}$ alkylene chain which may contain one or more heteroatoms chosen from an oxygen, sulphur or nitrogen atom, and which may be substituted with one or more hydroxyl, $C_1$–$C_6$ alkoxy or amino radicals, and which may carry one or more ketone functional groups;
- the vertices E, G, J, L and M, which are identical or different, represent a carbon, oxygen, sulphur or nitrogen atom to form a ring chosen from the pyridine, pyrimidine, pyrazine, triazine and pyridazine rings;
- p is an integer between 0 and 3 inclusive;
- m is an integer between 0 and 5 inclusive;
- p+m is an integer between 0 and 5;
- the radicals $R_{11}$, which are identical or different, represent a halogen atom, a hydroxyl radical, a $C_1$–$C_6$ alkyl radical, a $C_1$–$C_6$ monohydroxyalkyl radical, a polyhydroxyalkyl radical, a $C_1$–$C_6$ alkoxy radical, a tri($C_1$–$C_6$)alkylsilane($C_1$–$C_6$)alkyl radical, an amido radical, a carboxyl radical, a $C_1$–$C_6$ alkylcarbonyl radical, a thio radical, a $C_1$–$C_6$ thioalkyl radical, a ($C_1$–$C_6$) alkylthio radical, an amino radical, an amino radical which is substituted with a ($C_1$–$C_6$)alkyl, ($C_1$–$C_6$) alkylcarbonyl, amido or ($C_1$–$C_6$)alkylsulphonyl radical; a $C_1$–$C_6$ monohydroxyalkyl radical or a $C_2$–$C_6$ polyhydroxyalkyl radical; it being understood that the radicals $R_{11}$ are carried by a carbon atom,
- the radicals $R_{12}$, which are identical or different, represent a $C_1$–$C_6$ alkyl radical, a $C_1$–$C_6$ monohydroxyalkyl radical, a $C_2$–$C_6$ polyhydroxyalkyl radical, a tri($C_1$–$C_6$)alkylsilane($C_1$–$C_6$)alkyl radical, a ($C_1$–$C_6$)alkoxy($C_1$–$C_6$)alkyl radical, a $C_1$–$C_6$ carbamylalkyl radical, a ($C_1$–$C_6$)alkylcarboxy($C_1$–$C_6$)alkyl radical, a benzyl radical; it being understood that the radicals $R_{12}$ are carried by a nitrogen,
- $R_{13}$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical whose amine is mono- or di-substituted with a ($C_1$–$C_6$)alkyl, ($C_1$–$C_6$) alkylcarbonyl, amido or ($C_1$–$C_6$)alkylsulphonyl radical; a $C_1$–$C_6$ carboxyalkyl radical; a $C_1$–$C_6$ carbamylalkyl radical; a $C_1$–$C_6$ trifluroalkyl radical; a tri($C_1$–$C_6$)alkylsilane($C_1$–$C_6$)alkyl radical; a $C_1$–$C_6$ sulphonamidoalkyl radical; a ($C_1$–$C_6$)alkylcarboxy($C_1$–$C_6$)alkyl radical; a ($C_1$–$C_6$)alkylsulphonyl($C_1$–$C_6$) alkyl radical; a ($C_1$–$C_6$)alkylsulphonyl($C_1$–$C_6$)alkyl radical; a (C$_1$–C$_6$)alkylcarbonyl(C$_1$–C$_6$)alkyl radical; an N—(C$_1$–C$_6$)alkylcarbamyl(C$_1$–C$_6$)alkyl radical; an N—(C$_1$–C$_6$)alkylsulphonamido(C$_1$–C$_6$)alkyl radical;

x is 0 or 1 when x=0, the linking arm D is attached to the nitrogen atom, when x=1, the linking arm D is attached to one of the vertices E, G, J, L or M, Y is a counter-ion.

42. The composition of claim 41, wherein the vertices E, G, J, L and M form, with the nitrogen of the ring, a ring chosen from pyridine and pyrimidine rings.

43. The composition of claim 41, wherein the cationic tertiary para-phenylenediamine is such that x is equal to 0 and R$_{11}$ is chosen from a hydroxyl radical, a C$_1$–C$_6$ alkyl radical, a C$_1$–C$_6$ monohydroxyalkyl radical, a C$_2$–C$_6$ polyhydroxyalkyl radical, a C$_1$–C$_6$ alkoxy radical, a tri(C$_1$–C$_6$)alkylsilane(C$_1$–C$_6$)alkyl radical, an amido radical, a C$_1$–C$_6$ alkylcarbonyl radical, an amino radical, an amino radical which is mono- or di-substituted with a (C$_1$–C$_6$)alkyl, a (C$_1$–C$_6$)alkylcarbonyl, amido or (C$_1$–C$_6$)alkylsulphonyl radical; a C$_1$–C$_6$ monohydroxyalkyl radical or a C$_2$–C$_6$ polyhydroxyalkyl radical and R$_{12}$ is chosen from a C$_1$–C$_6$ alkyl radical, a C$_1$–C$_6$ monohydroxyalkyl radical, a C$_2$–C$_6$ polyhydroxyalkyl radical, a tri(C$_1$–C$_6$)alkylsilane(C$_1$–C$_6$) alkyl radical, a (C$_1$–C$_6$)alkoxy(C$_1$–C$_6$)alkyl radical, a C$_1$–C$_6$ carbamylalkyl radical.

44. The composition of claim 41, wherein the cationic tertiary para-phenylenediamine is such that x is equal to 1 and R$_{13}$ is chosen from a C$_1$–C$_6$ alkyl radical, a C$_1$–C$_6$ monohydroxyalkyl radical; a C$_2$–C$_6$ polyhydroxyalkyl radical; a C$_1$–C$_6$ aminoalkyl radical, a C$_1$–C$_6$ aminoalkyl radical whose amine is mono- or di-substituted with a (C$_1$–C$_6$)alkyl radical, a (C$_1$–C$_6$)alkylcarbonyl radical, an amido radical, a (C$_1$–C$_6$)alkylsulphonyl radical; a C$_1$–C$_6$ carbamylalkyl radical; a tri(C$_1$–C$_6$)alkylsilane(C$_1$–C$_6$)alkyl radical; a (C$_1$–C$_6$) alkylcarbonyl(C$_1$–C$_6$)alkyl radical; an N—(C$_1$–C$_6$)alkylcarbamyl(C$_1$–C$_6$)alkyl radical; R$_{11}$ is chosen from a hydroxyl radical, a C$_1$–C$_6$ alkyl radical, a C$_1$–C$_6$ monohydroxyalkyl radical, a C$_2$–C$_6$ polyhydroxyalkyl radical, a C$_1$–C$_6$ alkoxy radical, a tri(C$_1$–C$_6$)alkylsilane(C$_1$–C$_6$)alkyl radical, an amido radical, a C$_1$–C$_6$ alkylcarbonyl radical, an amino radical, an amino radical which is mono- or di- substituted with a (C$_1$–C$_6$)alkyl, (C$_1$–C$_6$)alkylcarbonyl, amido or (C$_1$–C$_6$)alkylsulphonyl radical; and R$_{12}$ is chosen from a C$_1$–C$_6$ alkyl radical, a C$_1$–C$_6$ monohydroxyalkyl radical, a C$_2$–C$_6$ polyhydroxyalkyl radical, a tri(C$_1$–C$_6$)alkylsilane (C$_1$–C$_6$)alkyl radical, a (C$_1$–C$_6$)alkoxy(C$_1$–C$_6$)alkyl radical, a C$_1$–C$_6$ carbamylalkyl radical.

45. The composition of claim 41, wherein the cationic tertiary para-phenylenediamine is such that R$_{11}$, R$_{12}$ and R$_{13}$ are alkyl radicals which may be substituted.

46. The composition of claim 2, wherein the cationic tertiary para-phenylenediamine is such that the radical R$_2$ is the radical of formula —XP(O)(O—) OCH$_2$CH$_2$N$^+$(CH$_3$)$_3$ where X represents an oxygen atom or a radical —NR$_{14}$,R$_{14}$ representing a hydrogen, a C$_1$–C$_4$ alkyl radical or a hydroxyalkyl radical.

47. The composition of claim 2, wherein the cationic tertiary para-phenylenediamine is such that the radical R$_2$ is a guanidine radical of formula —X—C=NR$_8$—NR$_9$R$_{10}$, X represents an oxygen atom or a radical —NR$_{11}$, R$_8$, R$_9$, R$_{10}$ and R$_{11}$ representing a hydrogen, a C$_1$–C$_4$ alkyl radical or a hydroxyalkyl radical.

48. The composition of claim 2, wherein the cationic tertiary para-phenylene is chosen from the group consisting of:

[1-(4-Aminophenyl)pyrrolidin-3-yl]trimethylammonium chloride,

[1-(4-Aminophenyl)pyrrolidin-3-yl]dimethyltetradecylammonium bromide

N'-[1-(4-Aminophenyl)pyrrolidin-3-yl]-N,N-dimethylguanidinium chloride

N-[1-(4-Aminophenyl)pyrrolidin-3-yl]guanidinium chloride

3-[1-(4-Aminophenyl)pyrrolidin-3-yl]-1-methyl-3H-imidazol-1-ium chloride

[1-(4-Aminophenyl)pyrrolidin-3-yl]-(2-hydroxyethyl) dimethylammonium chloride

[1-(4-Aminophenyl)pyrrolidin-3-yl]dimethyl-(3-trimethylsilanylpropyl)ammonium chloride

[1-(4-Aminophenyl)pyrrolidin-3-yl]-(trimethylammonium-hexyl)dimethylammonium dichloride

[1-(4-Aminophenyl)pyrrolidin-3-yl]oxophosphorylcholine

{2-[1-(4-Aminophenyl)pyrrolidin-3-yloxy]ethyl}trimethylammonium chloride

1-{2-[1-(4-Aminophenyl)pyrrolidin-3-yloxy]ethyl}-1-methylpyrrolidinium chloride

3-{3-[1-(4-Aminophenyl)pyrrolidin-3-yloxy]propyl}-1-methyl-3H-imidazol-1-ium chloride 1-{2-[1-(4-Aminophenyl)pyrrolidin-3-yloxy]ethyl}-1-methylpiperidinium chloride 3-{3-[1-(5-trimethylsilanylethyl-4-Amino-3-trimethylsilanylethylphenyl)pyrrolidin-3-yloxy]propyl}-1-methyl-3H-imidazol-1-ium chloride

[1-(4-Amino-3-methylphenyl)pyrrolidin-3-yl]trimethylammonium chloride

[1-(4-Amino-3-methylphenyl)pyrrolidin-3-yl]dimethyltetradecylammonium chloride

N'-[1-(4-Amino-3-methylphenyl)pyrrolidin-3-yl]-N,N-dimethylguanidinium chloride

N-[1-(4-Amino-3-methylphenyl)pyrrolidin-3-yl]guanidinium chloride

3-[1-(4-Amino-3-methylphenyl)pyrrolidin-3-yl]-1-methyl-3H-imidazol-1-ium chloride

[1-(4-Amino-3-methylphenyl)pyrrolidin-3-yl]-(2-hydroxyethyl)dimethylammonium chloride

[1-(4-Amino-3-methylphenyl)pyrrolidin-3-yl]dimethyl-(3-trimethylsilanylpropylammonium chloride

[1-(4-Amino-3-methylphenyl)pyrrolidin-3-yl]-(trimethylammoniumhexyl-dimethylammonium dichloride

[1-(4-Amino-3-methylphenyl)pyrrolidin-3-yl]oxophosphorylcholine

{2-[1-(4-Amino-3-methylphenyl)pyrrolidin-3-yloxy] ethyl}trimethylammonium chloride 1-{2-[1-(4-Amino-3-methylphenyl)pyrrolidin-3-yloxy] ethyl}-1-methylpyrrolidinium chloride 3-{3-[1-(4-Amino-3-methylphenyl)pyrrolidin-3-yloxy]-propyl}1-methyl-3H-imidazol-1-ium chloride 1-{2-[1-(4-Amino-3-methylphenyl)pyrrolidin-3-yloxy] ethyl}-1-methylpiperidinium chloride

[1-(4-Amino-3-trimethylsilanylethylphenyl)pyrrolidin-3-yl]trimethylammonium chloride 3-[1-(4-Amino-3-trimethylsilanylethylphenyl)pyrrolidin-3-yl]-1-methyl-3H-imidazol-1-ium chloride 3-{3-[1-(4-Amino-3-trimethylsilanylethylphenyl)pyrrolidin-3-yloxy]propyl}-1-methyl-3H-imidazol-1-ium chloride

[1-(5-trimethylsilanylethyl-4-Amino-3-trimethylsilanylethylphenyl)Pyrrolidin-3-yl]trimethylammonium chloride 3-[1-(5-trimethylsilanylethyl-4-Amino-3-trimethylsilanylethylphenyl)pyrrolidin-3-yl]-1-methyl-3H-imidazol-1-ium chloride 1'-(4-Aminophenyl)-1-methyl-[1,3']bipyrrolidinyl-1-ium chloride 1'-(4-Amino-3-methylphenyl)-1-methyl-[1,3']bipyrrolidinyl-1-ium chloride 3-{[1-(4-Aminophenyl)pyrrolidin-3-yl]carbamoylmethyl}-1-methyl-3H-imidazol-1-ium chloride 3-{[1-(4-Amino-3-methylphenyl)pyrrolidin-3-yl]carbamoylmethyl}-1-methyl-3H-imidazol-1-ium chloride 3-[1-(4-Aminophenyl)pyrrolidin-3-yl]-1-(3-trimethylsilanylpropyl)-3H-imidazol-1-ium chloride 3-[1-(4-Aminophenyl)pyrrolidin-3-yl]-1-(3-trimethylsilanylpropyl)-3H-imidazol-1-ium chloride

[1-(4-aminophenyl)pyrrolidin-3-yl]ethyldimethylammonium chloride

[1-(4-aminophenyl)pyrrolidin-3-yl]ethyldimethylammonium iodide

[1-(4-aminophenyl)pyrrolidin-3-yl]propyldimethylammonium iodide,

[1-(4-aminophenyl)pyrrolidin-3-yl]propyldimethylammonium bromide

[1-(4-aminophenyl)pyrrolidin-3-yl]propyldimethylammonium methosulphate

[1-(4-aminophenyl)pyrrolidin-3-yl]butyldimethylammonium iodide

[1-(4-aminophenyl)pyrrolidin-3-yl]pentyldimethylammonium iodide

[1-(4-aminophenyl)pyrrolidin-3-yl]hexyldimethylammonium iodide

[1-(4-aminophenyl)pyrrolidin-3-yl]heptyldimethylammonium iodide

[1-(4-Aminophenyl)pyrrolidin-3-yl]octyldimethylammonium iodide

[1-(4-aminophenyl)pyrrolidin-3-yl]decyldimethylammonium iodide

[1-(4-aminophenyl)pyrrolidin-3-yl]hexadecyldimethylammonium iodide

[1-(4-aminophenyl)pyrrolidin-3-yl]hydroxyethyldimethylammonium chloride

[1-(4-aminophenyl)pyrrolidin-3-yl]hydroxyethyldimethylammonium iodide.

49. The composition of claim 2, wherein the cationic tertiary para-phenylene is chosen from the group consisting of:

[1-(4-Aminophenyl)pyrrolidin-3-yl]trimethylammonium chloride

[1-(4-Aminophenyl)pyrrolidin-3-yl]dimethyltetradecylammonium bromide

N'-[1-(4-Aminophenyl)pyrrolidin-3-yl]-N,N-dimethylguanidinium chloride

N-[1-(4-Aminophenyl)pyrrolidin-3-yl]guanidinium chloride

3-[1-(4-Aminophenyl)pyrrolidin-3-yl]-1-methyl-3H-imidazol-1-ium chloride

[1-(4-Aminophenyl)pyrrolidin-3-yl](2-hydroxyethyl)dimethylammonium chloride

[1-(4-Aminophenyl)pyrrolidin-3-yl]dimethyl-(3-trimethylsilanylpropyl)ammonium chloride

[1-(4-Amino-3-methylphenyl)pyrrolidin-3-yl]trimethylammonium chloride

[1-(4-Amino-3-methylphenyl)pyrrolidin-3-yl]dimethyltetradecylammonium chloride

N'-[1-(4-Amino-3-methylphenyl)pyrrolidin-3-yl]-N,N-dimethylguanidinium chloride

N-[1-(4-Amino-3-methylphenyl)pyrrolidin-3-yl]guanidinium chloride

3-[1-(4-Amino-3-methylphenyl)pyrrolidin-3-yl]-1-methyl-3H-imidazol-1-ium chloride

[1-(4-Amino-3-methylphenyl)pyrrolidin-3-yl]-(2-hydroxyethyl)dimethylammonium chloride

[1-(4-Amino-3-methylphenyl)pyrrolidin-3-yl]dimethyl-(3-trimethylsilanylpropylammonium chloride 1'-(4-Aminophenyl)-1-methyl-[1,3']bipyrrolidinyl-1-ium chloride 1'-(4-Amino-3-methylphenyl)-1-methyl-[1,3']bipyrrolidinyl-1-ium chloride 3-{[1-(4-Aminophenyl)pyrrolidin-3-ylcarbamoyl]methyl}-1-methyl-3H-imidazol-1-ium chloride 3-{[1-(4-Amino-3-methylphenyl)pyrrolidin-3-ylcarbamoyl]methyl}-1-methyl-3H-imidazol-1-ium chloride 3-[1-(4-Aminophenyl)pyrrolidin-3-yl]-1-(3-trimethylsilanylpropyl)-3H-imidazol-1-ium chloride 3-[1-(4-Amino-3-methylphenyl)pyrrolidin-3-yl]-1-(3-trimethylsilanyl-propyl)-3H-imidazol-1-ium chloride

[1-(4-aminophenyl)pyrrolidin-3-yl]ethyldimethylammonium chloride

[1-(4-aminophenyl)pyrrolidin-3-yl]ethyldimethylammonium iodide

[1-(4-Aminophenyl)pyrrolidin-3-yl]propyldimethylammonium iodide

[1-(4-aminophenyl)pyrrolidin-3-yl]propyldimethylammonium bromide

[1-(4-aminophenyl)pyrrolidin-3-yl]propyldimethylammonium methosulphate

[1-(4-aminophenyl)pyrrolidin-3-yl]butyldimethylammonium iodide

[1-(4-aminophenyl)pyrrolidin-3-yl]pentyldimethylammonium iodide

[1-(4-aminophenyl)pyrrolidin-3-yl]hexyldimethylammonium iodide

[1-(4-aminophenyl)pyrrolidin-3-yl]heptyldimethylammonium iodide

[1-(4-aminophenyl)pyrrolidin-3-yl]octyldimethylammonium iodide

[1-(4-aminophenyl)pyrrolidin-3-yl]decyldimethylammonium iodide

[1-(4-aminophenyl)pyrrolidin-3-yl]hexadecyldimethylammonium iodide

[1-(4-aminophenyl)pyrrolidin-3-yl]hydroxyethyldimethylammonium chloride

[1-(4-aminophenyl)pyrrolidin-3-yl]hydroxyethyldimethylammonium iodide.

50. The composition of claim 2, wherein the cationic tertiary para-phenylene is chosen from the group consisting of:

[1-(4-Aminophenyl)pyrrolidin-3-yl]trimethylammonium chloride

[1-(4-Aminophenyl)pyrrolidin-3-yl]dimethyltetradecylammonium bromide

N'-[1-(4-Aminophenyl)pyrrolidin-3-yl]-N,N-dimethylguanidinium chloride

N-[1-(4-Aminophenyl)pyrrolidin-3-yl]guanidinium chloride

3-[1-(4-Aminophenyl)pyrrolidin-3-yl]-1-methyl-3H-imidazol-1-ium chloride

[1-(4-Aminophenyl)pyrrolidin-3-yl]-(2-hydroxyethyl)dimethylammonium chloride

[1-(4-Aminophenyl)pyrrolidin-3-yl]dimethyl-(3-trimethylsilanylpropyl)ammonium chloride

[1-(4-Aminophenyl)pyrrolidin-3-yl]-(trimethylammoniumhexyl)dimethylammonium dichloride 1'-(4-Aminophenyl)-1-methyl-[1,3']bipyrrolidinyl-1-ium chloride 3-[1-(4-Aminophenyl)pyrrolidin-3-yl]-1-(3-trimethylsilanylpropyl)-3H-imidazol-1-ium chloride 3-[1-(4-Amino-3-methylphenyl)pyrrolidin-3-yl]-1-(3-trimethylsilanylpropyl)-3H-imidazol-1-ium chloride

[1-(4-aminophenyl)pyrrolidin-3-yl]ethyldimethylammonium chloride

[1-(4-aminophenyl)pyrrolidin-3-yl]ethyldimethylammonium iodide

[1-(4-aminophenyl)pyrrolidin-3-yl]propyldimethylammonium iodide

[1-(4-aminophenyl)pyrrolidin-3-yl]propyldimethylammonium bromide

[1-(4-aminophenyl)pyrrolidin-3-yl]propyldimethylammonium methosulphate

[1-(4-aminophenyl)pyrrolidin-3-yl]butyldimethylammonium iodide

[1-(4-aminophenyl)pyrrolidin-3-yl]pentyldimethylammonium iodide

[1-(4-aminophenyl)pyrrolidin-3-yl]hexyldimethylammonium iodide

[1-(4-aminophenyl)pyrrolidin-3-yl]heptyldimethylammonium iodide

[1-(4-aminophenyl)pyrrolidin-3-yl]octyldimethylammonium iodide

[1-(4-aminophenyl)pyrrolidin-3-yl]decyldimethylammonium iodide

[1-(4-aminophenyl)pyrrolidin-3-yl]hexadecyldimethylammonium iodide

[1-(4-aminophenyl)pyrrolidin-3-yl]hydroxyethyldimethylammonium chloride

[1-(4-aminophenyl)pyrrolidin-3-yl]hydroxyethyldimethylammonium iodide.

51. The composition of claim 2, wherein the cationic tertiary para-phenylene is chosen from the group consisting of:
[1-(4-Aminophenyl)pyrrolidin-3-yl]trimethylammonium chloride
3-[1-(4-Aminophenyl)pyrrolidin-3-yl]-1-methyl-3H-imidazol-1-ium chloride
[1-(4-Aminophenyl)pyrrolidin-3-yl]-(2-hydroxyethyl)dimethylammonium chloride
1'-(4-Aminophenyl)-1-methyl-[1,3']bipyrrolidinyl-1-ium chloride.

52. The composition of claim 2, wherein the cationic tertiary para-phenylene is chosen from the group consisting of:
[1-(4-Aminophenyl)pyrrolidin-3-yl]trimethylammonium chloride, and
[1-(4-Aminophenyl)pyrrolidin-3-yl]-(2-hydroxyethyl)dimethylammonium chloride.

53. The composition of claim 3, wherein the cationic tertiary para-phenylenediamine is such that n is equal to 0.

54. The composition of claim 3, wherein the cationic tertiary para-phenylenediamine is such that n is equal to 1 and $R_1$ is chosen from the group consisting of a halogen atom; a saturated or unsaturated, aliphatic or alicylic, $C_1$–$C_6$ hydrocarbon chain; it being possible for one or more carbon atoms to be replaced by an oxygen, nitrogen, silicon or sulphur atom, or by an $SO_2$ group, the radical $R_1$ not containing a peroxide bond, or diazo, nitro or nitroso radicals.

55. The composition of claim 3, wherein the cationic tertiary para-phenylenediamine is such that $R_1$ is chosen from chlorine, bromine, $C_1$–$C_4$ alkyl, $C_1$–$C_4$ hydroxyalkyl, $C_1$–$C_4$ aminoalkyl, $C_1$–$C_4$ alkoxy or $C_1$–$C_4$ hydroxyalkoxy radicals.

56. The composition of claim 55, wherein the cationic tertiary para-phenylenediamine is such that $R_1$ is chosen from a methyl, hydroxymethyl, 2-hydroxyethyl, 1,2-dihydroxyethyl, methoxy, isopropyloxy or 2-hydroxyethoxy radical.

57. The composition of claim 3, wherein the cationic tertiary para-phenylenediamine is such that $R_2$ represents the onium radical Z corresponding to formula (II)

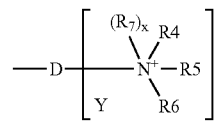

in which
D is a single bond of a linear or branched $C_1$–$C_{14}$ alkylene chain which may contain one or more heteroatoms chosen from oxygen, sulphur or nitrogen, and which may be substituted with one or more hydroxyl, $C_1$–$C_6$ alkoxy or amino radicals and which may carry one or more ketone functional groups;

$R_4$, $R_5$ and $R_6$, taken separately, represent a $C_1$–$C_{15}$ alkyl radical; a $C_1$–$C_6$ monohydroxyalkyl radical; a $C_2$–$C_6$ polyhydroxyalkyl radical; a $(C_1$–$C_6)$alkoxy$(C_1$–$C_6)$ alkyl radical; an aryl radical; a benzyl radical; a $C_1$–$C_6$ amidoalkyl radical; a tri$(C_1$–$C_6)$alkylsilane$(C_1$–$C_6)$ alkyl radical; a $C_1$–$C_6$ aminoalkyl radical; a $C_1$–$C_6$ aminoalkyl radical in which the amine is mono- or di-substituted with a $C_1$–$C_4$ alkyl, $(C_1$–$C_6)$alkylcarbonyl, amido or $(C_1$–$C_6)$alkylsulphonyl radical; or $R_4$, $R_5$ and $R_6$ together, in pairs, form, with the nitrogen atom to which they are attached, a 4-, 5-, 6- or 7-membered saturated carbon ring which may contain one or more heteroatoms, it being possible for the cationic ring to be substituted with a halogen atom, a hydroxyl radical, a $C_1$–$C_6$ alkyl radical, a $C_1$–$C_6$ monohydroxyalkyl radical, a $C_2$–$C_6$ polyhydroxy-alkyl radical, a $C_1$–$C_6$ alkoxy radical, a tri$(C_1$–$C_6)$alkylsilane $(C_1$–$C_6)$alkyl radical, an amido radical, a carboxyl radical, a $(C_1$–$C_6)$alkylcarbonyl radical, a thio (—SH) radical, a $C_1$–$C_6$ thioalkyl (—R—SH) radical, a $(C_1$–$C_6)$alkylthio radical, an amino radical, an amino radical which is mono- or di-substituted with a $(C_1$–$C_6)$ alkyl, $(C_1$–$C_6)$alkylcarbonyl, amido or $(C_1$–$C_6)$alkylsulphonyl radical;

$R_7$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical; a $C_1$–$C_6$ aminoalkyl radical whose amine is mono- or di-substituted with a $(C_1$–$C_6)$alkyl, $(C_1$–$C_6)$ alkylcarbonyl, amido or $(C_1$–$C_6)$alkylsulphonyl radical; a $C_1$–$C_6$ carboxyalkyl radical; a $C_1$–$C_6$ carbamylalkyl radical; a $C_1$–$C_6$ trifluroalkyl radical; a tri $(C_1$–$C_6)$alkylsilane$(C_1$–$C_6)$alkyl radical; a $C_1$–$C_6$ sulphonamidoalkyl radical; a $(C_1$–$C_6)$alkylcarboxy $(C_1$–$C_6)$alkyl radical; a $(C_1$–$C_6)$alkylsulphinyl$(C_1$–$C_6)$ alkyl radical; a $(C_1$–$C_6)$alkylsulphonyl$(C_1$–$C_6)$alkyl radical; a $C_1$–$C_6)$alkylcarbonyl$(C_1$–$C_6)$alkyl radical; an N—($C_1$–$C_6$)alkylcarbamyl($C_1$–$C_6$)alkyl radical; an N—($C_1$–$C_6$)alkylsulphonamido($C_1$–$C_6$)alkyl radical;

x is 0 or 1, when x=0, then the linking arm is attached to the nitrogen atom carrying the radicals $R_4$ to $R_6$;

when x=1, then two of the radicals $R_4$ to $R_6$ form, together with the nitrogen atom to which they are attached, a 4-, 5-, 6- or 7-membered saturated ring and D is linked to the carbon atom of the saturated ring;

Y is a counter-ion.

58. The composition of claim 57, wherein the cationic tertiary para-phenylenediamine is such that $R_2$ corresponds to formula II in which x is equal to 0 and $R_4$, $R_5$ and $R_6$ separately are preferably chosen from a $C_1$–$C_6$ alkyl radical, a $C_1$–$C_4$ monohydroxyalkyl radical, a $C_2$–$C_4$ polyhydroxyalkyl radical, a ($C_1$–$C_6$)alkoxy($C_1$–$C_4$)alkyl radical, a $C_1$–$C_6$ amidoalkyl radical, a tri($C_1$–$C_6$)alkylsilane($C_1$–$C_6$)alkyl radical, or $R_4$ with $R_5$ form together an azetidine ring, a pyrrolidine, piperidine, piperazine or morpholine ring, $R_6$ being chosen in this case from a $C_1$–$C_6$ alkyl radical; a $C_1$–$C_6$ monohydroxyalkyl radical, a $C_2$–$C_6$ polyhydroxyalkyl radical; a $C_1$–$C_6$ aminoalkyl radical, an aminoalkyl radical which is mono- or di-substituted with a ($C_1$–$C_6$)alkyl radical, a ($C_1$–$C_6$)alkylcarbonyl, amido or ($C_1$–$C_6$)alkylsulphonyl radical; a $C_1$–$C_6$ carbamylalkyl radical; a tri($C_1$–$C_6$)alkylsilane($C_1$–$C_6$)alkyl radical; a ($C_1$–$C_6$)alkylcarboxy($C_1$—$C_6$)alkyl radical; a ($C_1$–$C_6$)alkylcarbonyl($C_1$–$C_6$)alkyl radical; an ($C_1$–$C_6$)alkylcarbamyl($C_1$–$C_6$)alkyl radical.

59. The composition of claim 57, wherein the cationic tertiary para-phenylenediamine is such that $R_2$ corresponds to formula II in which x is equal to 1 and $R_7$ is chosen from a $C_1$–$C_6$ alkyl radical; a $C_1$–$C_6$ monohydroxyalkyl radical; a $C_2$–$C_6$ polyhydroxy-alkyl radical; a $C_1$–$C_6$ aminoalkyl radical, a $C_1$–$C_6$ aminoalkyl radical whose amine is mono- or di-substited with a ($C_1$–$C_6$)alkyl, ($C_1$–$C_6$)alkylcarbonyl, amido or a ($C_1$–$C_6$)alkylsulphonyl radical; a $C_1$–$C_6$ carbamylalkyl radical, a tri($C_1$–$C_6$)alkylsilane($C_1$–$C_6$)alkyl radical; a ($C_1$–$C_6$)alkylcarboxy($C_1$–$C_6$)alkyl radical; a ($C_1$–$C_6$)alkylcarbonyl($C_1$–$C_6$)alkyl radical; an N—($C_1$–$C_6$)alkylcarbamyl($C_1$–$C_6$)alkyl radical; $R_4$ with $R_5$ together form an azetidine, pyrrolidine, piperidine, piperazine or morpholine ring, $R_6$ being chosen in this case from a $C_1$–$C_6$ alkyl radical; a $C_1$–$C_6$ monohydroxyalkyl radical; a $C_2$–$C_6$ polyhydroxyl alkyl radical; a $C_1$–$C_6$ aminoalkyl radical; a $C_1$–$C_6$ aminoalkyl radical whose amine is mono- or di-substituted with a ($C_1$–$C_6$)alkyl, ($C_1$–$C_6$)alkylcarbonyl, amido or ($C_1$–$C_6$)alkylsulphonyl radical; a $C_1$–$C_6$ carbamylalkyl radical; a tri($C_1$–$C_6$)alkylsilane($C_1$–$C_6$)alkyl radical; a ($C_1$–$C_6$)alkylcarboxy($C_1$–$C_6$)alkyl radical; a ($C_1$–$C_6$)alkylcarbonyl($C_1$–$C_6$)alkyl radical; an N—($C_1$–$C_6$)alkylcarbamyl($C_1$–$C_6$)alkyl radical.

60. The composition of claim 57, wherein the cationic tertiary para-phenylenediamine is such that D is a single bond or an alkylene chain which may be substituted.

61. The composition of claim 57, wherein the cationic tertiary para-phenylenediamine is such that $R_2$ is a trialkylammonium radical.

62. The composition of claim 3, wherein the cationic tertiary para-phenylenediamine is such that $R_2$ represents the onium radical Z corresponding to formula III

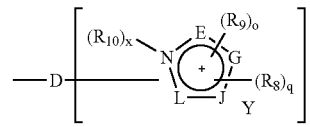

(III)

in which

D is a single bond or a linear or branched $C_1$–$C_{14}$ alkylene chain which may contain one or more heteroatoms chosen from oxygen, sulphur or nitrogen, and which may be substituted with one or more hydroxyl, $C_1$–$C_6$ alkoxy or amino radicals, and which may carry one or more ketone functional groups;

the vertices E, G, J, L, which are identical or different, represent a carbon, oxygen, sulphur or nitrogen atom to form a pyrrole, pyrazole, imidazole, triazole, oxazole, isooxazole, thiazole, isothiazole ring, q is an integer between 0 and 4 inclusive;

is an integer between 0 and 3 inclusive;

q+o is an integer between 0 and 4;

the radicals $R_8$, which are identical or different, represent a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical, a tri($C_1$–$C_6$)alkylsilane($C_1$–$C_6$)alkyl radical, an amido radical, a carboxyl radical, a $C_1$–$C_6$ alkylcarbonyl radical, a thio radical, a $C_1$–$C_6$ thioalkyl radical, a ($C_1$–$C_6$) alkylthio radical, an amino radical, an amino radical which is mono- or di-substituted with a ($C_1$–$C_6$)alkyl, ($C_1$–$C_6$)alkylcarbonyl, amido or ($C_1$–$C_6$)alkylsulphonyl radical; a $C_1$–$C_6$ monohydroxyalkyl radical or a $C_2$–$C_6$ polyhydroxyalkyl radical; it being understood that the radicals $R_8$ are carried by a carbon atom, the radicals $R_9$, which are identical or different, represent a $C_1$–$C_6$ alkyl radical, a $C_1$–$C_6$ monohydroxyalkyl radical, a $C_2$–$C_6$ polyhydroxyalkyl radical, a tri($C_1$–$C_6$) alkylsilane($C_1$–$C_6$)alkyl radical, a ($C_1$–$C_6$)alkoxy ($C_1$–$C_6$)alkyl radical, a $C_1$–$C_6$ carbamylalkyl radical, a ($C_1$–$C_6$)alkylcarboxy($C_1$–$C_6$)alkyl radical, a benzyl radical; it being understood that the radicals $R_9$ are carried by a nitrogen, $R_{10}$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical whose amine is substituted with a ($C_1$–$C_6$)alkyl, ($C_1$–$C_6$)alkylcarbonyl, amido or ($C_1$–$C_6$)alkylsulphonyl radical; a $C_1$–$C_6$ carboxyalkyl radical; a $C_1$–$C_6$ carbamylalkyl radical; a $C_1$–$C_6$ trifluroalkyl radical; a tri($C_1$–$C_6$)alkylsilane ($C_1$–$C_6$)alkyl radical; a $C_1$–$C_6$ sulphonamidoalkyl radical; a ($C_1$–$C_6$)alkylcarboxy($C_1$–$C_6$)alkyl radical; a ($C_1$–$C_6$)alkylsulphonyl($C_1$–$C_6$)alkyl radical; a ($C_1$–$C_6$) alkylsulphonyl($C_1$–$C_6$)alkyl radical; a ($C_1$–$C_6$)alkylcarbonyl($C_1$–$C_6$)alkyl radical; an N—($C_1$–$C_6$)alkylcarbamyl($C_1$–$C_6$)alkyl radical; an N—($C_1$–$C_6$) alkylsulphonamido($C_1$–$C_6$)alkyl radical;

x is 0 or 1 when x=0, the linking arm D is attached to the nitrogen atom, when x=1, the linking arm D is attached to one of the vertices E, G, J or L, Y is a counter-ion.

63. The composition of claim 62, wherein the cationic tertiary para-phenylenediamine is such that the vertices E, G, J and L form an imidazole ring.

64. The composition of claim 62, wherein the cation tertiary para-phenylenediamine is such that x is equal to 0, D is a single bond or an alkylene chain which may be substituted.

65. The composition of claim 3, wherein the cationic tertiary para-phenylenediamine is such that $R_2$ represents an onium radical Z corresponding to formula IV

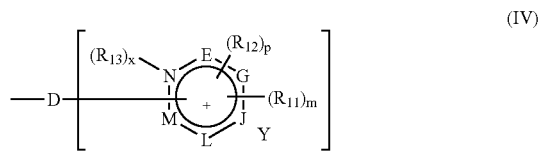

in which:
- D is a single bond or a linear or branched $C_1$–$C_{14}$ alkylene chain which may contain one or more heteroatoms chosen from an oxygen, sulphur or nitrogen atom, and which may be substituted with one or more hydroxyl, $C_1$–$C_6$ alkoxy or amino radicals, and which may carry one or more ketone functional groups;
- the vertices E, G, J, L and M, which are identical or different, represent a carbon, oxygen, sulphur or nitrogen atom to form a ring chosen from the pyridine, pyrimidine, pyrazine, triazine and pyridazine rings;
- p is an integer between 0 and 3 inclusive;
- m is an integer between 0 and 5 inclusive;
- p+m is an integer between 0 and 5;
- the radicals $R_{11}$, which are identical or different, represent a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical, a tri($C_1$–$C_6$)alkylsilane($C_1$–$C_6$)alkyl radical, an amido radical, a carboxyl radical, a $C_1$–$C_6$ alkylcarbonyl radical, a thio radical, a $C_1$–$C_6$ thioalkyl radical, a ($C_1$–$C_6$) alkylthio radical, an amino radical, an amino radical which is substituted with a ($C_1$–$C_6$)alkyl, ($C_1$–$C_6$) alkylcarbonyl, amido or ($C_1$–$C_6$)alkylsulphonyl radical; a $C_1$–$C_6$ monohydroxyalkyl radical or a $C_2$–$C_6$ polyhydroxyalkyl radical; it being understood that the radicals $R_{11}$ are carried by a carbon atom,
- the radicals $R_{12}$, which are identical or different, represent a $C_1$–$C_6$ alkyl radical, a $C_1$–$C_6$ monohydroxyalkyl radical, a $C_2$–$C_6$ polyhydroxyalkyl radical, a tri($C_1$–$C_6$) alkylsilane($C_1$–$C_6$)alkyl radical, a ($C_1$–$C_6$)alkoxy ($C_1$–$C_6$)alkyl radical, a $C_1$–$C_6$ carbamylalkyl radical, a ($C_1$–$C_6$)alkylcarboxy($C_1$–$C_6$)alkyl radical, a benzyl radical; it being understood that the radicals $R_{12}$ are carried by a nitrogen,
- $R_{13}$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical whose amine is mono- or di-substituted with a ($C_1$–$C_6$)alkyl, ($C_1$–$C_6$) alkylcarbonyl, amido or ($C_1$–$C_6$)alkylsulphonyl radical; a $C_1$–$C_6$ carboxyalkyl radical; a $C_1$–$C_6$ carbamylalkyl radical; a $C_1$–$C_6$ trifluroalkyl radical; a tri ($C_1$–$C_6$)alkylsilane($C_1$–$C_6$)alkyl radical; a $C_1$–$C_6$ sulphonamidoalkyl radical; a ($C_1$–$C_6$)alkylcarboxy ($C_1$–$C_6$)alkyl radical; a ($C_1$–$C_6$)alkylsulphonyl($C_1$–$C_6$) alkyl radical; a ($C_1$–$C_6$)alkylsulphonyl($C_1$–$C_6$)alkyl radical; a ($C_1$–$C_6$)alkylcarbonyl($C_1$–$C_6$)alkyl radical; an N—($C_1$–$C_6$)alkylcarbamyl($C_1$–$C_6$)alkyl radical; an N—($C_1$–$C_6$)alkylsulphonamido($C_1$–$C_6$)alkyl radical;
- x is 0 or 1
  - when x=0, the linking arm D is attached to the nitrogen atom,
  - when x=1, the linking arm D is attached to one of the vertices E, G, J, L or M,
- Y is a counter-ion.

66. The composition of claim 65, wherein the vertices E, G, J, L and M form, with the nitrogen of the ring, a ring chosen from pyridine and pyrimidine rings.

67. The composition of claim 65, wherein the cationic tertiary para-phenylenediamine is such that x is equal to 0 and $R_{11}$ is chosen from a hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical, a tri($C_1$–$C_6$) alkylsilane($C_1$–$C_6$)alkyl radical, an amido radical, a $C_1$–$C_6$ alkylcarbonyl radical, an amino radical, an amino radical which is mono- or di-substituted with a ($C_1$–$C_6$)alkyl, a ($C_1$–$C_6$)alkylcarbonyl, amido or ($C_1$–$C_6$)alkylsulphonyl radical; a $C_1$–$C_6$ monohydroxyalkyl radical or a $C_2$–$C_6$ polyhydroxyalkyl radical and $R_{12}$ is chosen from a $C_1$–$C_6$ alkyl radical, a $C_1$–$C_6$ monohydroxyalkyl radical, a $C_2$–$C_6$ polyhydroxyalkyl radical, a tri($C_1$–$C_6$)alkylsilane($C_1$–$C_6$) alkyl radical, a ($C_1$–$C_6$)alkoxy($C_1$–$C_6$)alkyl radical, a $C_1$–$C_6$ carbamyl radical.

68. The composition of claim 65, wherein the cationic tertiary para-phenylenediamine is such that x is equal to 1 and $R_{13}$ is chosen from a $C_1$–$C_6$ alkyl radical; a $C_1$–$C_6$ monohydroxyalkyl radical; a $C_2$–$C_6$ polyhydroxyalkyl radical; a $C_1$–$C_6$ aminoalkyl radical, a $C_1$–$C_6$ aminoalkyl radical whose amine is mono- or di-substituted with a ($C_1$–$C_6$)alkyl radical, a ($C_1$–$C_6$)alkylcarbonyl radical, an amido radical, a ($C_1$–$C_6$)alkylsulphonyl radical; a $C_1$–$C_6$ carbamylalkyl radical; a tri($C_1$–$C_6$)alkylsilane($C_1$–$C_6$)alkyl radical; a ($C_1$–$C_6$) alkylcarbonyl($C_1$–$C_6$)alkyl radical; an N—($C_1$–$C_6$)alkylcarbamyl($C_1$–$C_6$)alkyl radical; $R_{11}$ is chosen from a hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical, a tri($C_1$–$C_6$)alkylsilane($C_1$–$C_6$)alkyl radical, an amido radical, a $C_1$–$C_6$ alkylcarbonyl radical, an amino radical, an amino radical which is mono- or di- substituted with a ($C_1$–$C_6$)alkyl, ($C_1$–$C_6$)alkylcarbonyl, amido or ($C_1$–$C_6$)alkylsulphonyl radical; and $R_{12}$ is chosen from a $C_1$–$C_6$ alkyl radical, a $C_1$–$C_6$ monohydroxyalkyl radical, a $C_2$–$C_6$ polyhydroxyalkyl radical, a tri($C_1$–$C_6$)alkylsilane ($C_1$–$C_6$)alkyl radical, a ($C_1$–$C_6$)alkoxy($C_1$–$C_6$)alkyl radical, a $C_1$–$C_6$ carbamylalkyl radical.

69. The composition of claim 65, wherein the cationic tertiary para-phenylenediamine is such that $R_{11}$, $R_{12}$ and $R_{13}$ are alkyl radicals which may be substituted.

70. The composition of claim 3, wherein the cationic tertiary para-phenylenediamine is such that the radical $R_2$ is the radical of formula —XP(O)(O—) OCH$_2$CH$_2$N$^+$(CH$_3$)$_3$ where X represents an oxygen atom or a radical —NR$_{14}$, R$_{14}$ representing a hydrogen, a $C_1$–$C_4$ alkyl radical or a hydroxyalkyl radical.

71. The composition of claim 3, wherein the cationic tertiary para-phenylenediamine is such that the radical $R_2$ is a guanidine radical of formula —X—C=NR$_8$—NR$_9$R$_{10}$, X represents an oxygen atom or a radical —NR$_{11}$, R$_8$, R$_9$, R$_{10}$ and R$_{11}$ representing a hydrogen, a $C_1$–$C_4$ alkyl radical or a hydroxyalkyl radical.

72. The composition of claim 3, wherein the cationic tertiary para-phenylene is chosen from the group consisting of:

[1-(4-Aminophenyl)pyrrolidin-3-yl]trimethylammonium chloride,
[1-(4-Aminophenyl)pyrrolidin-3-yl]dimethyltetradecylammonium bromide
N'-[1-(4-Aminophenyl)pyrrolidin-3-yl]-N,N-dimethylguanidinium chloride
N-[1-(4-Aminophenyl)pyrrolidin-3-yl]guanidinium chloride
3-[1-(4-Aminophenyl)pyrrolidin-3-yl]-1-methyl-3H-imidazol-1-ium chloride
[1-(4-Aminophenyl)pyrrolidin-3-yl]-(2-hydroxyethyl)dimethylammonium chloride
[1-(4-Aminophenyl)pyrrolidin-3-yl]dimethyl-(3-trimethylsilanylpropyl)ammonium chloride
[1-(4-Aminophenyl)pyrrolidin-3-yl]-(trimethylammonium-hexyl)dimethylammonium dichloride
[1-(4-Aminophenyl)pyrrolidin-3-yl]oxophosphorylcholine
{2-[1-(4-Aminophenyl)pyrrolidin-3-yloxy]ethyl}trimethylammonium chloride
1-{2-[1-(4-Aminophenyl)pyrrolidin-3-yloxy]ethyl}-1-methylpyrrolidinium chloride
3-{3-[1-(4-Aminophenyl)pyrrolidin-3-yloxy]propyl}-1-methyl-3H-imidazol-1-ium chloride
1-{2-[1-(4-Aminophenyl)pyrrolidin-3-yloxy]ethyl}-1-methylpiperidinium chloride
3-{3-[1-(5-trimethylsilanylethyl-4-Amino-3-trimethylsilanylethylphenyl)pyrrolidin-3-yloxy]propyl}-1-methyl-3H-imidazol-1-ium chloride
[1-(4-Amino-3-methylphenyl)pyrrolidin-3-yl]trimethylammonium chloride
[1-(4-Amino-3-methylphenyl)pyrrolidin-3-yl]dimethyltetradecylammonium chloride
N'-[1-(4-Amino-3-methylphenyl)pyrrolidin-3-yl]-N,N-dimethylguanidinium chloride
N-[1-(4-Amino-3-methylphenyl)pyrrolidin-3-yl]guanidinium chloride
3-[1-(4-Amino-3-methylphenyl)pyrrolidin-3-yl]-1-methyl-3H-imidazol-1-ium chloride
[1-(4-Amino-3-methylphenyl)pyrrolidin-3-yl]-(2-hydroxyethyl)dimethylammonium chloride
[1-(4-Amino-3-methylphenyl)pyrrolidin-3-yl]dimethyl-(3-trimethylsilanylpropylammonium chloride
[1-(4-Amino-3-methylphenyl)pyrrolidin-3-yl]-(trimethylammoniumhexyl-dimethylammonium dichloride
[1-(4-Amino-3-methylphenyl)pyrrolidin-3-yl]oxophosphorylcholine
{2-[1-(4-Amino-3-methylphenyl)pyrrolidin-3-yloxy]ethyl}trimethylammonium chloride
1-{2-[1-(4-Amino-3-methylphenyl)pyrrolidin-3-yloxy]ethyl}-1-methylpyrrolidinium chloride
3-{3-[1-(4-Amino-3-methylphenyl)pyrrolidin-3-yloxy]-propyl}1-methyl-3H-imidazol-1-um chloride
1-{2-[1-(4-Amino-3-methylphenyl)pyrrolidin-3-yloxy]ethyl}-1-methylpiperidinium chloride
[1-(4-Amino-3-trimethylsilanylethylphenyl)pyrrolidin-3-yl]trimethylammonium chloride
3-[1-(4-Amino-3-trimethylsilanylethylphenyl)pyrrolidin-3-yl]-1-methyl-3H-imidazol-1-ium chloride
3-{3-[1-(4-Amino-3-trimethylsilanylethylphenyl)pyrrolidin-3-yloxy]propyl}-1-methyl-3H-imidazol-1-ium chloride
[1-(5-trimethylsilanylethyl-4-Amino-3-trimethylsilanylethylphenyl)pyrrolidin-3-yl]trimethylammonium chloride
3-[1-(5-trimethylsilanylethyl-4-Amino-3-trimethylsilanylethylphenyl)pyrrolidin-3-yl]-1-methyl-3H-imidazol-1-ium chloride
1'-(4-Aminophenyl)-1-methyl-[1,3']bipyrrolidinyl-1-ium chloride
1'-(4-Amino-3-methylphenyl)-1-methyl-[1,3']bipyrrolidinyl-1-ium chloride
3-{[1-(4-Aminophenyl)pyrrolidin-3-yl]carbamoylmethyl}-1-methyl-3H-imidazol-1-ium chloride
3-{[1-(4-Amino-3-methylphenyl)pyrrolidin-3-yl]carbamoylmethyl}-1-methyl-3H-imidazol-1-ium chloride
3-[1-(4-Aminophenyl)pyrrolidin-3-yl]-1-(3-trimethylsilanylpropyl)-3H-imidazol-1-ium chloride
3-[1-(4-Aminophenyl)pyrrolidin-3-yl]-1-(3-trimethylsilanylpropyl)-3H-imidazol-1-ium chloride
[1-(4-aminophenyl)pyrrolidin-3-yl]ethyldimethylammonium chloride
[1-(4-aminophenyl)pyrrolidin-3-yl]ethyldimethylammonium iodide
[1-(4-aminophenyl)pyrrolidin-3-yl]propyldimethylammonium iodide,
[1-(4-aminophenyl)pyrrolidin-3-yl]propyldimethylammonium bromide
[1-(4-aminophenyl)pyrrolidin-3-yl]propyldimethylammonium methosulphate
[1-(4-aminophenyl)pyrrolidin-3-yl]butyldimethylammonium iodide
[1-(4-aminophenyl)pyrrolidin-3-yl]pentyldimethylammonium iodide
[1-(4-aminophenyl)pyrrolidin-3-yl]hexyldimethylammonium iodide
[1-(4-aminophenyl)pyrrolidin-3-yl]heptyldimethylammonium iodide
[1-(4-Aminophenyl)pyrrolidin-3-yl]octyldimethylammonium iodide
[1-(4-aminophenyl)pyrrolidin-3-yl]decyldimethylammonium iodide
[1-(4-aminophenyl)pyrrolidin-3-yl]hexadecyldimethylammonium iodide
[1-(4-aminophenyl)pyrrolidin-3-yl]hydroxyethyldimethylammonium chloride
[1-(4-aminophenyl)pyrrolidin-3-yl]hydroxyethyldimethylammonium iodide.

73. The composition of claim 3, wherein the cationic tertiary para-phenylene is chosen from the group consisting of:

[1-(4-Aminophenyl)pyrrolidin-3-yl]trimethylammonium chloride
[1-(4-Aminophenyl)pyrrolidin-3-yl]dimethyltetradecylammonium bromide
N'-[1-(4-Aminophenyl)pyrrolidin-3-yl]-N,N-dimethylguanidinium chloride
N-[1-(4-Aminophenyl)pyrrolidin-3-yl]guanidinium chloride
3-[1-(4-Aminophenyl)pyrrolidin-3-yl]-1-methyl-3H-imidazol-1-ium chloride
[1-(4-Aminophenyl)pyrrolidin-3-yl](2-hydroxyethyl)dimethylammonium chloride
[1-(4-Aminophenyl)pyrrolidin-3-yl]dimethyl-(3-trimethylsilanylpropyl)ammonium chloride
[1-(4-Amino-3-methylphenyl)pyrrolidin-3-yl]trimethylammonium chloride
[1-(4-Amino-3-methylphenyl)pyrrolidin-3-yl]dimethyltetradecylammonium chloride N'-[1-(4-Amino-3-methylphenyl)pyrrolidin-3-yl]-N,N-dimethylguanidinium chloride
N—[1-(4-Amino-3-methylphenyl)pyrrolidin-3-yl]guanidinium chloride
3-[1-(4-Amino-3-methylphenyl)pyrrolidin-3-yl]-1-methyl-3H-imidazol-1-ium chloride
[1-(4-Amino-3-methylphenyl)pyrrolidin-3-yl]-(2-hydroxyethyl)dimethylammonium chloride
[1-(4-Amino-3-methylphenyl)pyrrolidin-3-yl]dimethyl-(3-trimethylsilanylpropylammonium chloride
1'-(4-Aminophenyl)-1-methyl-[1,3']bipyrrolidinyl-1-ium chloride
1'-(4-Amino-3-methylphenyl)-1-methyl-[1,3']bipyrrolidinyl-1-ium chloride
3-{[1-(4-Aminophenyl)pyrrolidin-3-ylcarbamoyl]methyl}-1-methyl-3H-imidazol-1-ium chloride
3-{[1-(4-Amino-3-methylphenyl)pyrrolidin-3-ylcarbamoyl]methyl}-1-methyl-3H-imidazol-1-ium chloride
3-[1-(4-Aminophenyl)pyrrolidin-3-yl]-1-(3-trimethylsilanylpropyl)-3H-imidazol-1-ium chloride
3-[1-(4-Amino-3-methylphenyl)pyrrolidin-3-yl]-1-(3-trimethylsilanyl-propyl)-3H-imidazol-1-ium chloride
[1-(4-aminophenyl)pyrrolidin-3-yl]ethyldimethylammonium chloride
[1-(4-aminophenyl)pyrrolidin-3-yl]ethyldimethylammonium iodide
[1-(4-Aminophenyl)pyrrolidin-3-yl]propyldimethylammonium iodide
[1-(4-aminophenyl)pyrrolidin-3-yl]propyldimethylammonium bromide
[1-(4-aminophenyl)pyrrolidin-3-yl]propyldimethylammonium methosulphate
[1-(4-aminophenyl)pyrrolidin-3-yl]butyldimethylammonium iodide
[1-(4-aminophenyl)pyrrolidin-3-yl]pentyldimethylammonium iodide
[1-(4-aminophenyl)pyrrolidin-3-yl]hexyldimethylammonium iodide
[1-(4-aminophenyl)pyrrolidin-3-yl]heptyldimethylammonium iodide
[1-(4-aminophenyl)pyrrolidin-3-yl]octyldimethylammonium iodide
[1-(4-aminophenyl)pyrrolidin-3-yl]decyldimethylammonium iodide
[1-(4-aminophenyl)pyrrolidin-3-yl]hexadecyldimethylammonium iodide
[1-(4-aminophenyl)pyrrolidin-3-yl]hydroxyethyldimethylammonium chloride
[1-(4-aminophenyl)pyrrolidin-3-yl]hydroxyethyldimethylammonium iodide.

74. The composition of claim 3, wherein the cationic tertiary para-phenylene is chosen from the group consisting of:
[1-(4-Aminophenyl)pyrrolidin-3-yl]trimethylammonium chloride
[1-(4-Aminophenyl)pyrrolidin-3-yl]dimethyltetradecylammonium bromide
N'-[1-(4-Aminophenyl)pyrrolidin-3-yl]-N,N-dimethylguanidinium chloride
N-[1-(4-Aminophenyl)pyrrolidin-3-yl]guanidinium chloride
3-[1-(4-Aminophenyl)pyrrolidin-3-yl]-1-methyl-3H-imidazol-1-ium chloride
[1-(4-Aminophenyl)pyrrolidin-3-yl]-(2-hydroxyethyl)dimethylammonium chloride
[1-(4-Aminophenyl)pyrrolidin-3-yl]dimethyl-(3-trimethylsilanylpropyl)ammonium chloride
[1-(4-Aminophenyl)pyrrolidin-3-yl]-(trimethylammoniumhexyl)dimethylammonium dichloride
1'-(4-Aminophenyl)-1-methyl-[1,3']bipyrrolidinyl-1-ium chloride
3-[1-(4-Aminophenyl)pyrrolidin-3-yl]-1-(3-trimethylsilanylpropyl)-3H-imidazol-1-ium chloride
3-[1-(4-Amino-3-methylphenyl)pyrrolidin-3-yl]-1-(3-trimethylsilanylpropyl)-3H-imidazol-1-ium chloride
[1-(4-aminophenyl)pyrrolidin-3-yl]ethyldimethylammonium chloride
[1-(4-aminophenyl)pyrrolidin-3-yl]ethyldimethylammonium iodide
[1-(4-aminophenyl)pyrrolidin-3-yl]propyldimethylammonium iodide
[1-(4-aminophenyl)pyrrolidin-3-yl]propyldimethylammonium bromide
[1-(4-aminophenyl)pyrrolidin-3-yl]propyldimethylammonium methosulphate
[1-(4-aminophenyl)pyrrolidin-3-yl]butyldimethylammonium iodide
[1-(4-aminophenyl)pyrrolidin-3-yl]pentyldimethylammonium iodide
[1-(4-aminophenyl)pyrrolidin-3-yl]hexyldimethylammonium iodide
[1-(4-aminophenyl)pyrrolidin-3-yl]heptyldimethylammonium iodide
[1-(4-aminophenyl)pyrrolidin-3-yl]octyldimethylammonium iodide
[1-(4-aminophenyl)pyrrolidin-3-yl]decyldimethylammonium iodide
[1-(4-aminophenyl)pyrrolidin-3-yl]hexadecyldimethylammonium iodide
[1-(4-aminophenyl)pyrrolidin-3-yl]hydroxyethyldimethylammonium chloride
[1-(4-aminophenyl)pyrrolidin-3-yl]hydroxyethyldimethylammonium iodide.

75. The composition of claim 3, wherein the cationic tertiary para-phenylene is chosen from the group consisting of:
[1-(4-Aminophenyl)pyrrolidin-3-yl]trimethylammonium chloride
3-[1-(4-Aminophenyl)pyrrolidin-3-yl]-1-methyl-3H-imidazol-1-ium chloride
[1-(4-Aminophenyl)pyrrolidin-3-yl]-(2-hydroxyethyl)dimethylammonium chloride
1'-(4-Aminophenyl)-1-methyl-[1,3']bipyrrolidinyl-1-ium chloride.

76. The composition of claim 3, wherein the cationic tertiary para-phenylene is chosen from the group consisting of:
[1-(4-Aminophenyl)pyrrolidin-3-yl]trimethylammonium chloride, and
[1-(4-Aminophenyl)pyrrolidin-3-yl]-(2-hydroxyethyl) dimethylammonium chloride.

77. The composition of claim 4, wherein the cationic tertiary para-phenylenediamine is such that n is equal to 0.

78. The composition of claim 4, wherein the cationic tertiary para-phenylenediamine is such that n is equal to 1 and $R_1$ is chosen from the group consisting of a halogen atom; a saturated or unsaturated, aliphatic or alicyclic, $C_1$–$C_6$ hydrocarbon chain; it being possible for one or more carbon atoms to be replaced by an oxygen, nitrogen, silicon or sulphur atom, or by an $SO_2$ group, the radical $R_1$ not containing a peroxide bond, or diazo, nitro or nitroso radicals.

79. The composition of claim 4, wherein the cationic tertiary para-phenylenediamine is such that $R_1$ is chosen from chlorine, bromine, $C_1$–$C_4$ alkyl, $C_1$–$C4$ hydroxyalkyl, $C_1$–$C4$ aminoalkyl, $C_1$–$C_4$ alkoxy or $C_1$–$C_4$ hydroxyalkoxy radicals.

80. The composition of claim 79, wherein the cationic tertiary para-phenylenediamine is such that $R_1$ is chosen from a methyl, hydroxymethyl, 2-hydroxyethyl, 1,2-dihydroxyethyl, methoxy, isopropyloxy or 2-hydroxyethoxy radical.

81. The composition of claim 4, wherein the cationic tertiary para-phenylenediamine is such that $R_2$ represents the onium radical Z corresponding to formula (II)

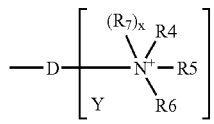

in which
- D is a single bond of a linear or branched $C_1$–$C_{14}$ alkylene chain which may contain one or more heteroatoms chosen from oxygen, sulphur or nitrogen, and which may be substituted with one or more hydroxyl, $C_1$–$C_6$ alkoxy or amino radicals and which may carry one or more ketone functional groups;
- $R_4$, $R_5$ and $R_6$, taken separately, represent a $C_1$–$C_{15}$ alkyl radical; a $C_1$–$C_6$ monohydroxyalkyl radical; a $C_2$–$C_6$ polyhydroxyalkyl radical; a $(C_1$–$C_6)$alkoxy$(C_1$–$C_6)$ alkyl radical; an aryl radical; a benzyl radical; a $C_1$–$C_6$ amidoalkyl radical; a tri$(C_1$–$C_6)$alkylsilane$(C_1$–$C_6)$ alkyl radical; a $C_1$–$C_6$ aminoalkyl radical; a $C_1$–$C_6$ aminoalkyl radical in which the amine is mono- or di-substituted with a $C_1$–$C_4$ alkyl, $(C_1$–$C_6)$alkylcarbonyl, amido or $(C_1$–$C_6)$alkylsulphonyl radical; or
- $R_4$, $R_5$ and $R_6$ together, in pairs, form, with the nitrogen atom to which they are attached, a 4-, 5-, 6- or 7-membered saturated carbon ring which may contain one or more heteroatoms, it being possible for the cationic ring to be substituted with a halogen atom, a hydroxyl radical, a $C_1$–$C_6$ alkyl radical, a $C_1$–$C_6$ monohydroxyalkyl radical, a $C_2$–$C_6$ polyhydroxy-alkyl radical, a $C_1$–$C_6$ alkoxy radical, a tri$(C_1$–$C_6)$alkylsilane $(C_1$–$C_6)$alkyl radical, an amido radical, a carboxyl radical, a $(C_1$–$C_6)$alkylcarbonyl radical, a thio (—SH) radical, a $C_1$–$C_6$ thioalkyl (—R—SH) radical, a $(C_1$–$C_6)$alkylthio radical, an amino radical, an amino radical which is mono- or di-substituted with a $(C_1$–$C_6)$ alkyl, $(C_1$–$C_6)$alkylcarbonyl, amido or $(C_1$–$C_6)$alkylsulphonyl radical;
- $R_7$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical; a $C_1$–$C_6$ aminoalkyl radical whose amine is mono- or di-substituted with a $(C_1$–$C_6)$alkyl, $(C_1$–$C_6)$ alkylcarbonyl, amido or $(C_1$–$C_6)$alkylsulphonyl radical; a $C_1$–$C_6$ carboxyalkyl radical; a $C_1$–$C_6$ carbamylalkyl radical; a $C_1$–$C_6$ trifluroalkyl radical; a tri$(C_1$–$C_6)$alkylsilane$(C_1$–$C_6)$alkyl radical; a $C_1$–$C_6$ sulphonamidoalkyl radical; a $(C_1$–$C_6)$alkylcarboxy $(C_1$–$C_6)$alkyl radical; a $(C_1$–$C_6)$alkylsulphinyl$(C_1$–$C_6)$ alkyl radical; a $(C_1$–$C_6)$alkylsulphonyl$(C_1$–$C_6)$alkyl radical; a $(C_1$–$C_6)$alkylcarbonyl$(C_1$–$C_6)$alkyl radical; an N—$(C_1$–$C_6)$alkylcarbamyl$(C_1$–$C_6)$alkyl radical; an N—$(C_1$–$C_6)$alkylsulphonamido$(C_1$–$C_6)$alkyl radical;
- x is 0 or 1,
    - when x=0, then the linking arm is attached to the nitrogen atom carrying the radicals $R_4$ to $R_6$;
    - when x=1, then two of the radicals $R_4$ to $R_6$ form, together with the nitrogen atom to which they are attached, a 4-, 5-, 6- or 7-membered saturated ring and D is linked to the carbon atom of the saturated ring;
- Y is a counter-ion.

82. The composition of claim 81, wherein the cationic tertiary para-phenylenediamine is such that $R_2$ corresponds to formula II in which x is equal to 0 and $R_4$, $R_5$ and $R_6$ separately are preferably chosen from a $C_1$–$C_6$ alkyl radical, a $C_1$–$C_4$ monohydroxyalkyl radical, a $C_2$–$C_4$ polyhydroxyalkyl radical, a $(C_1$–$C_6)$alkoxy$(C_1$–$C_4)$alkyl radical, a $C_1$–$C_6$ amidoalkyl radical, a tri$(C_1$–$C_6)$alkylsilane$(C_1$–$C_6)$alkyl radical, or $R_4$ with $R_5$ form together an azetidine ring, a pyrrolidine, piperidine, piperazine or morpholine ring, $R_6$ being chosen in this case from a $C_1$–$C_6$ alkyl radical; a $C_1$–$C_6$ monohydroxyalkyl radical, a $C_2$–$C_6$ polyhydroxyalkyl radical; a $C_1$–$C_6$ aminoalkyl radical, an aminoalkyl radical which is mono- or di-substituted with a $(C_1$–$C_6)$alkyl radical, a $(C_1$–$C_6)$alkylcarbonyl, amido or $(C_1$–$C_6)$alkylsulphonyl radical; a $C_1$–$C_6$ carbamylalkyl radical; a tri$(C_1$–$C_6)$ alkylsilane$(C_1$–$C_6)$alkyl radical; a $(C_1$–$C_6)$alkyl carboxy $(C_1$–$C_6)$alkyl radical; a $(C_1$–$C_6)$alkylcarbonyl$(C_1$–$C_6)$alkyl radical; an N—$(C_1$–$C_6)$alkylcarbamyl$(C_1$–$C_6)$alkyl radical.

83. The composition of claim 81, wherein the cationic tertiary para-phenylenediamine is such that $R_2$ corresponds to formula II in which x is equal to 1 and $R_7$ is chosen from a $C_1$–$C_6$ alkyl radical; a $C_1$–$C_6$ monohydroxyalkyl radical; a $C_2$–$C_6$ polyhydroxy-alkyl radical; a $C_1$–$C_6$ aminoalkyl radical, a $C_1$–$C_6$ aminoalkyl radical whose amine is mono- or di-substited with a $(C_1$–$C_6)$alkyl, $(C_1$–$C_6)$alkylcarbonyl, amido or a $(C_1$–$C_6)$alkylsulphonyl radical; a $C_1$–$C_6$ carbamylalkyl radical, a tri$(C_1$–$C_6)$alkylsilane$(C_1$–$C_6)$alkyl radical; a $(C_1$–$C_6)$alkylcarboxy$(C_1$–$C_6)$alkyl radical; a $(C_1$–$C_6)$alkylcarbonyl$(C_1$–$C_6)$alkyl radical; an N—$(C_1$–$C_6)$ alkylcarbamyl$(C_1$–$C_6)$alkyl radical; $R_4$ with $R_5$ together form an azetidine, pyrrolidine, piperidine, piperazine or morpholine ring, $R_6$ being chosen in this case from a $C_1$–$C_6$ alkyl radical; a $C_1$–$C_6$ monohydroxyalkyl radical; a $C_2$–$C_6$ polyhydroxyl alkyl radical; a $C_1$–$C_6$ aminoalkyl radical; a $C_1$–$C_6$ aminoalkyl radical whose amine is mono- or di-substituted with a $(C_1$–$C_6)$alkyl, $(C_1$–$C_6)$alkylcarbonyl, amido or $(C_1$–$C_6)$alkylsulphonyl radical; a $C_1$–$C_6$ carbamylalkyl radical; a tri$(C_1$–$C_6)$alkylsilane$(C_1$–$C_6)$alkyl radical; a $(C_1$–$C_6)$alkylcarboxy$(C_1$–$C_6)$alkyl radical; a $(C_1$–$C_6)$alkylcarbonyl$(C_1$–$C_6)$alkyl radical; an N—$(C_1$–$C_6)$alkylcarbamyl$(C_1$–$C_6)$alkyl radical.

84. The composition of claim 81, wherein the cationic tertiary para-phenylenediamine is such that D is a single bond or an alkylene chain which may be substituted.

85. The composition of claim 81, wherein the cationic tertiary para-phenylenediamine is such that $R_2$ is a trialkylammonium radical.

86. The composition of claim 4, wherein the cationic tertiary para-phenylenediamine is such that $R_2$ represents the onium radical Z corresponding to formula III

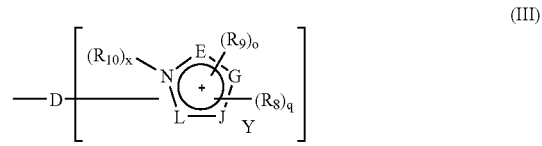

in which
D is a single bond or a linear or branched $C_1$–$C_{14}$ alkylene chain which may contain one or more heteroatoms chosen from oxygen, sulphur or nitrogen, and which may be substituted with one or more hydroxyl, $C_1$–$C_6$ alkoxy or amino radicals, and which may carry one or more ketone functional groups;

the vertices E, G, J, L, which are identical or different, represent a carbon, oxygen, sulphur or nitrogen atom to form a pyrrole, pyrazole, imidazole, triazole, oxazole, isooxazole, thiazole, isothiazole ring, q is an integer between 0 and 4 inclusive;

is an integer between 0 and 3 inclusive;

q+o is an integer between 0 and 4;

the radicals $R_8$, which are identical or different, represent a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical, a tri($C_1$–$C_6$)alkylsilane($C_1$–$C_6$)alkyl radical, an amido radical, a carboxyl radical, a $C_1$–$C_6$ alkylcarbonyl radical, a thio radical, a $C_1$–$C_6$ thioalkyl radical, a ($C_1$–$C_6$) alkylthio radical, an amino radical, an amino radical which is mono- or di-substituted with a ($C_1$–$C_6$)alkyl, ($C_1$–$C_6$)alkylcarbonyl, amido or ($C_1$–$C_6$)alkylsulphonyl radical; a $C_1$–$C_6$ monohydroxyalkyl radical or a $C_2$–$C_6$ polyhydroxyalkyl radical; it being understood that the radicals $R_8$ are carried by a carbon atom, the radicals $R_9$, which are identical or different, represent a $C_1$–$C_6$ alkyl radical, a $C_1$–$C_6$ monohydroxyalkyl radical, a $C_2$–$C_6$ polyhydroxyalkyl radical, a tri($C_1$–$C_6$)alkylsilane($C_1$–$C_6$)alkyl radical, a ($C_1$–$C_6$)alkoxy ($C_1$–$C_6$)alkyl radical, a $C_1$–$C_6$ carbamylalkyl radical, a ($C_1$–$C_6$)alkylcarboxy($C_1$–$C_6$)alkyl radical, a benzyl radical; it being understood that the radicals $R_9$ are carried by a nitrogen, $R_{10}$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical whose amine is substituted with a ($C_1$–$C_6$)alkyl, ($C_1$–$C_6$)alkylcarbonyl, amido or ($C_1$–$C_6$)alkylsulphonyl radical; a $C_1$–$C_6$ carboxyalkyl radical; a $C_1$–$C_6$ carbamylalkyl radical; a $C_1$–$C_6$ trifluroalkyl radical; a tri($C_1$–$C_6$)alkylsilane($C_1$–$C_6$)alkyl radical; a $C_1$–$C_6$ sulphonamidoalkyl radical; a ($C_1$–$C_6$)alkylcarboxy($C_1$–$C_6$)alkyl radical; a ($C_1$–$C_6$)alkylsulphonyl($C_1$–$C_6$)alkyl radical; a ($C_1$–$C_6$) alkylsulphonyl($C_1$–$C_6$)alkyl radical; a ($C_1$–$C_6$)alkylcarbonyl($C_1$–$C_6$)alkyl radical; an N—($C_1$–$C_6$)alkylcarbamyl($C_1$–$C_6$)alkyl radical; an N—($C_1$–$C_6$)alkylsulphonamido($C_1$–$C_6$)alkyl radical;

x is 0 or 1 when x=0, the linking arm D is attached to the nitrogen atom, when x=1, the linking arm D is attached to one of the vertices E, G, J or L, Y is a counter-ion.

87. The composition of claim 86, wherein the cationic tertiary para-phenylenediamine is such that the vertices E, G, J and L form an imidazole ring.

88. The composition of claim 86, wherein the cationic tertiary para-phenylenediamine is such that x is equal to 0, D is a single bond or an alkylene chain which may be substituted.

89. The composition of claim 4, wherein the cationic tertiary para-phenylenediamine is such that $R_2$ represents an onium radical Z corresponding to formula IV

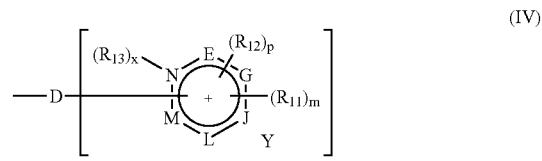

in which:

D is a single bond or a linear or branched $C_1$–$C_{14}$ alkylene chain which may contain one or more heteroatoms chosen from an oxygen, sulphur or nitrogen atom, and which may be substituted with one or more hydroxyl, $C_1$–$C_6$ alkoxy or amino radicals, and which may carry one or more ketone functional groups;

the vertices E, G, J, L and M, which are identical or different, represent a carbon, oxygen, sulphur or nitrogen atom to form a ring chosen from the pyridine, pyrimidine, pyrazine, triazine and pyridazine rings;

p is an integer between 0 and 3 inclusive;

m is an integer between 0 and 5 inclusive;

p+m is an integer between 0 and 5;

the radicals $R_{11}$, which are identical or different, represent a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical, a tri($C_1$–$C_6$)alkylsilane($C_1$–$C_6$)alkyl radical, an amido radical, a carboxyl radical, a $C_1$–$C_6$ alkylcarbonyl radical, a thio radical, a $C_1$–$C_6$ thioalkyl radical, a ($C_1$–$C_6$) alkylthio radical, an amino radical, an amino radical which is substituted with a ($C_1$–$C_6$)alkyl, ($C_1$–$C_6$) alkylcarbonyl, amido or ($C_1$–$C_6$)alkylsulphonyl radical; a $C_1$–$C_6$ monohydroxyalkyl radical or a $C_2$–$C_6$ polyhydroxyalkyl radical; it being understood that the radicals $R_{11}$ are carried by a carbon atom, the radicals $R_{12}$, which are identical or different, represent a $C_1$–$C_6$ alkyl radical, a $C_1$–$C_6$ monohydroxyalkyl radical, a $C_2$–$C_6$ polyhydroxyalkyl radical, a tri($C_1$–$C_6$)alkylsilane($C_1$–$C_6$)alkyl radical, a ($C_1$–$C_6$)alkoxy ($C_1$–$C_6$)alkyl radical, a $C_1$–$C_6$ carbamylalkyl radical, a ($C_1$–$C_6$)alkylcarboxy($C_1$–$C_6$)alkyl radical, a benzyl radical; it being understood that the radicals $R_{12}$ are carried by a nitrogen, $R_{13}$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical whose amine is mono- or di-substituted with a ($C_1$–$C_6$)alkyl, ($C_1$–$C_6$) alkylcarbonyl, amido or ($C_1$–$C_6$)alkylsulphonyl radical; a $C_1$–$C_6$ carboxyalkyl radical; a $C_1$–$C_6$ carbamylalkyl radical; a $C_1$–$C_6$ trifluroalkyl radical; a tri ($C_1$–$C_6$)alkylsilane($C_1$–$C_6$)alkyl radical; a $C_1$–$C_6$ sulphonamidoalkyl radical; a ($C_1$–$C_6$)alkylcarboxy ($C_1$–$C_6$)alkyl radical; a ($C_1$–$C_6$)alkylsulphonyl($C_1$–$C_6$) alkyl radical; a ($C_1$–$C_6$)alkylsulphonyl($C_1$–$C_6$)alkyl radical; a ($C_1$–$C_6$)alkylcarbonyl($C_1$–$C_6$)alkyl radical; an N—($C_1$–$C_6$)alkylcarbamyl($C_1$–$C_6$)alkyl radical; an N—($C_1$–$C_6$)alkylsulphonamido($C_1$–$C_6$)alkyl radical;

x is 0 or 1 when x=0, the linking arm D is attached to the nitrogen atom, when x=1, the linking arm D is attached to one of the vertices E, G, J, L or M, Y is a counter-ion.

90. The composition of claim 89, wherein the vertices E, G, J, L and M form, with the nitrogen of the ring, a ring chosen from pyridine and pyrimidine rings.

91. The composition of claim 89, wherein the cationic tertiary para-phenylenediamine is such that x is equal to 0 and $R_{11}$ is chosen from a hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical, a tri($C_1$–$C_6$)alkylsilane($C_1$–$C_6$)alkyl radical, an amido radical, a $C_1$–$C_6$ alkylcarbonyl radical, an amino radical, an amino radical which is mono- or di-substituted with a ($C_1$–$C_6$)alkyl, a ($C_1$–$C_6$)alkylcarbonyl, amido or ($C_1$–$C_6$)alkylsulphonyl radical; a $C_1$–$C_6$ monohydroxyalkyl radical or a $C_2$–$C_6$ polyhydroxyalkyl radical and $R_{12}$ is chosen from a $C_1$–$C_6$ alkyl radical, a $C_1$–$C_6$ monohydroxyalkyl radical, a $C_2$–$C_6$ polyhydroxyalkyl radical, a tri($C_1$–$C_6$)alkylsilane($C_1$–$C_6$) alkyl radical, a ($C_1$–$C_6$)alkoxy($C_1$–$C_6$)alkyl radical, a $C_1$–$C_6$ carbamylalkyl radical.

92. The composition of claim 89, wherein the cationic tertiary para-phenylenediamine is such that x is equal to 1 and $R_{13}$ is chosen from a $C_1$–$C_6$ alkyl radical; a $C_1$–$C_6$ monohydroxyalkyl radical; a $C_2$–$C_6$ polyhydroxyalkyl radical; a $C_1$–$C_6$ aminoalkyl radical, a $C_1$–$C_6$ aminoalkyl radical whose amine is mono- or di-substituted with a ($C_1$–$C_6$)alkyl radical, a ($C_1$–$C_6$)alkylcarbonyl radical, an amido radical, a ($C_1$–$C_6$)alkylsulphonyl radical; a $C_1$–$C_6$ carbamylalkyl radical; a tri($C_1$–$C_6$)alkylsilane($C_1$–$C_6$)alkyl radical; a ($C_1$–$C_6$) alkylcarbonyl($C_1$–$C_6$)alkyl radical; an N—($C_1$–$C_6$)alkylcarbamyl($C_1$–$C_6$)alkyl radical; $R_{11}$ is chosen from a hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical, a tri($C_1$–$C_6$)alkylsilane($C_1$–$C_6$)alkyl radical, an amido radical, a $C_1$–$C_6$ alkylcarbonyl radical, an amino radical, an amino radical which is mono- or di-substituted with a ($C_1$–$C_6$)alkyl, ($C_1$–$C_6$)alkylcarbonyl, amido or ($C_1$–$C_6$)alkylsulphonyl radical; and $R_{12}$ is chosen from a $C_1$–$C_6$ alkyl radical, a $C_1$–$C_6$ monohydroxyalkyl radical, a $C_2$–$C_6$ polyhydroxyalkyl radical, a tri($C_1$–$C_6$)alkylsilane ($C_1$–$C_6$)alkyl radical, a ($C_1$–$C_6$)alkoxy($C_1$–$C_6$)alkyl radical, a $C_1$–$C_6$ carbamylalkyl radical.

93. The composition of claim 89, wherein the cationic tertiary para-phenylenediamine is such that $R_{11}$, $R_{12}$ and $R_{13}$ are alkyl radicals which may be substituted.

94. The composition of claim 4, wherein the cationic tertiary para-phenylenediamine is such that the radical $R_2$ is the radical of formula —XP(O)(O—) OCH$_2$CH$_2$N$^+$(CH$_3$)$_3$ where X represents an oxygen atom or a radical —NR$_{14}$, $R_{14}$ representing a hydrogen, a $C_1$–$C_4$ alkyl radical or a hydroxyalkyl radical.

95. The composition of claim 4, wherein the cationic tertiary para-phenylenediamine is such that the radical $R_2$ is a guanidine radical of formula —X—C=NR$_8$—NR$_9$R$_{10}$, X represents an oxygen atom or a radical NR$_{11}$, R$_8$, R$_9$, R$_{10}$ and $R_{11}$ representing a hydrogen, a $C_1$–$C_4$ alkyl radical or a hydroxyalkyl radical.

96. The composition of claim 4, wherein the cationic tertiary para-phenylene is chosen from the group consisting of:

[1-(4-Aminophenyl)pyrrolidin-3-yl]trimethylammonium chloride,

[1-(4-Aminophenyl)pyrrolidin-3-yl]dimethyltetradecylammonium bromide

N'-[1-(4-Aminophenyl)pyrrolidin-3-yl]-N,N-dimethylguanidinium chloride

N—[1-(4-Aminophenyl)pyrrolidin-3-yl]guanidinium chloride

3-[1-(4-Aminophenyl)pyrrolidin-3-yl]-1-methyl-3H-imidazol-1-ium chloride

[1-(4-Aminophenyl)pyrrolidin-3-yl]-(2-hydroxyethyl)dimethylammonium chloride

[1-(4-Aminophenyl)pyrrolidin-3-yl]dimethyl-(3-trimethylsilanylpropyl)ammonium chloride

[1-(4-Aminophenyl)pyrrolidin-3-yl]-(trimethylammonium-hexyl)dimethylammonium dichloride

[1-(4-Aminophenyl)pyrrolidin-3-yl]oxophosphorylcholine

{2-[1-(4-Aminophenyl)pyrrolidin-3-yloxy]ethyl}trimethylammonium chloride

1-{2-[1-(4-Aminophenyl)pyrrolidin-3-yloxy]ethyl}-1-methylpyrrolidinium chloride

3-{3-[1-(4-Aminophenyl)pyrrolidin-3-yloxy]propyl}-1-methyl-3H-imidazol-1-ium chloride 1-{2-[1-(4-Aminophenyl)pyrrolidin-3-yloxy]ethyl}-1-methylpiperidinium chloride 3-{3-[1-(5-trimethylsilanylethyl-4-Amino-3-trimethylsilanylethylphenyl)pyrrolidin-3-yloxy]propyl}-1-methyl-3H-imidazol-1-ium chloride

[1-(4-Amino-3-methylphenyl)pyrrolidin-3-yl]trimethylammonium chloride

[1-(4-Amino-3-methylphenyl)pyrrolidin-3-yl]dimethyltetradecylammonium chloride

N'-[1-(4-Amino-3-methylphenyl)pyrrolidin-3-yl]-N,N-dimethylguanidinium chloride

N—[1-(4-Amino-3-methylphenyl)pyrrolidin-3-yl]guanidinium chloride

3-[1-(4-Amino-3-methylphenyl)pyrrolidin-3-yl]-1-methyl-3H-imidazol-1-ium chloride

[1-(4-Amino-3-methylphenyl)pyrrolidin-3-yl]-(2-hydroxyethyl)dimethylammonium chloride

[1-(4-Amino-3-methylphenyl)pyrrolidin-3-yl]dimethyl-(3-trimethylsilanylpropylammonium chloride

[1-(4-Amino-3-methylphenyl)pyrrolidin-3-yl]-(trimethylammoniumhexyl-dimethylammonium dichloride

[1-(4-Amino-3-methylphenyl)pyrrolidin-3-yl]oxophosphorylcholine

{2-[1-(4-Amino-3-methylphenyl)pyrrolidin-3-yloxy]ethyl}trimethylammonium chloride 1-{2-[1-(4-Amino-3-methylphenyl)pyrrolidin-3-yloxy]ethyl}-1-methylpyrrolidinium chloride 3-{3-[1-(4-Amino-3-methylphenyl)pyrrolidin-3-yloxy]propyl}1-methyl-3H-imidazol-1-um chloride 1-{2-[1-(4-Amino-3-methylphenyl)pyrrolidin-3-yloxy]ethyl}-1-methylpiperidinium chloride

[1-(4-Amino-3-trimethylsilanylethylphenyl)pyrrolidin-3-yl]trimethylammonium chloride 3-[1-(4-Amino-3-trimethylsilanylethylphenyl)pyrrolidin-3-yl]-1-methyl-3H-imidazol-1-ium chloride 3-{3-[1-(4-Amino-3-trimethylsilanylethylphenyl)pyrrolidin-3-yloxy]propyl}-1-methyl-3H-imidazol-1-ium chloride

[1-(5-trimethylsilanylethyl-4-Amino-3-trimethylsilanylethylphenyl)pyrrolidin-3-yl]trimethylammonium chloride 3-[1-(5-trimethylsilanylethyl-4-Amino-3-trimethylsilanylethylphenyl)pyrrolidin-3-yl]-1-methyl-3H-imidazol-1-ium chloride 1'-(4-Aminophenyl)-1-methyl-[1,3']bipyrrolidinyl-1-ium chloride 1'-(4-Amino-3-methylphenyl)-1-methyl-[1,3']bipyrrolidinyl-1-ium chloride 3-{[1-(4-Aminophenyl)pyrrolidin-3-ylcarbamoyl]methyl}-1-methyl-3H-imidazol-1-ium chloride 3-{[1-(4-Amino-3-methylphenyl)pyrrolidin-3-ylcarbamoyl]methyl}-1-methyl-3H-imidazol-1-ium chloride
3-[1-(4-Aminophenyl)pyrrolidin-3-yl]-1-(3-trimethylsilanylpropyl)-3H-imidazol-1-ium chloride
3-[1-(4-Aminophenyl)pyrrolidin-3-yl]-1-(3-trimethylsilanylpropyl)-3H-imidazol-1-ium chloride
[1-(4-aminophenyl)pyrrolidin-3-yl]ethyldimethylammonium chloride
[1-(4-aminophenyl)pyrrolidin-3-yl]ethyldimethylammonium iodide
[1-(4-aminophenyl)pyrrolidin-3-yl]propyldimethylammonium iodide,
[1-(4-aminophenyl)pyrrolidin-3-yl]propyldimethylammonium bromide
[1-(4-aminophenyl)pyrrolidin-3-yl]propyldimethylammonium methosulphate
[1-(4-aminophenyl)pyrrolidin-3-yl]butyldimethylammonium iodide
[1-(4-aminophenyl)pyrrolidin-3-yl]pentyldimethylammonium iodide
[1-(4-aminophenyl)pyrrolidin-3-yl]hexyldimethylammonium iodide
[1-(4-aminophenyl)pyrrolidin-3-yl]heptyldimethylammonium iodide
[1-(4-Aminophenyl)pyrrolidin-3-yl]octyldimethylammonium iodide
[1-(4-aminophenyl)pyrrolidin-3-yl]decyldimethylammonium iodide
[1-(4-aminophenyl)pyrrolidin-3-yl]hexadecyldimethylammonium iodide
[1-(4-aminophenyl)pyrrolidin-3-yl]hydroxyethyldimethylammonium chloride
[1-(4-aminophenyl)pyrrolidin-3-yl]hydroxyethyldimethylammonium iodide.

97. The composition of claim 4, wherein the cationic tertiary para-phenylene is chosen from the group consisting of:
[1-(4-Aminophenyl)pyrrolidin-3-yl]trimethylammonium chloride
[1-(4-Aminophenyl)pyrrolidin-3-yl]dimethyltetradecylammonium bromide
N'-[1-(4-Aminophenyl)pyrrolidin-3-yl]-N,N-dimethylguanidinium chloride
N-[1-(4-Aminophenyl)pyrrolidin-3-yl]guanidinium chloride
3-[1-(4-Aminophenyl)pyrrolidin-3-yl]-1-methyl-3H-imidazol-1-ium chloride
[1-(4-Aminophenyl)pyrrolidin-3-yl](2-hydroxyethyl)dimethylammonium chloride
[1-(4-Aminophenyl)pyrrolidin-3-yl]dimethyl-(3-trimethylsilanylpropyl)ammonium chloride
[1-(4-Amino-3-methylphenyl)pyrrolidin-3-yl]trimethylammonium chloride
[1-(4-Amino-3-methylphenyl)pyrrolidin-3-yl]dimethyltetradecylammonium chloride
N'-[1-(4-Amino-3-methylphenyl)pyrrolidin-3-yl]-N,N-dimethylguanidinium chloride
N-[1-(4-Amino-3-methylphenyl)pyrrolidin-3-yl]guanidinium chloride
3-[1-(4-Amino-3-methylphenyl)pyrrolidin-3-yl]-1-methyl-3H-imidazol-1-ium chloride
[1-(4-Amino-3-methylphenyl)pyrrolidin-3-yl]-(2-hydroxyethyl)dimethylammonium chloride
[1-(4-Amino-3-methylphenyl)pyrrolidin-3-yl]dimethyl-(3-trimethylsilanylpropylammonium chloride
1'-(4-Aminophenyl)-1-methyl-[1,3']bipyrrolidinyl-1-ium chloride
1'-(4-Amino-3-methylphenyl)-1-methyl-[1,3']bipyrrolidinyl-1-ium chloride
3-{[1-(4-Aminophenyl)pyrrolidin-3-ylcarbamoyl]methyl}-1-methyl-3H-imidazol-1-ium chloride
3-{[1-(4-Amino-3-methylphenyl)pyrrolidin-3-ylcarbamoyl]methyl}-1-methyl-3H-imidazol-1-ium chloride
3-[1-(4-Aminophenyl)pyrrolidin-3-yl]-1-(3-trimethylsilanylpropyl)-3H1-imidazol-1-ium chloride
3-[1-(4-Amino-3-methylphenyl)pyrrolidin-3-yl]-1-(3-trimethylsilanyl-propyl)-3H-imidazol-1-ium chloride
[1-(4-aminophenyl)pyrrolidin-3-yl]ethyldimethylammonium chloride
[1-(4-aminophenyl)pyrrolidin-3-yl]ethyldimethylammonium iodide
[1-(4-Aminophenyl)pyrrolidin-3-yl]propyldimethylammonium iodide
[1-(4-aminophenyl)pyrrolidin-3-yl]propyldimethylammonium bromide
[1-(4-aminophenyl)pyrrolidin-3-yl]propyldimethylammonium methosulphate
[1-(4-aminophenyl)pyrrolidin-3-yl]butyldimethylammonium iodide
[1-(4-aminophenyl)pyrrolidin-3-yl]pentyldimethylammonium iodide
[1-(4-aminophenyl)pyrrolidin-3-yl]hexyldimethylanimonium iodide
[1-(4-aminophenyl)pyrrolidin-3-yl]heptyldimethylammonium iodide
[1-(4-aminophenyl)pyrrolidin-3-yl]octyldimethylammonium iodide
[1-(4-aminophenyl)pyrrolidin-3-yl]decyldimethylammonium iodide
[1-(4-aminophenyl)pyrrolidin-3-yl]hexadecyldimethylammonium iodide
[1-(4-aminophenyl)pyrrolidin-3-yl]hydroxyethyldimethylammonium chloride
[1-(4-aminophenyl)pyrrolidin-3-yl]hydroxyethyldimethylammonium iodide.

98. The composition of claim 4, wherein the cationic tertiary para-phenylene is chosen from the group consisting of:
[1-(4-Aminophenyl)pyrrolidin-3-yl]trimethylammonium chloride
[1-(4-Aminophenyl)pyrrolidin-3-yl]dimethyltetradecylammonium bromide
N'-[1-(4-Aminophenyl)pyrrolidin-3-yl]-N,N-dimethylguanidinium chloride
N-[1-(4-Aminophenyl)pyrrolidin-3-yl]guanidinium chloride
3-[1-(4-Aminophenyl)pyrrolidin-3-yl]-1-methyl-3H-imidazol-1-ium chloride
[1-(4-Aminophenyl)pyrrolidin-3-yl]-(2-hydroxyethyl)dimethylammonium chloride
[1-(4-Aminophenyl)pyrrolidin-3-yl]dimethyl-(3-trimethylsilanylpropyl)ammonium chloride
[1-(4-Aminophenyl)pyrrolidin-3-yl]-(trimethylammoniumhexyl)dimethylammonium dichloride
1'-(4-Aminophenyl)-1-methyl-[1,3']bipyrrolidinyl-1-ium chloride
3-[1-(4-Aminophenyl)pyrrolidin-3-yl]-1-(3-trimethylsilanylpropyl)-3H-imidazol-1-ium chloride
3-[1-(4-Amino-3-methylphenyl)pyrrolidin-3-yl]-1-(3-trimethylsilanylpropyl)-3H-imidazol-1-ium chloride
[1-(4-aminophenyl)pyrrolidin-3-yl]ethyldimethylammonium chloride
[1-(4-aminophenyl)pyrrolidin-3-yl]ethyldimethylammonium iodide

[1-(4-aminophenyl)pyrrolidin-3-yl]propyldimethylammonium iodide
[1-(4-aminophenyl)pyrrolidin-3-yl]propyldimethylammonium bromide
[1-(4-aminophenyl)pyrrolidin-3-yl]propyldimethylammonium methosulphate
[1-(4-aminophenyl)pyrrolidin-3-yl]butyldimethylammonium iodide
[1-(4-aminophenyl)pyrrolidin-3-yl]pentyldimethylammonium iodide
[1-(4-aminophenyl)pyrrolidin-3-yl]hexyldimethylammonium iodide
[1-(4-aminophenyl)pyrrolidin-3-yl]heptyldimethylammonium iodide
[1-(4-aminophenyl)pyrrolidin-3-yl]octyldimethylammonium iodide
[1-(4-aminophenyl)pyrrolidin-3-yl]decyldimethylammonium iodide
[1-(4-aminophenyl)pyrrolidin-3-yl]hexadecyldimethylammonium iodide
[1-(4-aminophenyl)pyrrolidin-3-yl]hydroxyethyldimethylammonium chloride
[1-(4-aminophenyl)pyrrolidin-3-yl]hydroxyethyldimethylammonium iodide.

99. The composition of claim 4, wherein the cationic tertiary para-phenylene is chosen from the group consisting of:
[1-(4-Aminophenyl)pyrrolidin-3-yl]trimethylammonium chloride
3-[1-(4-Aminophenyl)pyrrolidin-3-yl]-1-methyl-3H-imidazol-1-ium chloride
[1-(4-Aminophenyl)pyrrolidin-3-yl]-(2-hydroxyethyl)dimethylammonium chloride
1'-(4-Aminophenyl)-1-methyl-[1,3']bipyrrolidinyl-1-ium chloride.

100. The composition of claim 4, wherein the cationic tertiary para-phenylene is chosen from the group consisting of:
[1-(4-Aminophenyl)pyrrolidin-3-yl]trimethylammonium chloride, and
[1-(4-Aminophenyl)pyrrolidin-3-yl]-(2-hydroxyethyl)dimethylammonium chloride.

* * * * *

UNITED STATES PATENT AND TRADEMARK OFFICE
CERTIFICATE OF CORRECTION

PATENT NO. : 7,101,406 B2
APPLICATION NO. : 10/735259
DATED : September 5, 2006
INVENTOR(S) : Cotteret and Lagrange It is certified that error appears in the above-identified patent and that said Letters Patent is hereby corrected as shown below:

In claim 17, column 90, lines 8-9, delete "(C1-C6)alkylsulphonyl(C1-C6)alkyl radical" therefor.

In claim 24, column 91, lines 26-27, delete "oxophosphoryleholine" and insert --oxophosphorylcholine-- therefor.

In claim 24, column 92, line 4, delete "imidazol-1-um" and insert --imidazol-1-ium-- therefor.

In claim 24, column 92, lines 38-39, delete "hexyldimethylanimonium" and insert --hexyldimethylammonium-- therefor.

In claim 25, column 92, line 56, delete "trimethylanimonium" and insert --trimethylammonium-- therefor.

In claim 41, column 98, line 37, before "polyhydroxyalkyl" insert --C2-C6-- therefor.

In claim 41, column 98, line 63, delete "trifluroalkyl radical" and insert --trifluoroalkyl radical-- therefor.

In claim 48, column 101, lines 11-12, delete "3-{[1-(Aminophenyl)pyrrolidin-3-yl]carbamoylmethyl}-1-methyl-3H-imidazol-1-ium chloride" and insert --3-{[1-(Aminophenyl)pyrrolidin-3-ylcarbamoyl]methyl}-1-methyl-3H-imidazol-1-ium chloride-- therefor.

In claim 48, column 101, lines 13-14, delete "3-{[1-(4-Amino-3-methylphenyl)pyrrolidin-3-yl]carbamoylmethyl}-1-methyl-3H-imidazol-1-ium chloride" and insert --3-{[1-(4-Amino-3-methylphenyl)pyrrolidin-3-ylcarbamoyl]methyl}-1-methyl-3H-imidazol-1-ium chloride --therefor.

In claim 57, column 104, line 67, before "C1-C6)alkylcarbonyl" insert --(-- therefor.

In claim 72, column 110, lines 11-12, delete "3{[1-(4-Aminophenyl)pyrrolidin-3-yl]carbamoylmethyl}-1-methyl-3H-imidazol-1-ium" and insert -- 3{[1-(4-Aminophenyl)pyrrolidin-3-ylcarbamoyl]methyl}-1-methyl-3H-imidazol-1-ium -- therefor.

UNITED STATES PATENT AND TRADEMARK OFFICE
CERTIFICATE OF CORRECTION

| | |
|---|---|
| PATENT NO. | : 7,101,406 B2 |
| APPLICATION NO. | : 10/735259 |
| DATED | : September 5, 2006 |
| INVENTOR(S) | : Cotteret and Lagrange |

It is certified that error appears in the above-identified patent and that said Letters Patent is hereby corrected as shown below:

In claim 72, column 110, lines 13-14, delete "3{[1-(4-Amino-3-methylphenyl)pyrrolidin-3-yl]carbamoylmethyl}-1-methyl-3H-imidazol-1-ium" and insert -- 3{[1-(4-Amino-3-methylphenyl)pyrrolidin-3-ylcarbamoyl]methyl}-1-methyl-3H-imidazol-1-ium -- therefor.

In claim 86, column, 115, line 13, before "is" insert -- o -- therefor.

In claim 57, column 104, line 66-67, delete "(C1-C6)alkylsulphonyl(C1-C6)alkyl radical" therefor.

In claim 62, column 106, line 56-57, delete "(C1-C6)alkylsulphonyl(C1-C6)alkyl radical" therefor.

In claim 65, column 107, line 66-67, delete "(C1-C6)alkylsulphonyl(C1-C6)alkyl radical" therefor.

In claim 81, column 113, line 61-62, delete "(C1-C6)alkylsulphonyl(C1-C6)alkyl radical" therefor.

In claim 86, column 115, line 46-47, delete "(C1-C6)alkylsulphonyl(C1-C6)alkyl radical" therefor.

In claim 89, column 116, line 57-58, delete "(C1-C6)alkylsulphonyl(C1-C6)alkyl radical" therefor.

UNITED STATES PATENT AND TRADEMARK OFFICE
CERTIFICATE OF CORRECTION

PATENT NO. : 7,101,406 B2
APPLICATION NO. : 10/735259
DATED : September 5, 2006
INVENTOR(S) : Cotteret and Lagrange It is certified that error appears in the above-identified patent and that said Letters Patent is hereby corrected as shown below:

In claim 97, column 120, lines 7-8, delete "3-[1-(4-Aminophenyl)pyrrolidin-3-yl]-1-(3-trimethylsilanylpropy)-3H1-imidazol-1-ium" and insert -- 3-[1-(4-Aminophenyl) pyrrolidin-3-yl]-1-(3-trimethylsilanylpropyl)-3H-imidazol-1-ium -- therefor.

Signed and Sealed this

Ninth Day of January, 2007

JON W. DUDAS
*Director of the United States Patent and Trademark Office*